United States Patent [19]
Reitz et al.

[11] Patent Number: 5,643,906
[45] Date of Patent: Jul. 1, 1997

[54] METHOD OF USING N-ARYLHETEROARYLALKYL IMIDAZOL-2-ONE COMPOUNDS FOR TREATMENT OF A GLAUCOMA DISORDER

[75] Inventors: David B. Reitz, Chesterfield; Robert E. Manning, St. Louis, both of Mo.

[73] Assignee: G.D. Searle & Co., Chicago, Ill.

[21] Appl. No.: 86,959

[22] Filed: Jul. 1, 1993

Related U.S. Application Data

[63] Continuation of Ser. No. 894,032, Jun. 4, 1992, abandoned, which is a continuation of Ser. No. 681,011, Apr. 5, 1991, Pat. No. 5,164,403.

[51] Int. Cl.$^6$ .............. A61K 31/535; A61K 31/505; A61K 31/445; A61K 31/411
[52] U.S. Cl. .............. 514/235.8; 546/272.4; 546/274.4; 514/337; 514/340; 514/345; 514/346; 514/350; 514/351; 514/318; 514/326
[58] Field of Search .............. 514/341, 337, 514/326, 235.8, 913, 318, 340, 345, 346, 350, 351; 546/274.4, 272.4

[56] References Cited

FOREIGN PATENT DOCUMENTS 508393   10/1992   European Pat. Off. ...... C07D 401/14
92/07834  5/1992   WIPO ................... C07D 233/70

*Primary Examiner*—C. Warren Ivy
*Assistant Examiner*—Raymond Covington
*Attorney, Agent, or Firm*—J. Timothy Keane

[57] ABSTRACT

A class of N-arylheteroarylalkyl imidazol-2-one compounds is described for use in treatment of a glaucoma disorder. Compounds of particular interest are angiotensin II antagonists of the formula

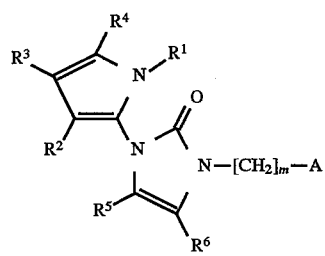

wherein A is selected from

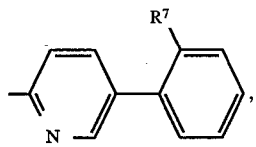

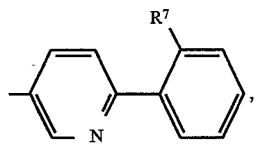

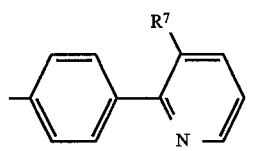

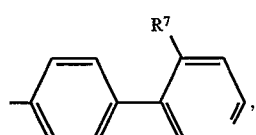

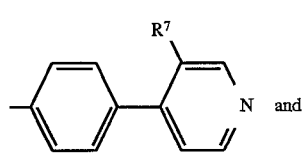

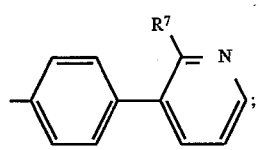

wherein $R^1$ is selected from hydrido and alkyl; wherein each of $R^2$, $R^3$ and $R^4$ is independently selected from hydrido, alkyl, alkoxy, halo, hydroxy, carboxyl, alkoxycarbonyl, formyl and acetyl; wherein $R^5$ is hydrido; wherein $R^6$ is alkyl; wherein $R^7$ is an acidic group selected from COOH and

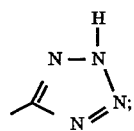

or a stereoisomer or a tautomer thereof or a pharmaceutically-acceptable salt thereof.

18 Claims, No Drawings

METHOD OF USING N-ARYLHETEROARYLALKYL IMIDAZOL-2-ONE COMPOUNDS FOR TREATMENT OF A GLAUCOMA DISORDER

This is a continuation of application Ser. No. 07/894,032 filed Jun. 4, 1992 now abandoned, which is a continuation of parent application Ser. No. 07/681,011 filed on Apr. 5, 1991 now U.S. Pat. No. 5,164,403.

FIELD OF THE INVENTION

Non-peptidic N-arylheteroarylalkyl imidazol-2-one compounds are described for use in treatment of circulatory disorders such as hypertension and congestive heart failure. Of particular interest are angiotensin II antagonist compounds provided by an imidazol-2-one having a arylheteroarylmethyl moiety attached to a nitrogen atom of the imidazol-2-one.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agohist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J, Pharmacol. Exp. Ther.*, 247 (1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 13–21 (1988)]. A family of 1-benzylimidazole-5-acetate derivatives has been shown to have competitive angiotensin II antagonist properties [A. T. Chiu et al, *J. Pharmacol. Exp. Ther.*, 250 (3), 867–874 (1989)]. U.S. Pat. No. 4,816,463 to Blankey et al describes a family of 4,5,6,7-tetrahydro-1H-imidazo (4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published Jan. 20, 1988, describes a series of aralkyl imidazole compounds, including in particular a family of biphenylmethyl substituted imidazoles, as antagonists to the angiotensin II receptor. EP No. 323,841 published Jul. 12, 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of known compounds having one or two oxo substituents on a triazole ring. For example, East German Patent No. 160,447 published Aug. 3, 1983 describes a family of 1,2,4-triazolin-5-one compounds, specifically 2,4-dihydro-4,5-bis(phenylmethyl)-3H-t,2,4-triazol-3-one, for use as herbicides. Belgian Patent No. 806,146 published Oct. 16, 1972 describes a family of triazolinone compounds, including the compound (3-(4-m-chlorophenyl-1-piperazinyl)-propyl)-3,4 -diethyl-1,2,4-triazolin-5-one, having tranquilizer, hypotensive and analgesic activities. Belgian Patent No. 631,842 published Feb. 28, 1963 describes a family of 1,2,4-triazolones having hypnotic, tranquilizer, narcotic, sedative and analgetic activities, which includes a class of 4-N-aralkyl-1,2,4-triazol-5-one compounds. EP #7,180 published Jun. 15, 1978 describes a family of 1,2-disubstituted-4-alkyl-1,2,4-triazolidine-3,5-dione compounds having a wide variety of activities, such as antiulcer, bronchodilator, antifertility and cardiovascular-related activities which include antihypertensive, antiarrhythmic, platelet aggregation inhibition and smooth muscle activities. EP #283,310 published Mar. 18, 1987 describes a family of $N^1$-diarylmethyl-$N^2$-aminoalkyl-diaza-heterocyclic derivatives for treating cerebral vascular and ischemic diseases and for protecting against anoxia.

DESCRIPTION OF THE INVENTIQN

A class of N-substituted arylheteroarylalkyl imidazol-2-one compounds useful in treating circulatory disorders, particularly cardiovascular disorders, is defined by Formula I:

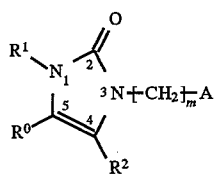

wherein A is selected from

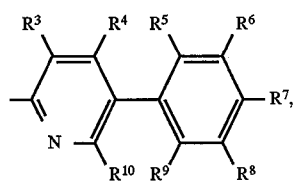

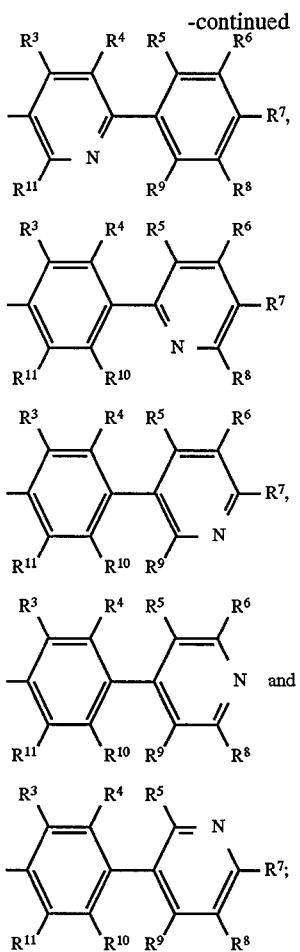

wherein m is a number selected from one to four, inclusive; wherein $R^1$ is selected from alkyl, hydroxyalkyl, haloalkyl, cycloalkyl, cycloalkylalkyl, formyl, aralkyl, aryl, aroyl, alkoxyalkyl, alkylcarbonyl, alkylcarbonylalkyl, cycloalkylcarbonyl, cycloalkylalkylcarbonyl, aralkylcarbonyl, alkoxycarbonyl, alkenyl, cycloalkenyl, aralkoxycarbonyl, alkynyl, alkylthiocarbonyl, alkylthiothiocarbonyl, arylthiocarbonyl, arylthiothiocarbonyl, aralkylthiocarbonyl, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amido radicals of the formula

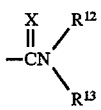

wherein X is oxygen atom or sulfur atom;
wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together may form a heterocyclic group having five to seven ring members including the nitrogen atom of said amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together may form an aromatic heterocyclic group having five ring members including the nitrogen atom of said amido radical and which aromatic heterocyclic group may further contain one or more additional nitrogen atoms; wherein each of $R^o$ and $R^2$ through $R^{11}$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonyl, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^o$ and $R^2$ through $R^{11}$ may be further independently selected from amino and amido radicals of the formula

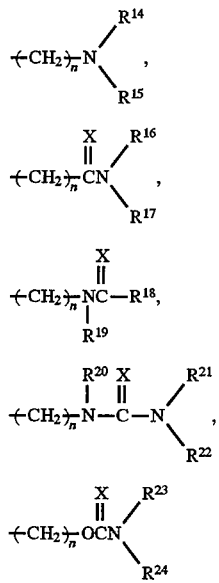

and

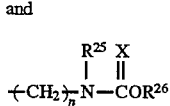

wherein X is oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{14}$ and $R^{15}$ taken together, $R^{16}$ and $R^{17}$ taken together, $R^{18}$ and $R^{19}$ taken together, $R^{21}$ and $R^{22}$ taken together and $R^{23}$ and $R^{24}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{14}$ and $R^{15}$ taken together, $R^{16}$ and $R^{17}$ taken together, $R^{21}$ and $R^{22}$ taken together and $R^{23}$ and $R^{24}$ taken together may each form an aromatic heterocyclic group having five ring members including the nitrogen atom of said amino or amido radical and which aromatic heterocyclic group may further contain one or more additional nitrogen atoms;

and wherein each of $R^0$ and $R^3$ through $R^{11}$ may be further independently selected from hydroxy and acidic moieties of the formula $$-Y_nA$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^0$ through $R^{26}$, Y and A groups having a substitutable position may be substituted by one or more groups independently selected from hydroxy, alkyl, alkenyl, alkynyl, aralkyl, hydroxyalky, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbogyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

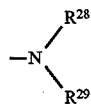

and

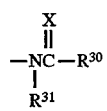

wherein X is oxygen atom or sulfur atom; wherein each of $R^{27}$ through $R^{31}$ is independently selected from hydrido, alkyl, cycloalkyl, cycloalkylalkyl, aralkyl, aryl, $DR^{32}$ and

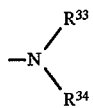

wherein D is selected from oxygen atom and sulfur atom and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{27}$, $R^{28}$, $R^{29}$, $R^{30}$, $R^{31}$, $R^{33}$ and $R^{34}$ is further independently selected from amino and amido radicals of the formula

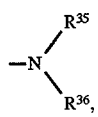

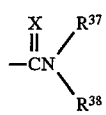

and

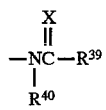

wherein X is oxygen atom or sulfur atom; wherein each of $R^{35}$, $R^{36}$, $R^{37}$, $R^{38}$, $R^{39}$ and $R^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl, and wherein each of $R^{28}$ and $R^{29}$ taken together and each of $R^{30}$ and $R^{31}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{28}$ and $R^{29}$ taken together and each of $R^{33}$ and $R^{34}$ taken together may form an aromatic heterocyclic group having five ring members including the nitrogen atom of said amino or amido radical and which aromatic heterocyclic group may further contain one or more additional nitrogen atoms; or a tautomer thereof or a pharmaceutically-acceptable salt thereof.

Compounds of Formula I would be useful in treating a variety of circulatory disorders, including cardiovascular disorders, such as hypertension, congestive heart failure and arteriosclerosis, and to treat other disorders such as glaucoma. These compounds would also be useful as adjunctire therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

The phrase "acidic group selected to contain at least one acidic hydrogen atom", as used to define the —$Y_nA$ moiety, is intended to embrace chemical groups which, when attached to any of the $R^0$ and $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a $pK_a$ in a range from about one to about twelve. More typically, the Formula I compound would have a $pK_a$ in a range from about two to about seven. An example of an acidic group containing at least one acidic hydrogen atom is carboxyl group (—COOH). Where n is zero and A is —COOH, in the —$Y_nA$ moiety, such carboxyl group would be attached directly to one of the $R^0$ and $R^3$ through $R^{11}$ positions. The Formula I compound may have one —$Y_nA$ moiety attached at one of the $R^3$ through $R^{11}$ positions, or may have a plurality of such —$Y_nA$ moieties attached at more than one of the $R^0$ and $R^3$ through $R^{11}$ positions, up to a maximum of ten such —$Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the —$Y_nA$ moiety attached at one of positions $R^0$, $R^5$, $R^6$, $R^8$ and $R^9$ would be expected to have preferred properties, while attachment at $R^5$ or $R^9$ would be more preferred. Compounds of Formula I having the —$Y_nA$ moiety attached at one of positions $R^5$, $R^6$, $R^8$ and $R^9$ would be expected to have preferred properties, while attachment at $R^5$ or $R^9$ would be more preferred. Compounds of Formula I may have one or more acidic protons and, therefore, may have one or more $pK_a$ values. It is preferred, however, that at least one of these $pK_a$ values of the Formula I compound as conferred by the —$Y_nA$ moiety be in a range from about two to about seven. The —$Y_nA$ moiety may be attached to one of the $R^3$ through $R^{11}$ positions through any portion of the —$Y_nA$ moiety which results in a Formula I compound being relatively stable and also having a labile or acidic proton to meet the foregoing $pK_a$ criteria. For example, where the —$Y_nA$ acid moiety is tetrazole, the tetrazole is attached at the ring carbon tetrazole atom.

A preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkoxycarbonyl, alkenyl, cyclbalkenyl, alkynyl, cycloalkynyl, alkylthiocarbonyl, arylthiocarbonyl, arylthiothiocarbonyl, aralkylthiocarbonyl, alkylsulfonyl, aralkylsulfonyl, arylsulfonyl, heteroaryl having one or more ring atoms selected from oxygen, sulfur and nitrogen atoms, and amido radicals of the formula

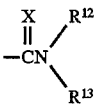

wherein X is oxygen atom or sulfur atom;

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ and $R^2$ through $R^{11}$ may be further independently selected from amino and amido radicals of the formula

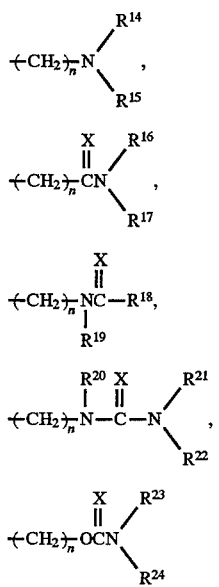

and

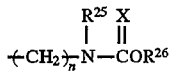

wherein X is selected from oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, atkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, arylthio, arylthiocarbonyl, arylcarbonylthio, arylthiocarbonyloxy, arylthiothiocarbonyl, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfonyl, aralkylsulfonyl and arylsulfonyl, and amino and amido radicals of the formula

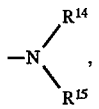

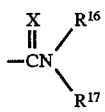

and

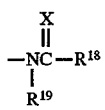

wherein X is oxygen atom or sulfur atom;
wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;
and wherein each of $R^0$ and $R^3$ through $R^{11}$ may be further independently selected from acidic moieties of the formula

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^0$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

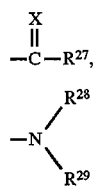

and

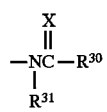

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and

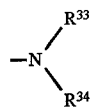

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;
or a tautomer thereof or a pharmaceutically-acceptable salt thereof.

A more preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkoxycarbonyl, alkenyl, cycloalkenyl, alkynyl, cycloalkynyl, alkylsulfonyl, aralkylsulfonyl and arylsulfonyl and amido radicals of the formula

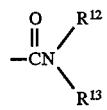

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalklylcarbonylalkyl wherein each of said heteroaryl- and cycloheteroalkyl-containing groups has one or more hetero ring atoms selected from oxygen, sulfur and nitrogen atoms, and wherein each of $R^0$ and $R^2$ may be further independently selected from amino and amido radicals of the formula

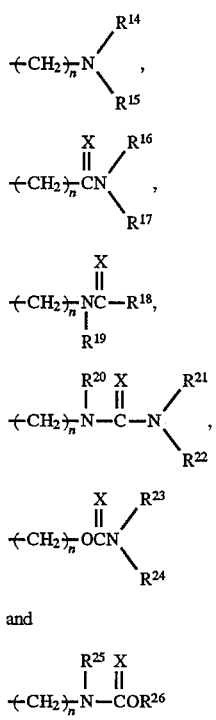

wherein X is selected from oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amino and amido radicals of the formula

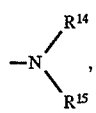

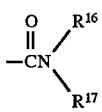

and

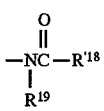

wherein each of $R^{14}$, $R^{15}$, $R^{16}$, $R^{17}$, $R^{18}$ and $R^{19}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
and wherein each of $R^0$ and $R^3$ through $R^{11}$ may be further independently selected from acidic moieties of the formula $$-Y_nA$$

wherein n is a number selected from zero through three, inclusive;
wherein A is selected from carboxylic acid and bioisosteres of carboxylic acid selected from

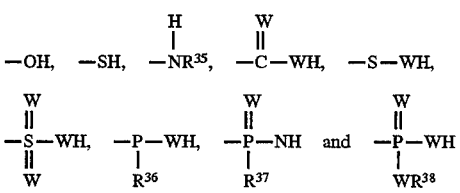

wherein each W is independently selected from oxygen atom, sulfur atom and $NR^{39}$; wherein each of $R^{35}$, $R^{36}$, $R^{37}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$, $R^{36}$, $R^{37}$ and $R^{39}$ may be further independently selected from amino radical of the formula

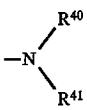

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{36}$ and $R^{37}$ may be further independently selected from hydroxy, alkoxy, alkylthio, aryloxy, arylthio, aralkylthio and aralkoxy; and the amide, ester and salt derivatives of said, acidic groups;
wherein said bioisostere of carboxylic acid may be further selected from heterocyclic acidic groups consisting of heterocyclic rings of four to about nine ring, members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^0$ through $R^{26}$ and $R^{35}$ through $R^{41}$, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

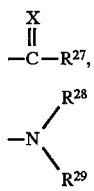

and

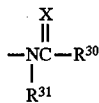

wherein X is selected from oxygen atom and sulfur atom; wherein $R^{27}$ is selected from hydrido, alkyl, cycloalkyl, cycloalkylalkyl, aralkyl, aryl and $DR^{32}$ and

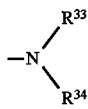

wherein D is selected from oxygen atom and sulfur atom; wherein $R^{32}$ is selected from hydrido, alkyl, cycloalkyl, cycloalkylalkyl, aratkyl and aryl;

wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

An even more preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkenyl, cycloalkenyl, alkynyl, mercaptocarbonyl, alkylsulfonyl, aralkylsulfonyl, arylsulfonyl and amido radicals of the formula

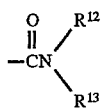

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, arylthio, aralkylthio, mercapto, alkylsulfinyl, alkylsulfonyl, aralkylsutfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

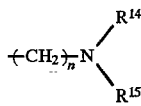

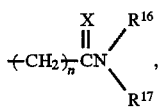

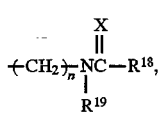

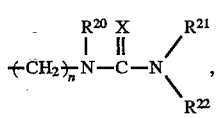

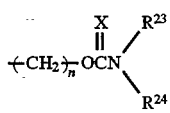

and

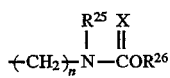

wherein X is selected from oxygen atom and sulfur atom; wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl; wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;

and wherein each of $R^0$ and $R^3$ through $R^{11}$ may be further independently selected from acidic moieties of the formula $$-Y_nA$$

wherein n is a number selected from zero through three, inclusive; wherein A is selected from carboxylic acid and bioisosteres of carboxylic acid selected from

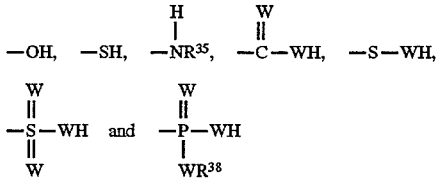

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$ and $R^{39}$ may be further independently selected from amino radical of the formula

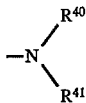

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups; wherein Y is a spacer group independently selected from one or more of alkyl, cycloalkyl, cycloalkylalkyl, alkenyl, aryl and aralkyl;

wherein each of $R^0$ through $R^{26}$, $R^{35}$ and $R^{38}$ through $R^{41}$, Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

A highly preferred class of compounds within Formula I consists of those compounds wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, cycloalkylcarbonyl, cycloalkylalkylcarbonyl, aralkylcarbonyl, alkenyl, alkynyl, alkylsulfonyl, aralkylsulfonyl, arylsulfonyl and amido radicals of the formula

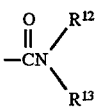

wherein each of $R^{12}$ and $R^{13}$ is independently selected from hydrido, alkyl, cycloalkyl, cyano, amino, hydroxyalkyl, alkoxyalkyl, phenalkyl and phenyl;

wherein each of $R^0$ and $R^2$ is independently selected from hydrido, alkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ and $R^2$ through $R^{11}$ may be further independently selected from amino and amido radicals of the formula

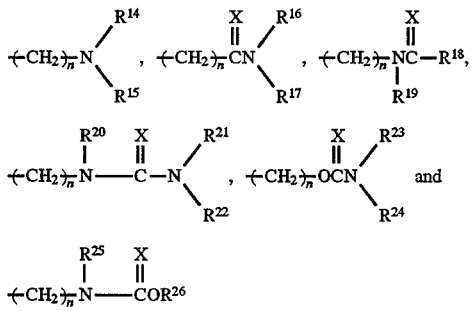

wherein X is selected from oxygen atom and sulfur atom; wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;

and wherein each of R⁰ and R³ through R¹¹ may be further independently selected from acidic moieties of the formula —Y$_n$A wherein n is a number selected from zero through two, inclusive; wherein A is selected from carboxylic acid and bioisosteres of carboxylic acid selected from

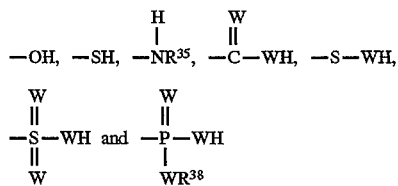

wherein each W is independently selected from oxygen atom, sulfur atom and NR³⁹; wherein each of R³⁵, R³⁸ and R³⁹ is independently selected from hydrido, alkyl, haloalkyl, haloalkylsulfonyl, haloalkylcarbonyl, cycloalkyl, phenyl and benzyl; wherein each of R³⁵ and R³⁹ may be further independently selected from amino radical of the formula

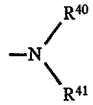

wherein each of R⁴⁰ and R⁴¹ is independently selected from hydrido, alkyl, cycloalkyl, hydroxyalkyl, haloalkyl, alkoxyalkyl, benzyl and phenyl; and the amide, ester and salt derivatives of said acidic groups;
wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from R³ through R¹¹ or may be attached at any two adjacent positions selected from R³ through R¹¹ so as to form a fused-ring system with one of the phenyl rings of Formula I; and the amide, ester and salt derivatives of said heterocyclic acidic groups;
wherein Y is a spacer group independently selected from one or more of alkyl, cycloalkyl, cycloalkylalkyl, alkenyl, phenyl, phenalkyl and aralkyl;
wherein each of R⁰ through R²⁶, R³⁵ and R³⁸ through R⁴¹, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;
or a tautomer thereof or a pharmaceutically-acceptable salt thereof.

An even more highly preferred class of compounds consists of those compounds of Formula I wherein m is one; wherein R¹ is selected from alkyl, hydroxyalkyl, haloalkyl, cycloalkyl, cycloalkylalkyl, aralkyl, aryl, benzoyl, alkoxyalkyl, alkylcarbonyl, alkoxycarbonyl, cycloalkylcarbonyl, cycloalkylalkylcarbonyl, aralkylcarbonyl, alkenyl and alkynyl;
where each of R⁰ and R² is independently selected from hydrido, alkyl, aminoalkyl, hydroxyalkyl, formyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and amino and amido radicals of the formula

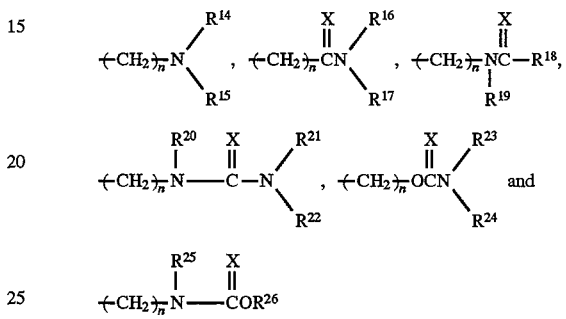

wherein X is selected from oxygen atom and sulfur atom;
wherein each n is a number independently selected from zero to six, inclusive;
wherein each of R¹⁴ through R²⁶ is independently selected from hydrido, alkyl, cycloalkyl, cyano, amino, hydroxyalkyl, alkoxyalkyl, phenalkyl and phenyl;
wherein each of R³ through R¹¹ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro, carboxyl, alkylthio and mercapto;
and wherein each of R⁰ and R³ through R¹¹ may be further independently selected from acidic moieties consisting of CO₂H, CO₂CH₃, SH, CH₂SH, C₂H₄SH, PO₃H₂, NHSO₂CF₃, NHSO₂C₆F₅, SO₃H, CONHNH₂, CONHNHSO₂CF₃, CONHOCH₃, CONHOC₂H₅, CONHCF₃, OH, CH₂OH, C₂H₄OH, OPO₃H₂, OSO₃H,

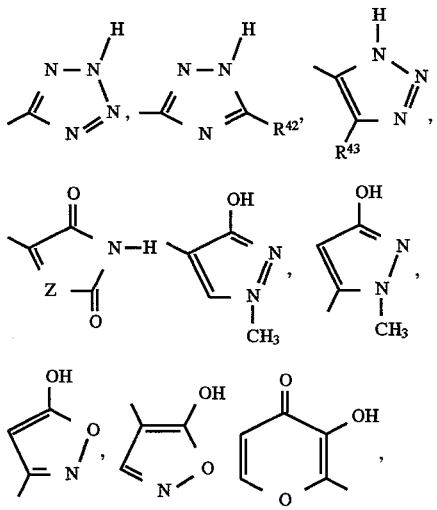

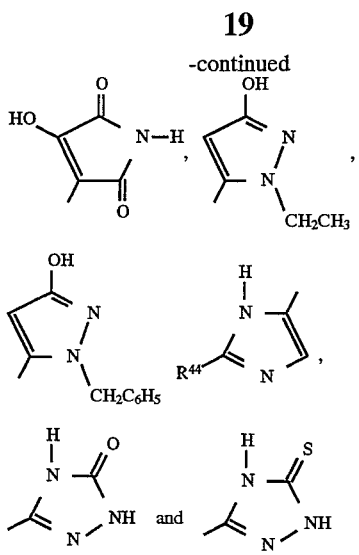

wherein each of $R^{42}$, $R^{43}$ and $R^{44}$ is independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CF_3$ and $SO_2C_6F_5$; wherein Z is selected from O, S, $NR^{45}$ and $CH_2$; wherein $R^{45}$ is selected from hydrido, $CH_3$ and $CH_2C_6H_5$; and wherein said acidic moiety may be a heterocyclic acidic group attached at any two adjacent positions of $R^3$ through $R^{11}$ so as to form a fused ring system with one of the phenyl rings of the biphenyl moiety of Formula I, said biphenyl fused ring system selected from

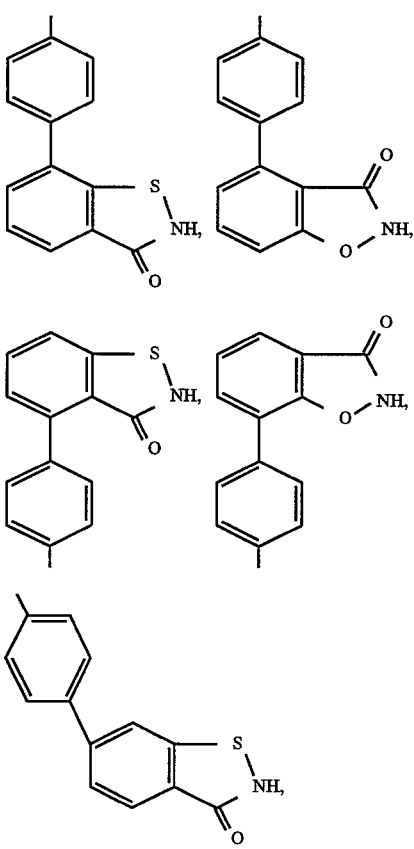

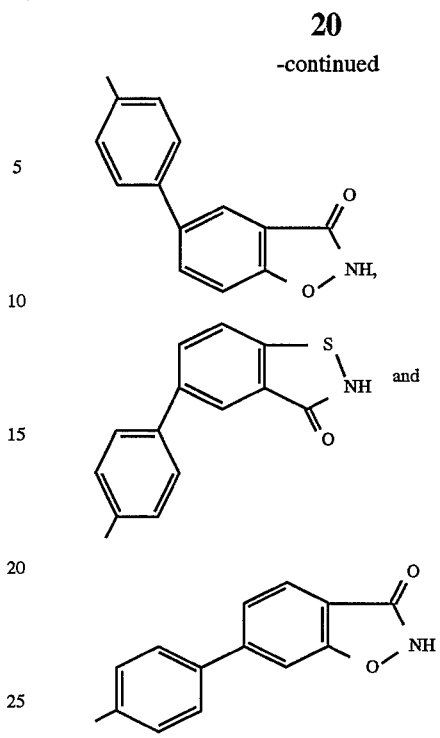

and the esters, amides and salts of said acidic moieties; or a tautomer thereof or a pharmaceutically-acceptable salt thereof.

A class of compounds of particular interest consists of those compounds of Formula I wherein m is one; wherein $R^1$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl; wherein $R^0$ is selected from hydrido, $C_4H_9(n)$, $CH_3CH_2CH=CH$, $C_3H_7(n)$, $SC_3H_7$,

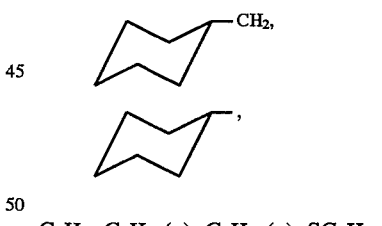

$C_2H_5$, $C_5H_{11}(n)$, $C_6H_{13}(n)$, $SC_4H_9$,

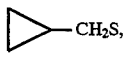

$CH_3CH=CH$, $CH_3CH_2CH_2CH=CH-$, amino, aminomethyl, aminoethyl, aminopropyl, $CH_2OH$, $CH_2OCOCH_3$, $CH_2Cl$, $CH_2OCH_3$, $CH_2OCH(CH_3)_2$, CHO, $CH_2CO_2H$, $CH(CH_3)CO_2H$, $NO_2$, Cl,

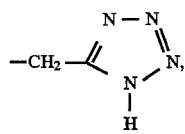

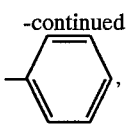

—CO₂CH₃, —CONH₂, —CONHCH₃, CON(CH₃)₂, —CH₂—NHCO₂C₂H₅,

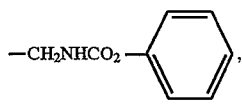

—CH₂NHCO₂CH₃, —CH₂NHCO₂C₃H₇, —CH₂NHCO₂CH₂(CH₃)₂, —CH₂NHCO₂C₄H₉, CH₂NHCO₂-adamantyl, —CH₂NHCO₂-(1-napthyl), —CH₂NHCONHCH₃, —CH₂NHCONHC₂H₅, —CH₂NHCONHC₃H₇, —CH₂NHCONHC₄H₉, —CH₂NHCONHCH(CH₃)₂, —CH₂NHCONH(1-napthyl), —CH₂NHCONH(1-adamantyl),

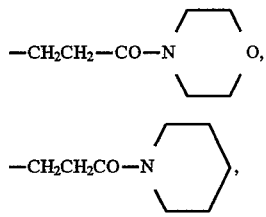

—CH₂CH₂CH₂CO₂H, —CH₂CH₂F, —CH₂OCONHCH₃, —CH₂OCSNHCH₃, —CH₂NHCSOC₃H₇, —CH₂CH₂CH₂F, —CH₂ONO₂,

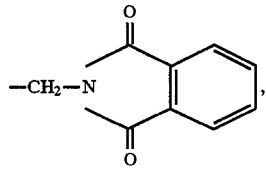

—CH₂SH,

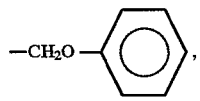

Cl, NO₂, CF₃, CH₂OH, Br, F, I, methyl, ethyl, n-propyl, isopropyl, n-butyl, sec-butyl, isobutyl, tert-butyl, n-pentyl, isopentyl, neopentyl, phenyl, cyclohexyl, cyclohexylmethyl, carboxyl, formyl, 1-oxoethyl, 1-oxopropyl, 1-oxobutyl, 1-oxopentyl, dimethoxymethyl, 1,1-dimethoxypropyl, 1,1-dimethoxypentyl, hydroxyalkyl, halo, 1-oxo-2-phenylethyl, 1-oxo-2-cyclohexylethyl, 1,1-difluoro-2-phenylethyl, monofluoromethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, difluoromethyl, CO₂H, SH, PO₃H₂, SO₃H, CONHNH₂, CONHNHSO₂CF₃, OH,

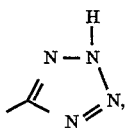

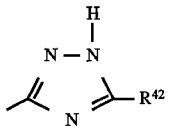

and

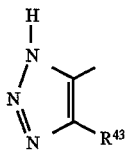

wherein each of R⁴² and R⁴³ is independently selected from chloro, cyano, nitro, trifluoromethyl, methoxycarbonyl and trifluoromethylsulfonyl; wherein R² is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hy, droxyalkyl; wherein each of R³ through R¹¹ is hydrido with the proviso that at least one of R⁵, R⁶, R⁸ and R⁹ is an acidic group selected from CO₂H, SH, PO₃H₂, SO₃H, CONHNH₂, CONHNHSO₂CF₃, OH,

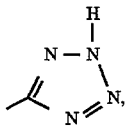

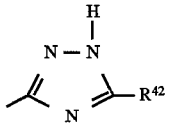

and

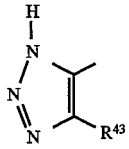

wherein each of R⁴² and R⁴³ is independently selected from chloro, cyano, nitro, trifluoromethyl, methoxycarbonyl and trifluoromethyl sul fonyl;

or a tautomer thereof or a pharmaceutically-acceptable salt thereof.

A class of compounds of more particular interest consists of those compounds of Formula I wherein m is one; wherein R¹ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butyny! and 2-hydroxybutyl; wherein R⁰ is selected from hydrido, methyl, ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2-cyclohexylethyl, 1,1-difluoro-2-phenylethyl, 1,1-diftuoro-2-cyclohexylethyl, 2-cyclohexylethyl, 1,1-difluoro-3-cyclohexylpropyl, fluoro, chloro, monofluoromethyl, difluoromethyl, trifluoromethyl, formyl, carboxyl, dimethoxymethyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, propylthio, butylthio, CO₂H, SH, PO₃H₂, SO₃H, CONHNH₂, CONHNHSO₂CF₃, OH,

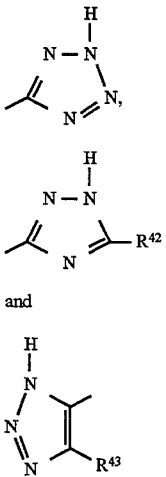

wherein each of $R^{42}$ and $R^{43}$ is independently selected from chloro, cyano, nitro, trifluoromethyl, methoxycarbonyl and trifluoromethylsulfonyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$ through $R^{11}$ is hydrido with the proviso that at least one of $R^5$, $R^6$, $R^8$ and $R^9$ is an acidic group selected from CO₂H, SH, PO₃H₂, SO₃H, CONHNH₂, CONHNHSO₂CF₃, OH,

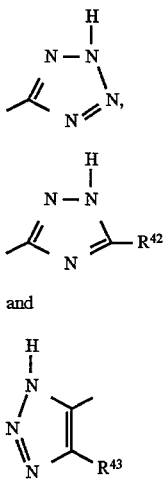

wherein each of $R^{42}$ and $R^{43}$ is independently selected from chloro, cyano, nitro, trifluoromethyl, methoxycarbonyl and trifluoromethylsulfonyl;
or a tautomer thereof or a pharmaceutically-acceptable salt thereof.

A class of compounds of even more particular interest consists of those compounds of Formula I wherein m is one; wherein $R^1$ is selected from methyl, ethyl, n-propyl, isopropyl, n-butyl, sec-butyl, isobutyl, tertbutyl, 4-methylbutyl, n-pentyl, neopentyl, phenyl, benzyl, phenethyl, cyclohexyl, cyclchexylmethyl, cyclohexylethyl cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, ethyl, n-propyl, isopropyl, n-butyl, sec-butyl, isobutyl, 4-methylbutyl, n-pentyl, 1-oxo-2-phenylethyl, 1-oxo-2-cyclohexylethyl, fluoro, chloro, monofluoromethyl, difluoromethyl, trifluoromethyl, formyl, carboxyl, dimethoxymethyl, 1,1-difluoro-2-phenylethyl, 1,1-difluoro-2-cyclohexylethyl, 2 cyclohexylethyl, 1,1-difluoro-3-cyclohexylpropyl, dimethoxymethyl, 1,1-dimethoxybutyt, 1,1-difluoroethyl, 1,1-difluoropropyl, 1,1-difluorobutyl, 1,1-difluoropentyl, benzyl, 2-phenylethyl, 1,1-difluoro-3-phenylprepyl, cyclohexylmethyl, cyclohexylethyl, cyclohexanoyl, 1-butenyl, 2-butenyl, 3-butenyl, 1-butynyl, 2-butynyl, 3-butynyl, propylthio and butylthio; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from COOH, SH, PO₃H₂, SO₃H, CONHNH₂, CONHNHSO₂CF₃, OH,

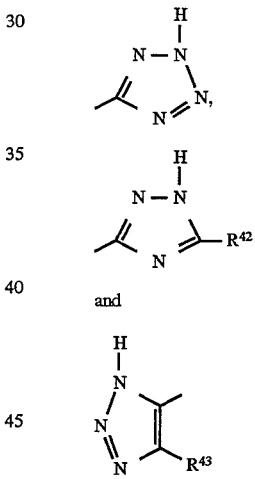

wherein each of $R^{42}$ and $R^{43}$ is independently selected from chloro, cyano, nitro, trifluoromethyl, methoxycarbonyl and trifluoromethylsulfonyl;
or a tautomer thereof or a pharmaceutically-acceptable salt thereof.

A class of compounds of even more particular interest consists of those compounds of Formula I wherein m is one; wherein $R^1$ is selected from methyl, ethyl, n-propyl, isopropyl, n-butyl, sec-butyl, isobutyl, tert-butyl, 4 methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxyethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl,, propylthio, butylthio, and hydroxyalkyl; wherein each of $R^3$, $R^4$, $R^6$, $R^7$, $R^8$, $R^{10}$ and $R^{11}$ is hydrido; with the proviso that at least one of $R^5$ and $R^9$ must be selected from COOH, SH, $PO_3H_2$, $SO_3H$, $CONHNH_2$, $CONHNHSO_2CF_3$, OH,

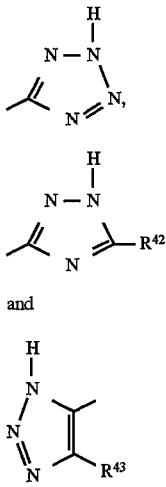

and wherein each of $R^{42}$ and $R^{43}$ is independently selected from chloro, cyano, nitro, trifluoromethyl, methoxycarbonyl and trifluoromethylsulfonyl;

or a tautomer thereof or a pharmaceutically-acceptable salt thereof.

A class of compounds of even greater particular interest consists of those compounds of Formula I wherein m is one; wherein $R^1$ is selected from methyl, ethyl, n propyl, isopropyl, n-butyl, sec-butyl, isobutyl, tert-butyl, 4 methylbutyl, n-pentyl, neopentyl, phenyl, benzyl, phenethyl, cyclohexyl, cyclohexylmethyl, cyclohexylethyl cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyt, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from $CO_2H$ and

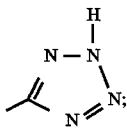

or a tautomer thereof or a pharmaceutically-acceptable salt thereof.

Within Formula I there is a sub-class of compounds of high interest as represented by Formula II:

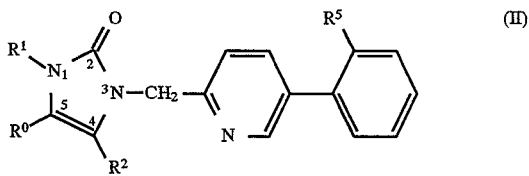

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

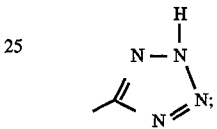

or a tautomer thereof or a pharmaceutically-acceptable salt thereof.

A family of specific compounds of particular interest within Formula II consists of compounds and pharmaceutically-acceptable salts thereof as follows:
1-methyl-4-propyl-1,3-dihydro-3-[[5-[2-(1H-tetrazol-5-yl)phenyl]-2-pyridinyl]methyl]-2H-imidazol-2-one;
1-ethyl-4-propyl-1,3-dihydro-3-[[5-[2-(1H-tetrazol-5-yl)phenyl]-2-pyridinyl]methyl]-2H-imidazol-2-one;
1,4-dipropyl-1,3-dihydro-3-[[5-[2-(1H-tetrazol-5-yl)phenyl]-2-pyridinyl]methyl]-2H-imidazol-2-one;
1-isopropyl-4-propyl-1,3-dihydro-3-[[5-[2-(1H-tetrazol-5-yl)phenyl]-2-pyridinyl]methyl]-2H-imidazol-2-one;
1-butyl-4-propyl-1,3-dihydro-3-[[5-[2-(1H-tetrazol-5-yl)phenyl]-2-pyridinyl]methyl]-2H-imidazol-2-one;
1-secbutyl-4-propyl-1,3-dihydro-3-[[5-[2-(1H-tetrazol-5-yl)phenyl]-2-pyridinyl]methyl]-2H-imidazol-2-one;
1-isobutyl-4-propyl-1,3-dihydro-3-[[5-[2-(1H-tetrazol-5-yl)phenyl]-2-pyridinyl]methyl]-2H-imidazol-2-one;
1-tertbutyl-4-propyl-1,3-dihydro-3-[[5-[2-(1H-tetrazol-5-yl)phenyl]-2-pyridinyl]methyl]-2H-imidazol-2-one;
1-pentyl-4-propyl-1,3-dihydro-3-[[5-[2-(1H-tetrazol-5-yl)phenyl]-2-pyridinyl]methyl]-2H-imidazol-2-one;
1-isopentyl-4-propyl-1,3-dihydro-3-[[5-[2-(1H-tetrazol-5-yl)phenyl]-2-pyridinyl]methyl]-2H-imidazol-2-one;
1-cyclohexyl-4-propyl-1,3-dihydro-3-[[5-[2-(1H-tetrazol-5-yl)phenyl]-2-pyridinyl]methyl]-2H-imidazol-2-one;
1-cyclohexylmethyl-4-propyl-1,3-dihydro-3-[[5-[2-(1H-tetrazol-5-yl)phenyl]-2-pyridinyl]methyl]-2H-imidazol-2-one;
1-phenyl-4-propyl-1,3-dihydro-3-[[5-[2-(1H-tetrazol-5-yl)phenyl]-2-pyridinyl]methyl]-2H-imidazol-2-one;
1-phenylmethyl-4-propyl-1,3-dihydro-3-[[5-[2-(1H-tetrazol-5-yl)phenyl]-2-pyridinyl]methyl]-2H-imidazol-2-one;
1-(2-cyclohexylethyl)-4-propyl-1,3-dihydro-3-[[5-[2-(1H-tetrazol-5-yl)phenyl]-2-pyridinyl]methyl]-2H-imidazol-2-one;

1-(2-phenylethyl)-4-propyl-1,3-dihydro-3-[[5-[2-(1H-tetrazol-5-yl)phenyl]-2-pyridinyl]methyl]-2H-imidazol-2-one;
1-methyl-4-butyl-1,3-dihydro-3-[[5-[2-(1H-tetrazol-5-yl)phenyl]-2-pyridinyl]methyl]-2H-imidazol-2-one;
1-ethyl-4-butyl-1,3-dihydro-3-[[5-[2-(1H-tetrazol-5-yl)phenyl]-2-pyridinyl]methyl]-2H-imidazol-2-one;
1-propyl-4-butyl-1,3-dihydro-3-[[5-[2-(1H-tetrazol-5-yl)phenyl]-2-pyridinyt]methyl]-2H-imidazol-2-one;
1-isopropyl-4-butyl-1,3-dihydro-3-[[5-[2-(1H-tetrazol-5-yl)phenyl]-2-pyridinyl]methyl]-2H-imidazol-2-one;
1,4-dibutyl-1,3-dihydro-3-[[5-[2-(1H-tetrazol-5-yl)phenyl]-2pyridinyl]methyl]-2H-imidazol-2-one;
1-secbutyl-4-butyl-1,3-dihydro-3-[[5-[2-(1H-tetrazol-5-yl)phenyl]-2-pyridinyl]methyl]-2H-imidazol-2-one;
1-isobutyl-4-butyl-1,3-dihydro-3-[[5-[2-(1H-tetrazol-5-yl)phenyl]-2-pyridinyl]methyl]-2H-imidazol-2-one;
1-tertbutyl-4-butyl-1,3-dihydro-3-[[5-[2-(1H-tetrazol-5-yl)phenyl]-2-pyridinyl]methyl]-2H-imidazol-2-one;
1-pentyl-4-butyl-1,3-dihydro-3-[[5-[2-(1H-tetrazol-5-yl)phenyl]-2-pyridinyl]methyl]-2H-imidazol-2-one;
1-isopentyl-4-butyl-1,3-dihydro-3-[[5-[2-(1H-tetrazol-5-yl)phenyl]-2-pyridinyl]methyl]-2H-imidazol-2-one;
1-cyclohexyl-4-butyl-1,3-dihydro-3-[[5-[2-(1H-tetrazol-5-yl)phenyl]-2-pyridinyl]methyl]-2H-imidazol-2-one;
1-cyclohexylmethyl-4-butyl-1,3-dihydro-3-[[5-[2-(1H-tetrazol-5-yl)phenyl]-2-pyridinyl]methyl]-2H-imidazol-2-one;
1-phenyl-4-butyl-1,3-dihydro-3-[[5-[2-(1H-tetrazol-5-yl)phenyl]-2-pyridinyl]methyl]-2H-imidazol-2-one;
1-phenylmethyl-4-butyl-1,3-dihydro-3-[[5-[2-(1H-tetrazol-5-yl)phenyl]-2-pyridinyl]methyl]-2H-imidazol-2-one;
1-(2-cyclohexylethyl)-4-butyl-1,3-dihydro-3-[[5-[2-(1H-tetrazol-5-yl)phenyl]-2-pyridinyl]methyl]-2H-imidazol-2-one;
1-(2-phenylethyl)-4-butyl-1,3-dihydro-3-[[5-[2-(1H-tetrazol-5-yl)phenyl]-2-pyridinyl]methyl]-2H-imidazol-2-one;
1-methyl-4-pentyl-1,3-dihydro-3-[[5-[2-(1H-tetrazol-5-yl)phenyl]-2-pyridinyl]methyl]-2H-imidazol-2-one;
1-ethyl-4-pentyl-1,3-dihydro-3-[[5-[2-(1H-tetrazol-5-yl)phenyl]-2-pyridinyl]methyl]-2H-imidazol-2-one;
1-propyl-4-pentyl-1,3-dihydro-3-[[5-[2-(1H-tetrazol-5-yl)phenyl]-2-pyridinyl]methyl]-2H-imidazol-2-one;
1-isopropyl-4-pentyl-1,3-dihydro-3-[[5-[2-(1H-tetrazol-5-yl)phenyl]-2-pyridinyl]methyl]-2H-imidazol-2-one;
1-butyl-4-pentyl-1,3-dihydro-3-[[5-[2-(1H-tetrazol-5-yl)phenyl]-2-pyridinyl]methyl]-2H-imidazol-2-one;
1-secbutyl-4-pentyl-1,3-dihydro-3-[[5-[2-(1H-tetrazol-5-yl)phenyl]-2-pyridinyl]methyl]-2H-imidazol-2-one;
1-isobutyl-4-pentyl-1,3-dihydro-3-[[5-[2-(1H-tetrazol-5-yl)phenyl]-2-pyridinyl]methyl]-2H-imidazol-2-one;
1-tertbutyl-4-pentyl-1,3-dihydro-3-[[5-[2-(1H-tetrazol-5-yl)phenyl]-2-pyridinyl]methyl]-2H-imidazol-2-one;
1,4-dipentyl-1,3-dihydro-3-[[5-[2-(1H-tetrazol-5-yl)phenyl]-2-pyridinyl]methyl]-2H-imidazol-2-one;
1-isopentyl-4-pentyl-1,3-dihydro-3-[[5-[2-(1H-tetrazol-5-yl)phenyl]-2-pyridinyl]methyl]-2H-imidazol-2-one;
1-cyclohexyl-4-pentyl-1,3-dihydro-3-[[5-[2-(1H-tetrazol-5-yl)phenyl]-2-pyridinyl]methyl]-2H-imidazol-2-one;
1-cyclohexylmethyl-4-pentyl-1,3-dihydro-3-[[5-[2-(1H-tetrazol-5-yl)phenyl]-2-pyridinyl]methyl]-2H-imidazol-2-one;
1,4-dipentyl-1,3-dihydro-3-[[5-[2-(1H-tetrazol-5-yl)phenyl]-2-pyridinyl]methyl]-2H-imidazol-2-one;
1-phenylmethyl-4-pentyl-1,3-dihydro-3-[[5-[2-(1H-tetrazol-5-yl)phenyl]-2-pyridinyl]methyl]-2H-imidazol-2-one;
1-(2-cyclohexylethyl)-4-pentyl-1,3-dihydro-3-[[5-[2-(1H-tetrazol-5-yl)phenyl]-2-pyridinyl]methyl]-2H-imidazol-2-one;
1-(2-phenylethyl)-4-pentyl-1,3-dihydro-3-[[5-[2-(1H-tetrazol-5-yl)phenyl]-2-pyridinyl]methyl]-2H-imidazol-2-one;
1,5-dimethyl-4-propyl-1,3-dihydro-3-[[5-[2-(1H-tetrazol-5-yl)phenyl]-2-pyridinyl]methyl]-2H-imidazol-2-one;
1-ethyl-4-propyl-5-methyl-1,3-dihydro-3-[[5-[2-(1H-tetrazol-5-yl)phenyl]-2-pyridinyl]methyl]-2H-imidazol-2-one;
1,4-dipropyl-5-methyl-1,3-dihydro-3-[[5-[2-(1H-tetrazol-5-yl)phenyl]-2-pyridinyl]methyl]-2H-imidazol-2-one;
1-isopropyl-4-propyl-5-methyl-1,3-dihydro-3-[[5-[2-(1H-tetrazol-5-yl)phenyl]-2-pyridinyl]methyl]-2H-imidazol-2-one;
1-butyl-4-propyl-5-methyl-1,3-dihydro-3-[[5-[2-(1H-tetrazol-5-yl)phenyl]-2-pyridinyl]methyl]-2H-imidazol-2-one;
1-secbutyl-4-propyl-5-methyl-1,3-dihydro-3-[[5-[2-(1H-tetrazol-5-yl)phenyl]-2-pyridinyl]methyl]-2H-imidazol-2-one;
1-isobutyl-4-propyl-5-methyl-1,3-dihydro-3-[[5-[2-(1H-tetrazol-5-yl) phenyl]-2-pyridinyl]methyl]-2H-imidazol-2-one;
1-tertbutyl-4-propyl-5-methyl-1,3-dihydro-3-[[5-[2-(1H-tetrazol-5-yl)phenyl]-2-pyridinyl]methyl]-2H-imidazol-2-one 1-pentyl-4-propyl-5-methyl-1,3-dihydro-3-[[5-[2-(1H-tetrazol-5-yl)phenyl]-2-pyridinyl]methyl]-2H-imidazol-2-one;
1-isopentyl-4-propyl-5-methyl-1,3-dihydro-3-[[5-[2-(1H-tetrazol-5-yl)phenyl]-2-pyridinyl]methyl]-2H-imidazol-2-one;
1-cyclohexyl-4-propyl-5-methyl-1,3-dihydro-3-[[5-[2-(1H-tetrazol-5-yl)phenyl]-2-pyridinyl]methyl]-2H-imidazol-2-one;
1-cyclohexylmethyl-4-propyl-5-methyl-1,3-dihydro-3-[[5-[2-(1H-tetrazol-5-yl)phenyl-2-pyridinyl]methyl]-2H-imidazol-2-one;
1-phenyl-4-propyl-5-methyl-1,3-dihydro-3-[[5-[2-(1H-tetrazol-5-yl)phenyl]-2-pyridinyl]methyl]-2H-imidazol-2-one;
1-phenylmethyl-4-propyl-5-methyl-1,3-dihydro-3-[[5-[2-(1H-tetrazol-5-yl)phenyl]-2-pyridinyl]methyl]-2H-imidazol-2-one;
1-(2-cyclohexylethyl)-4-propyl-5-methyl-1,3-dihydro-3-[[5-[2-(1H-tetrazol-5-yl)phenyl]-2-pyridinyl]methyl]-2H-imidazol-2-one;
1-(2-phenylethyl)-4-propyl-5-methyl-1,3-dihydro-3-[[5-[2-(1H-tetrazol-5-yl)phenyl]-2-pyridinyl]methyl]-2H-imidazol-2-one;
1,5-dimethyl-4-butyl-1,3-dihydro-3-[[5-[2-(1H-tetrazol-5-yl)phenyl]-2-pyridinyl]methyl]-2H-imidazol-2-one;
1-ethyl-4-butyl-5-methyl-1,3-dihydro-3-[[5-[2-(1H-tetrazol-5-yl)phenyl]-2-pyridinyl]methyl]-2H-imidazol-2-one;
1-propyl-4-butyl-5-methyl-1,3-dihydro-3-[[5-[2-(1H-tetrazol-5-yl)phenyl]-2-pyridinyl]methyl]-2H-imidazol-2-one;
1-isopropyl-4-butyl-5-methyl-1,3-dihydro-3-[[5-[2-(1H-tetrazol-5-yl)phenyl]-2-pyridinyl]methyl]-2H-imidazol-2-one;
1,4-dibutyl-5-methyl-1,3-dihydro-3-[[5-[2-(1H-tetrazol-5-yl)phenyl]-2-pyridinyl]methyl]-2H-imidazol-2-one;
1-secbutyl-4-butyl-5-methyl-1,3-dihydro-3-[[5-[2-(1H-tetrazol-5-yl)phenyl]-2-pyridinyl]methyl]-2H-imidazol-2-one;

1-isobutyl-4-butyl-5-methyl-1,3-dihydro-3-[[5-[2-(1H-tetrazol-5-yl)phenyl]-2-pyridinyl]methyl]-2H-imidazol-2-one;

1-tertbutyl-4-butyl-5-methyl-1,3-dihydro-3-[[5-[2-(1H-tetrazol-5-yl)phenyl]-2-pyridinyl]methyl]-2H-imidazol-2-one;

1-pentyl-4-butyl-5-methyl-1,3-dihydro-3-[[5-[2-(1H-tetrazol-5-yl)phenyl]-2-pyridinyl]methyl]-2H-imidazol-2-one;

1-isopentyl-4-butyl-5-methyl-1,3-dihydro-3-[[5-[2-(1H-tetrazol-5-yl)phenyl]-2-pyridinyl]methyl]-2H-imidazol-2-one;

1-cyclohexyl-4-butyl-5-methyl-1,3-dihydro-3-[[5-[2-(1H-tetrazol-5-yl)phenyl]-2-pyridinyl]methyl]-2H-imidazol-2-one;

1-cyclohexylmethyl-4-butyl-5-methyl-1,3-dihydro-3-[[5-[2-(1H-tetrazol-5-yl)phenyl]-2-pyridinyl]methyl]-2H-imidazol-2-one;

1-phenyl-4-butyl-5-methyl-1,3-dihydro-3-[[5-[2-(1H-tetrazol-5-yl)phenyl]-2-pyridinyl]methyl]-2H-imidazol-2-one;

1-phenylmethyl-4-butyl-5-methyl-1,3-dihydro-3-[[5-[2-(1H-tetrazol-5-yl)phenyl]-2-pyridinyl]methyl]-2H-imidazol-2-one;

1-(2-cyclohexylethyl)-4-butyl-5-methyl-1,3-dihydro-3-[[5-[2-(1H-tetrazol-5-yl)phenyl]-2-pyridinyl]methyl]-2H-imidazol-2-one;

1-(2-phenylethyl)-4-butyl-5-methyl-1,3-dihydro-3-[[5-[2-(1H-tetrazol-5-yl)phenyl]-2-pyridinyl]methyl]-2H-imidazol-2-one;

1,5-dimethyl-4-pentyl-1,3-dihydro-3-[[5-[2-(1H-tetrazol-5-yl)phenyl]-2-pyridinyl]methyl]-2H-imidazol-2-one;

1-ethyl-4-pentyl-5-methyl-1,3-dihydro-3-[[5-[2-(1H-tetrazol-5-yl)phenyl]-2-pyridinyl]methyl]-2H-imidazol-2-one;

1-propyl-4-pentyl-5-methyl-1,3-dihydro-3-[[5-[2-(1H-tetrazol-5-yl)phenyl]-2-pyridinyl]methyl]-2H-imidazol-2-one;

1-isopropyl-4-pentyl-5-methyl-1,3-dihydro-3-[[5-[2-(1H-tetrazol-5-yl)phenyl]-2-pyridinyl]methyl]-2H-imidazol-2-one;

1-butyl-4-pentyl-5-methyl-1,3-dihydro-3-[[5-[2-(1H-tetrazol-5-yl)phenyl]-2-pyridinyl]methyl]-2H-imidazol-2-one;

1-secbutyl-4-pentyl-5-methyl-1,3-dihydro-3-[[3-[2-(1H-tetrazol-5-yl)phenyl]-2-pyridinyl]methyl]-2H-imidazol-2-one;

1-isobutyl-4-pentyl-5-methyl-1,3-dihydro-3-[[5-[2-(1H-tetrazol-5-yl)phenyl]-2-pyridinyl]methyl]-2H-imidazol-2-one;

1-tertbutyl-4-pentyl-5-methyl-1,3-dihydro-3-[[5-[2-(1H-tetrazol-5-yl)phenyl]-2-pyridinyl]methyl]-2H-imidazol-2-one;

1-phenyl-4-pentyl-5-methyl-1,3-dihydro-3-[[5-[2-(1H-tetrazol-5-yl)phenyl]-2-pyridinyl]methyl]-2H-imidazol-2-one;

1-isopentyl-4-pentyl-5-methyl-1,3-dihydro-3-[[5-[2-(1H-tetrazol-5-yl)phenyl]-2-pyridinyl]methyl]-2H-imidazol-2-one;

1-cyclohexyl-4-pentyl-5-methyl-1,3-dihydro-3-[[5-[2-(1H-tetrazol-5-yl)phenyl]-2-pyridinyl]methyl]-2H-imidazol-2-one;

1-cyclohexylmethyl-4-pentyl-5-methyl-1,3-dihydro-3-[[5-[2-(1H-tetrazol-5-yl)phenyl]-2-pyridinyl]methyl]-2H-imidazol-2-one;

1,4-dipentyl-5-methyl-1,3-dihydro-3-[[5-[2-(1H-tetrazol-5-yl)phenyl]-2-pyridinyl]methyl]-2H-imidazol-2-one;

1-phenylmethyl-4-pentyl-5-methyl-1,3-dihydro-3-[[5-[2-(1H-tetrazol-5-yl)phenyl]-2-pyridinyl]methyl]-2H-imidazoi-2-one;

1-(2-cyclohexylethyl)-4-pentyl-5-methyl-1,3-dihydro-3-[[5-[2-(1H-tetrazol-5-yl) -yl)phenyl]-2-pyridinyl]methyl]-2H-imidazol-2-one;

1-(2-phenylethyl)-4-pentyl-5-methyl-1,3-dihydro-3-[[5-[2-(1H-tetrazol-5-yl) -yl)phenyl]-2-pyridinyl]methyl]-2H-imidazol-2-one;

1-methyl-4-propyl-5-chloro-1,3-dihydro-3-[[5-[2-(1H-tetrazol-5-yl)phenyl]-2-pyridinyl]methyl]-2H-imidazol-2-one;

1-ethyl-4 -propyl-5-chloro-1,3-dihydro-3-[[5-[2-(1H-tetrazol-5-yl)phenyl]-2-pyridinyl]methyl]-2H-imidazol-2-one;

1,4-dipropyl-5-chloro-1,3-dihydro-3-[[5-[2-(1H-tetrazol-5-yl)phenyl]-2-pyridinyl]methyl]-2H-imidazol-2-one;

1-isopropyl-4-propyl-5-chloro-1,3-dihydro-3-[[5-[2-(1H-tetrazol-5-yl)phenyl]-2-pyridinyl]methyl]-2H-imidazol-2-one;

1-butyl-4-propyl-5-chloro-1,3-dihydro-3-[[5-[2-(1H-tetrazol-5-yl)phenyl]-2-pyridinyl]methyl]-2H-imidazol-2-one;

1-secbutyl-4-propyl-5-chloro-1,3-dihydro-3-[[5-[2-(1H-tetrazol-5-yl)phenyl]-2-pyridinyl]methyl]-2H-imidazol-2-one;

1-isobutyl-4-propyl-5-chloro-1,3-dihydro-3-[[5-[2-(1H-tetrazol-5-yl)phenyl]-2-pyridinyl]methyl]-2H-imidazol-2-one;

1-tertbutyl-4-propyl-5-chloro-1,3-dihydro-3-[[5-[2-(1H-tetrazol-5-yl)phenyl]-2-pyridinyl]methyl]-2H-imidazol-2-one;

1-pentyl-4-propyl-5-chloro-1,3-dihydro-3-[[5-[2-(1H-tetrazol-5-yl)phenyl]-2-pyridinyl]methyl]-2H-imidazol-2-one;

1-isopentyl-4-propyl-5-chloro-1,3-dihydro-3-[[5-[2-(1H-tetrazol-5-yl)phenyl]-2-pyridinyl]methyl]-2H-imidazol-2-one;

1-cyclohexyl-4-propyl-5-chloro-1,3-dihydro-3-[[5-[2-(1H-tetrazol-5-yl)phenyl]-2-pyridinyl]methyl]-2H-imidazol-2-one;

1-cyclohexylmethyl-4-propyl-5-chloro-1,3-dihydro-3-[[5-[2-(1H-tetrazol-5-yl) -yl)phenyl]-2-pyridinyl]methyl]-2H-imidazol-2-one;

1-phenyl-4-propyl-5-chloro-1,3-dihydro-3-[[5-[2-(1H-tetrazol-5-yl)phenyl]-2-pyridinyl]methyl]-2H-imidazol-2-one;

1-phenylmethyl-4-propyl-5-chloro-1,3-dihydro-3-[[5-[2-(1H-tetrazol-5-yl)phenyl]-2-pyridinyl]methyl]-2H-imidazol-2-one;

1-(2-cyclohexylethyl)-4-propyl-5-chloro-1,3-dihydro-3-[[5-[2-(1H-tetrazol-5-yl) -yl)phenyl]-2-pyridinyl]methyl]-2H-imidazol-2-one;

1-(2-phenylethyl)-4-propyl-5-chloro-1,3-dihydro-3-[[5-[2-(1H-tetrazol-5-yl) -yl)phenyl]-2-pyridinyl]methyl]-2H-imidazol-2-one;

1-methyl-4-butyl-5-chloro-1,3-dihydro-3-[[5-[2-(1H-tetrazol-5-yl)phenyl]-2-pyridinyl]methyl]-2H-imidazol-2-one;

1-ethyl-4-butyl-5-chloro-1,3-dihydro-3-[[5-[2-(1H-tetrazol-5-yl)phenyl]-2-pyridinyl]methyl]-2H-imidazol-2-one;

1-propyl-4-butyl-5-chloro-1,3-dihydro-3-[[5-[-(1H-tetrazol-5-yl)phenyl]-2-pyridinyl]methyl]-2H-imidazol-2-one;

1-isopropyl-4-butyl-5-chloro-1,3-dihydro-3-[[5-[2-(1H-tetrazol-5-yl)phenyl]-2-pyridinyl]methyl]-2H-imidazol-2-one;

1,4-dibutyl-5-chloro-1,3-dihydro-3-[[5-[2-(1H-tetrazol-5-yl)phenyl]-2-pyridinyl]methyl]-2H-imidazol-2-one;

1-secbutyl-4-butyl-5-chloro-1,3-dihydro-3-[[5-[2-(1H-tetrazol-5-yl)phenyl]-2-pyridinyl]methyl]-2H-imidazol-2-one;

1-isobutyl-4-butyl-5-chloro-1,3-dihydro-3-[[5-[2-(1H-tetrazol-5-yl)phenyl]-2-pyridinyl]methyl]-2H-imidazol-2-one;

1-tertbutyl-4-butyl-5-chloro-1,3-dihydro-3-[[5-[2-(1H-tetrazol-5-yl)phenyl]-2-pyridinyl]methyl]-2H-imidazol-2-one;

1-pentyl-4-butyl-5-chloro-1,3-dihydro-3-[[5-[2-(1H-tetrazol-5-yl)phenyl]-2-pyridinyl]methyl]-2H-imidazol-2-one;

1-isopentyl-4-butyl-5-chloro-1,3-dihydro-3-[[5-[2-(1H-tetrazol-5-yl)phenyl]-2-pyridinyl]methyl]-2H-imidazol-2-one;

1-cyclohexyl-4-butyl-5-chloro-1,3-dihydro-3-[[5-[2-(1H-tetrazol-5-yl)phenyl]-2-pyridinyl]methyl]-2H-imidazol-2-one;

1-cyclohexylmethyl-4-butyl-5-chloro-1,3-dihydro-3-[[5-[2-(1H-tetrazol-5-yl) -yl)phenyl]-2-pyridinyl]methyl]-2H-imidazol-2-one;

1-phenyl-4-butyl-5-chloro-1,3-dihydro-3-[[5-[2-(1H-tetrazol-5-yl)phenyl]-2-pyridinyl]methyl]-2H-imidazol-2-one;

1-phenylmethyl-4-butyl-5-chloro-1,3-dihydro-3-[[5-[2-(1H-tetrazol-5-yl)phenyl]-2-pyridinyl]methyl]-2H-imidazol-2-one;

1-(2-cyclohexylethyl)-4-butyl-5-chloro-1,3-dihydro-3-[[5-[2-(1H-tetrazol-5-yl) -yl)phenyl]-2-pyridinyl]methyl]-2H-imidazol-2-one;

1-(2-phenylethyl)-4-butyl-5-chloro-1,3-dihydro-3-[[5-[2-(1H-tetrazol-5-yl) -yl)phenyl]-2-pyridinyl]methyl]-2H-imidazol-2-one;

1-methyl-4-pentyl-5-chloro-1,3-dihydro-3-[[5-[2-(1H-tetrazol-5-yl)phenyl]-2-pyridinyl]methyl]-2H-imidazol-2-one;

1-ethyl-4-pentyl-5-chloro-1,3-dihydro-3-[[5-[2-(1H-tetrazol-5-yl)phenyl]-2-pyridinyl]methyl]-2H-imidazol-2-one;

1-propyl-4-pentyl-5-chloro-1,3-dihydro-3-[[5-[2-(1H-tetrazol-5-yl)phenyl]-2-pyridinyl]methyl]-2H-imidazol-2-one;

1-isopropyl-4-pentyl-5-chloro-1,3-dihydro-3-[[5-[2-(1H-tetrazol-5-yl)phenyl]-2-pyridinyl]methyl]-2H-imidazol-2-one;

1-butyl-4-pentyl-5-chloro-1,3-dihydro-3-[[5-[2-(1H-tetrazol-5-yl)phenyl]-2-pyridinyl]methyl]-2H-imidazol-2-one;

1-secbutyl-4-pentyl-5-chloro-1,3-dihydro-3-[[5-[2-(1H-tetrazol-5-yl)phenyl]-2-pyridinyl]methyl]-2H-imidazol-2-one;

1-isobutyl-4-pentyl-5-chloro-1,3-dihydro-3-[[5-[2-(1H-tetrazol-5-yl)phenyl]-2-pyridinyl]methyl]-2H-imidazol-2-one;

1-tertbutyl-4-pentyl-5-chloro-1,3-dihydro-3-[[5-[2-(1H-tetrazol-5-yl)phenyl]-2-pyridinyl]methyl]-2H-imidazol-2-one;

1,4-dipentyl-5-chloro-1,3-dihydro-3-[[5-[2-(1H-tetrazol-5-yl)phenyl]-2-pyridinyl]methyl]-2H-imidazol-2-one;

1-isopentyl-4-pentyl-5-chloro-1,3-dihydro-3-[[5-[2-(1H-tetrazol-5-yl)phenyl]-2-pyridinyl]methyl]-2H-imidazol-2-one;

1-cyclohexyl-4-pentyl-5-chloro-1,3-dihydro-3-[[6-[2-(1H-tetrazol-5-yl)phenyl]-2-pyridinyl]methyl]-2H-imidazol-2-one;

1-cyclohexylmethyl-4-pentyl-5-chloro-1,3-dihydro-3-[[5-[2-(1H-tetrazol-5-yl) -yl)phenyl]-2-pyridinyl]methyl]-2H-imidazol-2-one;

1-phenyl-4-pentyl-5-chloro-1,3-dihydro-3-[[5-[2-(1H-tetrazol-5-yl)phenyl]-2-pyridinyl]methyl]-2H-imidazol-2-one;

1-phenylmethyl4-pentyl-5-chloro-1,3-dihydro-3-[[5-[2-(1H-tetrazol-5-yl)phenyl]-2-pyridinyl]methyl]-2H-imidazol-2-one;

1-(2-cyclohexylethyl)-4-pentyl-5-chloro-1,3-dihydro-3-[[5-[2-(1H-tetrazol-5-yl) -yl)phenyl]-2-pyridinyl]methyl]-2H-imidazol-2-one;

and 1-(2-phenylethyl)-4-pentyl-5-chloro-1,3-dihydro-3-[[5-[2-(1H-tetrazol-5-yl) -yl)phenyl]-2-pyridinyl]methyl]-2H-imidazol-2-one.

A family of specific compounds of more particular interest within Formula II consists of compounds and pharmaceutically-acceptable salts thereof as follows:

1-propyl-4-butyl-1,3-dihydro-3-[[5-[2-(1H-tetrazol-5-yl)phenyl]-2-pyridinyl]methyl]-2H-imidazol-2-one;

1,4-dibutyl-1,3-dihydro-3-[[5-[2-(1H-tetrazol-5phenyl]2-pyridinyl]methyl]-2H-imidazol-2-one;

1-pentyl-4-butyl-1,3-dihydro-3-[[5-[2-(1H-tetrazol-5-yl)phenyl]-2-pyridinyl]methyl]-2H-imidazol-2-one;

1-isopentyl-4-butyl-1,3-dihydro-3-[[5-[2-(1H-tetrazol-5-yl)phenyl]-2-pyridinyl]methyl]-2H-imidazol-2-one;

1-cyclohexylmethyl-4-butyl-1,3-dihydro-3-[[5-[2-(1H-tetrazol-5-yl)phenyl]-2-pyridinyl]methyl]-2H-imidazol-2-one;

1-phenylmethyl-4-butyl-1,3-dihydro-3-[[5-[2-(1H-tetrazot-5-yl)phenyl]-2-pyridinyl]methyl]-2H-imidazol-2-one;

1-(2-cyclohexylethyl)-4-butyl-1,3-dihydro-3-[[5-[2-(1H-tetrazol-5-yl)phenyl]-2-pyridinyl]methyl]-2H-imidazol-2-one;

1-(2-phenylethyl)-4-butyl-1,3-dihydro-3-[[5-[2-(1H-tetrazol-5-yl)phenyl]-2-pyridinyl]methyl]-2H-imidazol-2-one;

1-propyl-4-butyl-5-methyl-1,3-dihydro-3-[[5-[2-(1H-tetrazol-5-yl)phenyl]-2-pyridinyl]methyl]-2H-imidazol-2-one;

1,4-dibutyl-5-methyl-1,3-dihydro-3-[[5-[2-(1H-tetrazol-5-yl)phenyl]-2-pyridinyl]1-pentyl-4-butyl-5-methyl-1,3-dihydro-3-[[5-[2-(1H-tetrazol-5-yl)phenyl]-2-pyridinyl]methyl]-2H-imidazol-2-one;

1-isopentyl-4-butyl-5-methyl-1,3-dihydro-3-[[5-[2-(1H-tetrazol-5-yl)phenyl]-2-pyridinyl]methyl]-2H-imidazol-2-one;

1-cyclohexylmethyl-4-butyl-5-methyl-1,3-dihydro-3-[[5-[2-(1H-tetrazol-5-yl) -yl)phenyl]-2-pyridinyl]methyl]-2H-imidazol-2-one;

1-phenylmethyl-4-butyl-5-methyl-1,3-dihydro-3-[[5-[2-(1H-tetrazol-5-yl) -yl)phenyl]-2-pyridinyl]methyl]-2H-imidazol-2-one;

1-(2-cyclohexylethyl)-4-butyl-5-methyl-1,3-dihydro-3-[[5-[2-(1H-tetrazol-5-yl) -yl)phenyl]-2-pyridinyl]methyl]-2H-imidazol-2-one;

1-(2-phenylethyl)-4-butyl-5-methyl-1,3-dihydro-3-[[5-[2-(1H-tetrazol-5-yl) -yl)phenyl]-2-pyridinyl]methyl]-2H-imidazol-2-one;

1-propyl-4-butyl-5-chloro-1,3-dihydro-3-[[5-[2-(1H-tetrazol-5-yl)phenyl]-2-pyridinyl]methyl]-2H-imidazol-2-one;

1,4-dibutyl-5-chloro-1,3-dihydro-3-[[5-[2-(1H-tetrazol-5-yl)phenyl]-2-pyridinyl]methyl]-2H-imidazol-2-one;

1-pentyl-4-butyl-5-chloro-1,3-dihydro-3-[[5-[2-(1H-tetrazol-5-yl) -yl)phenyl]-2-pyridinyl]methyl]-2H-imidazol-2-one;

1-isopentyl-4-butyl-5-chloro-1,3-dihydro-3-[[5-[2-(1H-tetrazol-5-yl)phenyl]-2-pyridinyl]methyl]-2H-imidazol-2-one;

1-cyclohexylmethyl-4-butyl-5-chloro-1,3-dihydro-3-[[5-[2-(1H-tetrazol-5-yl) -yl)phenyl]-2-pyridinyl]methyl]-2H-imidazol-2-one;

1-phenylmethyl-4-butyl-5-chloro-1,3-dihydro-3-[[5-[2-(1H-tetrazol-5-yl)phenyl]-2-pyridinyl]methyl]-2H-imidazol-2-one;

1-(2-cyclohexylethyl)-4-butyl-5-chloro-1,3-dihydro-3-[[5-[2-(1H-tetrazol-5-yl) -yl)phenyl]-2-pyridinyl]methyl]-2H-imidazol-2-one;

and 1-(2-phenylethyl)-4-butyl-5-chloro-1,3-dihydro-3-[[5-[2-(1H-tetrazol-5-yl) -yl)phenyl]-2-pyridinyl]methyl]-2H-imidazol-2-one.

Within Formula I there is second sub-class of compounds of high interest as represented by Formula III:

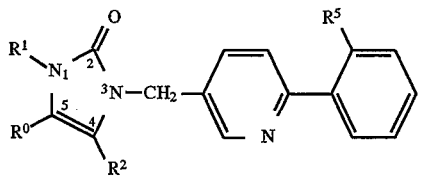

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyt; wherein $R^5$ is an acidic group selected from $CO_2H$ and

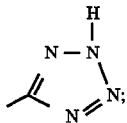

or a tautomer thereof or a pharmaceutically-acceptable salt thereof.

A family of specific compounds of particular interest within Formula III consists of compounds and pharmaceutically-acceptable salts thereof as follows:

1-methyl-4-propyl-1,3-dihydro-3-[[6-[2-(1H-tetrazol-5-yl)phenyl]-3-pyridinyl]methyl]-2H-imidazol-2-one;

1-ethyl-4-propyl-1,3-dihydro-3-[[6-[2-(1H-tetrazol-5-yl)phenyl]-3-pyridinyl]methyl]-2H-imidazol-2-one;

1,4-dipropyl-1,3-dihydro-3-[[6-[2-(1H-tetrazol-5-yl)phenyl]-3-pyridinyl]methyl]-2H-imidazol-2-one;

1-isopropyl-4-propyl-1,3-dihydro-3-[[6-[2-(1H-tetrazol-5-yl)phenyl]-3-pyridinyl]methyl]-2H-imidazol-2-one;

1-butyl-4-propyl-1,3-dihydro-3-[[6-[2-(1H-tetrazol-5-yl)phenyl]-3-pyridinyl]methyl]-2H-imidazol-2-one;

1-secbutyl-4-propyl-1,3-dihydro-3-[[6-[2-(1H-tetrazol-5-yl)phenyl]-3-pyridinyl]methyl]-2H-imidazol-2-one;

1-isobutyl-4-propyl-1,3-dihydro-3-[[6-[2-(1H-tetrazol-5-yl)phenyl]-3-pyridinyl]methyl]-2H-imidazol-2-one;

1-tertbutyl-4-propyl-1,3-dihydro-3-[[6-[2-(1H-tetrazol-5-yl)phenyl]-3-pyridinyl]methyl]-2H-imidazol-2-one;

1-pentyl-4-propyl-1,3-dihydro-3-[[6-[2-(1H-tetrazol-5-yl)phenyl]-3-pyridinyl]methyl]-2H-imidazol-2-one;

1-isopentyl-4-propyl-1,3-dihydro-3-[[6-[2-(1H-tetrazol-5-yl)phenyl]-3-pyridinyl]methyl]-2H-imidazol-2-one;

1-cyclohexyl-4-propyl-1,3-dihydro-3-[[6-[2-(1H-tetrazol-5-yl)phenyl]-3-pyridinyl]methyl]-2H-imidazol-2-one;

1-cyclohexylmethyl-4-propyl-1,3-dihydro-3-[[6-[2-(1H-tetrazol-5-yl)phenyl]-3-pyridinyl]methyl]-2H-imidazol-2-one;

1-phenyl-4-propyl-1,3-dihydro-3-[[6-[2-(1H-tetrazol-5-yl)phenyl]-3-pyridinyl]methyl]-2H-imidazol-2-one;

1-phenylmethyl-4-propyl-1,3-dihydro-3-[[6-[2-(1H-tetrazol-5-yl)phenyl]-3-pyridinyl]methyl]-2H-imidazol-2-one;

1-(2-cyclohexylethyl)-4-propyl-1,3-dihydro-3-[[6-[2-(1H-tetrazol-5-yl)phenyl]-3-pyridinyl]methyl]-2H-imidazol-2-one;

1-(2-phenylethyl)-4-propyl-1,3-dihydro-3-[[6-[2-(1H-tetrazol-5-yl)phenyl]-3-pyridinyl]methyl]-2H-imidazol-2-one;

1-methyl-4-butyl-1,3-dihydro-3-[[6-[2-(1H-tetrazol-5-yl)phenyl]-3-pyridinyl]methyl]-2H-imidazol-2-one;

1-ethyl-4-butyl-1,3-dihydro-3-[[6-[2-(1H-tetrazol-5-yl)phenyl]-3-pyridinyl]methyl]-2H-imidazol-2-one;

1-propyl-4-butyl-1,3-dihydro-3-[[6-[2-(1H-tetrazol-5-yl)phenyl]-3-pyridinyl]methyl]-2H-imidazol-2-one;

1-isopropyl-4-butyl-1,3-dihydro-3-[[6-[2-(1H-tetrazol-5-yl)phenyl]-3-pyridinyl]methyl]-2H-imidazol-2-one;

1,4-dibutyl-1,3-dihydro-3-[[6-[2-(1H-tetrazol-5phenyl]-3-pyridinyl]methyl]-2H-imidazol-2-one;

1-secbutyl-4-butyl-1,3-dihydro-3-[[6-[2-(1H-tetrazol-5-yl)phenyl]-3-pyridinyl]methyl]-2H-imidazol-2-one;

1-isobutyl-4-butyl-1,3-dihydro-3-[[6-[2-(1H-tetrazol-5-yl)phenyl]-3-pyridinyl]methyl]-2H-imidazol-2-one;

1-tertbutyl-4-butyl-1,3-dihydro-3-[[6-[2-(1H-tetrazol-5-yl)phenyl]-3-pyridinyl]methyl]-2H-imidazol-2-one;

1-pentyl-4-butyl-1,3-dihydro-3-[[6-[2-(1H-tetrazol-5-yl)phenyl]-3-pyridinyl]methyl]-2H-imidazol-2-one;

1-isopentyl-4-butyl-1,3-dihydro-3-[[6-[2-(1H-tetrazol-5-yl)phenyl]-3-pyridinyl]methyl]-2H-imidazol-2-one;

1-cyclohexyl-4-butyl-1,3-dihydro-3-[[6-[2-(1H-tetrazol-5-yl)phenyl]-3-pyridinyl]methyl]-2H-imidazo! -2-one;

1-cyclohexylmethyl-4-butyl-1,3-dihydro-3-[[6-[2-(1H-tetrazol-5-yl) -yl)phenyl]-3-pyridinyl]methyl]-2H-imidazol-2-one;

1-phenyl-4-butyl-1,3-dihydro-3-[[6-[2-(1H-tetrazol-5-yl)phenyl]-3-pyridinyl]methyl]-2H-imidazol-2-one;

1-phenylmethyl-4-butyl-1,3-dihydro-3-[[6-[2-(1H-tetrazol-5-yl)phenyl]-3-pyridinyl]methyl]-2H-imidazol-2-one;

1-(2-cyclohexylethyl)-4-butyl-1,3-dihydro-3-[[6-[2-(1H-tetrazol-5-yl)phenyl]-3-pyridinyl]methyl]-2H-imidazol-2-one;

1-(2-phenylethyl)-4-butyl-1,3-dihydro-3-[[6-[2-(1H-tetrazol-5-yl)phenyl]-3-pyridinyl]methyl]-2H-imidazol-2-one;

1-methyl-4-pentyl-1,3-dihydro-3-[[6-[2-(1H-tetrazol-5-yl)phenyl]-3-pyridinyl]methyl]-2H-imidazol-2-one;

1-ethyl-4-pentyl-1,3-dihydro-3-[[6-[2-(1H-tetrazol-5-yl)phenyl]-3-pyridinyl]methyl]-2H-imidazol-2-one;

1-propyl-4-pentyl-1,3-dihydro-3-[[6-[2-(1H-tetrazol-5-yl)phenyl]-3-pyridinyl]methyl]-2H-imidazol-2-one;

1-isopropyl-4-pentyl-1,3-dihydro-3-[[6-[2-(1H-tetrazol-5-yl)phenyl]-3-pyridinyl]methyl]-2H-imidazol-2-one;

1-butyl-4-pentyl-1,3-dihydro-3-[[6-[2-(1H-tetrazol-5-yl)phenyl]-3-pyridinyl]methyl]-2H-imidazol-2-one;

1-secbutyl-4-pentyl-1,3-dihydro-3-[[6-[2-(1H-tetrazol-5-yl)phenyl]-3-pyridinyl]methyl]-2H-imidazol-2-one;

1-isobutyl-4-pentyl-1,3-dihydro-3-[[6-[2-(1H-tetrazol-5-yl)phenyl]-3-pyridinyl]methyl]-2H-imidazol-2-one;

1-tertbutyl-4-pentyl-1,3-dihydro-3-[[6-[2-(1H-tetrazol-5-yl)phenyl]-3-pyridinyl]methyl]-2H-imidazol-2-one;

1,4-dipentyl-1,3-dihydro-3-[[6-[2-(1H-tetrazol-5-yl)phenyl]-3-pyridinyl]methyl]-2H-imidazol-2-one;

1-isopentyl-4-pentyl-1,3-dihydro-3-[[6-[2-(1H-tetrazol-5-yl)phenyl]-3-pyridinyl]methyl]-2H-imidazol-2-one;

1-cyclohexyl-4-pentyl-1,3-dihydro-3-[[6-[2-(1H-tetrazol-5-yl)phenyl]-3-pyridinyl]methyl]-2H-imidazol-2-one;

1-cyclohexylmethyl-4-pentyl-1,3-dihydro-3-[[6-[2-(1H-tetrazol-5-yl)phenyl]-3-pyridinyl]methyl]-2H-imidazol-2-one;

1-phenyl-4-pentyl-1,3-dihydro-3-[[6-[2-(1H-tetrazol-5-yl)phenyl]-3-pyridinyl]methyl]-2H-imidazol-2-one;

1-phenylmethyl-4-pentyl-1,3-dihydro-3-[[6-[2-(1H-tetrazol-5-yl)phenyl]-3-pyridinyl]methyl]-2H-imidazol-2-one;

1-(2-cyclohexylethyl)-4-pentyl-1,3-dihydro-3-[[6-[2-(1H-tetrazol-5-yl)phenyl]-3-pyridinyl]methyl]-2H-imidazol-2-one;

1-(2-phenylethyl)-4-pentyl-1,3-dihydro-3-[[6-[2-(1H-tetrazol-5-yl)phenyl]-3-pyridinyl]methyl]-2H-imidazol-2-one;

1,5-dimethyl-4-propyl-1,3-dihydro-3-[[6-[2-(1H-tetrazol-5-yl)phenyl]-3-pyridinyl]methyl]-2H-imidazol-2-one;

1-ethyl-4-propyl-5-methyl-1,3-dihydro-3-[[6-[2-(1H-tetrazol-5-yl)phenyl]-3-pyridinyl]methyl]-2H-imidazol-2-one;

1,4-dipropyl-5-methyl-1,3-dihydro-3-[[6-[2-(1H-tetrazol-5-yl)phenyl]-3-pyridinyl]methyl]-2H-imidazol-2-one;

1-isopropyl-4-propyl-5-methyl-1,3-dihydro-3-[[6-[2-(1H-tetrazol-5-yl)phenyl]-3-pyridinyl]methyl]-2H-imidazol-2-one;

1-butyl-4-propyl-5-methyl-1,3-dihydro-3-[[6-[2-(1H-tetrazol-5-yl)phenyl]-3-pyridinyl]methyl]-2H-imidazol-2-one;

1-secbutyl-4-propyl-5-methyl-1,3-dihydro-3-[[6-[2-(1H-tetrazol-5-yl)phenyl]-3-pyridinyl]methyl]-2H-imidazol-2-one;

1-isobutyl-4-propyl-5-methyl-1,3-dihydro-3-[[6-[2-(1H-tetrazol-5-yl)phenyl]-3-pyridinyl]methyl]-2H-imidazol-2-one;

1-tertbutyl-4-propyl-5-methyl-1,3-dihydro-3-[[6-[2-(1H-tetrazol-5-yl)phenyl]-3-pyridinyl]methyl]-2H-imidazol-2-one;

1-pentyl-4-propyl-5-methyl-1,3-dihydro-3-[[6-[2-(1H-tetrazol-5-yl)phenyl]-3-pyridinyl]methyl]-2H-imidazol-2-one;

1-isopentyl-4-propyl-5-methyl-1,3-dihydro-3-[[6-[2-(1H-tetrazol-5-yl)phenyl]-3-pyridinyl]methyl]-2H-imidazol-2-one;

1-cyclohexyl-4-propyl-5-methyl-1,3-dihydro-3-[[6-[2-(1H-tetrazol-5-yl)phenyl]-3-pyridinyl]methyl]-2H-imidazol-2-one;

1-cyclohexylmethyl-4-propyl-5-methyl-1,3-dihydro-3-[[6-[2-(1H-tetrazol-5-yl) -yl)phenyl]-3-pyridinyl]methyl]-2H-imidazol-2-one;

1-phenyl-4-propyl-5-methyl-1,3-dihydro-3-[[6-[2-(1H-tetrazol-5-yl)phenyl]-3-pyridinyl]methyl]-2H-imidazol-2-one;

1-phenylmethyl-4-propyl-5-methyl-1,3-dihydro-3-[[6-[2-(1H-tetrazol-5-yl)phenyl]-3-pyridinyl]methyl]-2H-imidazol-2-one;

1-(2-cyclohexylethyl)-4-propyl-5-methyl-1,3-dihydro-3-[[6-2- (1H-tetrazol-5phenyl]-3-pyridinyl)methyl]-2H-imidazol-2-one;

1-(2-phenylethyl)-4-propyl-5-methyl-1,3-dihydro-3-[[6-[2-(1H-tetrazol-5-yl) -yl)phenyl]-3-pyridinyl]methyl]-2H-imidazol-2-one;

1,5-dimethyl-4-butyl-1,3-dihydro-3-[[6-[2-(1H-tetrazol-5-yl)phenyl]-3-pyridinyl]methyl]-2H-imidazol-2-one;

1-ethyl-4-butyl-5-methyl-1,3-dihydro-3-[[6-[2-(1H-tetrazol-5-yl)phenyl]-3-pyridinyl]methyl]-2H-imidazol-2-one;

1-propyl-4-butyl-5-methyl-1,3-dihydro-3-[[6-[2-(1H-tetrazol-5-yl)phenyl]-3-pyridinyl]methyl]-2H-imidazol-2-one;

1-isopropyl-4-butyl-5-methyl-1,3-dihydro-3-[[6-[2-(1H-tetrazol-5-yl)phenyl]-3-pyridinyl]methyl]-2H-imidazol-2-one;

1, 4-dibutyl-5-methyl-1,3-dihydro-3-[[6-[2-(1H-tetrazol-5-yl)phenyl]-3-pyridinyl]methyl]-2H-imidazol-2-one;

1-secbutyl-4-butyl-5-methyl-1,3-dihydro-3-[[6-[2-(1H-tetrazol-5-yl)phenyl]-3-pyridinyl]methyl]-2H- imidazol-2-one;

1-isobutyl-4-butyl-5-methyl-1,3-dihydro-3-[[6-[2-(1H-tetrazol-5-yl)phenyl]-3-pyridinyl]methyl]-2H-imidazol-2-one;

1-tertbutyl-4-butyl-5-methyl-1,3-dihydro-3-[[6-[2-(1H-tetrazol-5-yl)phenyl]-3-pyridinyl]methyl]-2H-imidazol-2-one;

1-pentyl-4-butyl-5-methyl-1,3-dihydro-3-[[6-[2-(1H-tetrazol-5-yl)phenyl]-3-pyridinyl]methyl]-2H-imidazol-2-one;

1-isopentyl-4-butyl-5-methyl-1,3-dihydro-3-[[6-[2-(1H-tetrazol-5-yl)phenyl]-3-pyridinyl]methyl]-2H-imidazol-2-one;

1-cyclohexyl-4-butyl-5-methyl-1,3-dihydro-3-[[6-[2-(1H-tetrazol-5-yl)phenyl]-3-pyridinyl]methyl]-2H-imidazol-2-one;

1-cyclohexylmethyl-4-butyl-5-methyl-1,3-dihydr6-3-[[6-[2-(1H-tetrazol-5-yl) -yl)phenyl]-3-pyridinyl]methyl]-2H-imidazol-2-one;

1-phenyl-4-butyl-5-methyl-1,3-dihydro-3-[[6-[2-(1H-tetrazol-5-yl)phenyl]-3-pyridinyl]methyl]-2H-imidazol-2-one;

1-phenylmethyl-4-butyl-5-methyl-1,3-dihydro-3-[[6-[2-(1H-tetrazol-5-yl)phenyl]-3-pyridinyl]methyl]-2H-imidazol-2-one;

1-(2-cyclohexylethyl)-4-butyl-5-methyl-1,3-dihydro-3-[[6-[2-(1H-tetrazol-5-yl) -yl)phenyl]-3-pyridinyl]methyl]-2H-imidazol-2-one;

1-(2-phenylethyl)-4-butyl-5-methyl-1,3-dihydro-3-[[6-[2-(1H-tetrazol-5-yl) -yl)phenyl]-3-pyridinyl]methyl]-2H-imidazol-2-one;

1-methyl-4-pentyl-5-methyl-1,3-dihydro-3-[[6-[2-(1H-tetrazol-5-yl)phenyl]-3-pyridinyl]methyl]-2H-imidazol-2-one;

1-ethyl-4-pentyl-5-methyl-1,3-dihydro-3-[[6-[2-(1H-tetrazol-5-yl)phenyl]-3-pyridinyl]methyl]-2H-imidazol-2-one;

1-propyl-4-pentyl-5-methyl-1,3-dihydro-3-[[6-[2-(1H-tetrazol-5-yl)phenyl]-3-pyridinyl]methyl]-2H-imidazol-2-one;

1-isopropyl-4-pentyl-5-methyl-1,3-dihydro-3-[[6-[2-(1H-tetrazol-5-yl)phenyl]-3-pyridinyl]methyl]-2H-imidazol-2-one;

1-butyl-4-pentyl-5-methyl-1,3-dihydro-3-[[6-[2-(1H-tetrazol-5-yl)phenyl]-3-pyridinyl]methyl]-2H-imidazol-2-one;

1-secbutyl-4-pentyl-5-methyl-1,3-dihydro-3-[[6-[2-(1H-tetrazol-5-yl)phenyl]-3-pyridinyl]methyl]-2H-imidazol-2-one;

1-isobutyl-4-pentyl-5-methyl-1,3-dihydro-3-[[6-[2-(1H-tetrazol-5-yl)phenyl]-3-pyridinyl]methyl]-2H-imidazol-2-one;

1-tertbutyl-4-pentyl-5-methyl-1,3-dihydro-3-[[6-[2-(1H-tetrazol-5-yl)phenyl]-3-pyridinyl]methyl]-2H-imidazol-2-one;

1,4-dipentyl-5-methyl-1,3-dihydro-3-[[6-[2-(1H-tetrazol-5-yl)phenyl]-3-pyridinyl]methyl]-2H-imidazol-2-one;

1-isopentyl-4-pentyl-5-methyl-1,3-dihydro-3-[[6-[2-(1H-tetrazol-5-yl)phenyl]-3-pyridinyl]methyl]-2H-imidazol-2-one;

1-cyclohexyl-4-pentyl-5-methyl-1,3-dihydro-3-[6-[2-(1H-tetrazol-5-yl)phenyl]-3-pyridinyl]methyl]-2H-imidazol-2-one;

1-cyclohexylmethyl-4-pentyl-5-methyl-1,3-dihydro-3-[[6-[2-(1H-tetrazol-5-yl) -yl)phenyl]-3-pyridinyl]methyl]-2H-imidazol-2-one;

1-phenyl-4-pentyl-5-methyl-1,3-dihydro-3-[[6-[2-(1H-tetrazol-5-yl)phenyl]-3-pyridinyl]methyl]-2H-imidazol-2-one;

1-phenylmethyl-4-pentyl-5-methyl-1,3-dihydro-3-[[6-[2-(1H-tetrazol-5-yl)phenyl]-3-pyridinyl]methyl]-2H-imidazol-2-one;

1-(2-cyclohexylethyl)-4-pentyl-5-methyl-1,3-dihydro-3-[[6-[2-(1H-tetrazol-5-yl) -yl)phenyl]-3-pyridinyl]methyl]-2H-imidazol-2-one;

1-(2-phenylethyl)-4-pentyl-5-methyl-1,3-dihydro3-[[6-[2-(1H-tetrazol-5-yl) -yl)phenyl]-3-pyridinyl]methyl]-2H-imidazol-2-one;

1-methyl-4-propyl-5-chloro-1,3-dihydro-3-[[6-[2-(1H-tetrazol-5-yl)phenyl]-3-pyridinyl]methyl]-2H-imidazol-2-one;

1-ethyl-4-propyl-5-chloro-1,3-dihydro-3-[[6-[2-(1H-tetrazol-5-yl)phenyl]-3-pyridinyl]methyl]-2H-imidazol-2-one;

1,4-dipropyl-5-chloro-1,3-dihydro-3-[[6-[2-(1H-tetrazol-5-yl)phenyl]-3-pyridinyl]methyl]-2H-imidazol-2-one;

1-isopropyl-4-propyl-5-chloro-1,3-dihydro-3-[[6-[2-(1H-tetrazol-5-yl)phenyl]-3-pyridinyl]methyl]-2H-imidazol-2-one;

1-butyl-4-propyl-5-chloro-1,3-dihydro-3-[[6-[2-(1H-tetrazol-5-yl)phenyl]-3-pyridinyl]methyl]-2H-imidazol-2-one;

1-secbutyl-4-propyl-5-chloro-1,3-dihydro-3-[[6-[2-(1H-tetrazol-5-yl)phenyl]-3-pyridinyl]methyl]-2H-imidazol-2-one;

1-isobutyl-4-propyl-5-chloro-1,3-dihydro-3-[[6-[2-(1H-tetrazol-5-yl)phenyl]-3-pyridinyl]methyl]-2H-imidazol-2-one;

1-tertbutyl-4-propyl-5-chloro-1,3-dihydro-3-[[6-[2-(1H-tetrazol-5-yl)phenyl]-3-pyridinyl]methyl]-2H-imidazol-2-one;

1-pentyl-4-propyl-5-chloro-1,3-dihydro-3-[[6-[2-(1H-tetrazol-5-yl)phenyl]-3-pyridinyl]methyl]-2H-imidazol-2-one;

1-isopentyl-4-propyl-5-chloro-1,3-dihydro-3-[[6-[2-(1H-tetrazol-5-yl)phenyl]-3-pyridinyl]methyl]-2H-imidazol-2-one;

1-cyclohexyl-4-propyl-5-chloro-1,3-dihydro-3-[[6-[2-(1H-tetrazol-5-yl)phenyl]-3-pyridinyl]methyl]-2-imidazol-2-one;

1-cyclohexylmethyl-4-propyl-5-chloro-1,3-dihydro-3-[[6-[2-(1H-tetrazol-5-yl) -yl)phenyl]-3-pyridinyl]methyl]-2H-imidazol-2-one;

1-phenyl-4-propyl-5-chloro-1,3-dihydro-3-[[6-[2-(1H-tetrazol-5-yl)phenyl]-3-pyridinyl]methyl]-2H-imidazol-2-one;

1-phenylmethyl-4-propyl-5-chloro-1,3-dihydro-3-[[6-[2-(1H-tetrazol-5-yl)phenyl]-3-pyridinyl]methyl]-2H-imidazol-2-one;

1-(2-cyclohexylethyl)-4-propyl-5-chloro-1,3-dihydro-3-[[6-[2-(1H-tetrazol-5-yl) -yl)phenyl]-3-pyridinyl]methyl]-2H-imidazol-2-one;

1-(2-phenylethyl)-4-propyl-5-chloro-1,3-dihydr6-3-[[6-[2-(1H-tetrazol-5-yl) -yl)phenyl]-3-pyridinyl]methyl]-2H-imidazol-2-one;

1-methyl-4-butyl-5-chloro-1,3-dihydro-3-[[6-[2-(1H-tetrazol-5-yl)phenyl]-3-pyridinyl]methyl]-2H-imidazol-2-one;

1-ethyl-4-butyl-5-chloro-1,3-dihydro-3-[[6-[2-(1H-tetrazol-5-yl)phenyl]-3-pyridinyl]methyl]-2H-imidazol-2-one;

1-propyl-4-butyl-5-chloro-1,3-dihydro-3-[[6-[3-(1H-tetrazol-5-yl)phenyl]-3-pyridinyl]methyl]-2H-imidazol-2-one;

1-isopropyl-4-butyl-5-chloro-1,3-dihydro-3-[[6-[2-(1H-tetrazol-5-yl)phenyl]-3-pyridinyl]methyl]-2H-imidazol-2-one;

1,4-dibutyl-5-chloro-1,3-dihydro-3-[[6-[2-(1H-tetrazol-5-yl)phenyl]-3-pyridinyl]methyl]-2H-imidazol-2-one;

1-secbutyl-4-butyl-5-chloro-1,3-dihydro-3-[[6-[2-(1H-tetrazol-5-yl)phenyl]-3-pyridinyl]methyl]-2H-imidazol-2-one;

1-isobutyl-4-butyl-5-chloro-1,3-dihydro-3-[[6-[2-(1H-tetrazol-5-yl)phenyl]-3-pyridinyl]methyl]-2H-imidazol-2-one;

1-tertbutyl-4-butyl-5-chloro-1,3-dihydro-3-[[6-[2-(1H-tetrazol-5-yl)phenyl]-3-pyridinyl]methyl]-2H-imidazol-2-one;

1-pentyl-4-butyl-5-chloro-1,3-dihydro-3-[[6-[2-(1H-tetrazol-5-yl)phenyl]-3-pyridinyl]methyl]-2H-imidazol-2-one;

1-isopentyl-4-butyl-5-chloro-1,3-dihydro-3-[[6-[2-(1H-tetrazol-5-yl)phenyl]-3-pyridinyl]methyl]-2H-imidazol-2-one;

1-cyclohexyl-4-butyl-5-chloro-1,3-dihydro-3-[[6-[2-(1H-tetrazol-5-yl)phenyl]-3-pyridinyl]methyl]-2H-imidazol-2-one;

1-cyclohexylmethyl-4-butyl-5-chloro-1,3-dihydro-3-[[6-[2-(1H-tetrazol-5-yl)phenyl]-3-pyridinyl]methyl]-2H-imidazol-2-one;

1-phenyl-4-butyl-5-chloro-1,3-dihydro-3-[[6-[2-(1H-tetrazol-5-yl)phenyl]-3-pyridinyl]methyl]-2H-imidazol-2-one;

1-phenylmethyl-4-butyl-5-chloro-1,3-dihydro-3-[[6-[2-(1H-tetrazol-5-yl)phenyl]-3-pyridinyl]methyl]-2H-imidazol-2-one;

1-(2-cyclohexylethyl)-4-butyl-5-chloro-1,3-dihydro-3-[[6-[2-(1H-tetrazol-5-yl) -yl)phenyl]-3-pyridinyl]methyl]-2H-imidazol-2-one;

1-(2-phenylethyl)-4-butyl-5-chloro-1,3-dihydro-3-[[6-[2-(1H-tetrazol-5-yl) -yl)phenyl]-3-pyridinyl]methyl]-2H-imidazol-2-one;

1-methyl-4-pentyl-5-chloro-1,3-dihydro-3-[[6-[2-(1H-tetrazol-5phenyl]-3-pyridinyl]methyl]-2H-imidazol-2-one;

1-ethyl-4-pentyl-5-chloro-1,3-dihydro-3-[[6-[2-(1H-tetrazol-5-yl)phenyl]-3-pyridinyl]methyl]-2H-imidazol-2-one;

1-propyl-4-pentyl-5-chloro-1,3-dihydro-3-[[6-[2-(1H-tetrazol-5phenyl]-3-pyridinyl]methyl]-2H-imidazol-2-one;

1-isopropyl-4-pentyl-5-chloro-1,3-dihydro-3-[[6-[2-(1H-tetrazol-5-yl)phenyl]-3-pyridinyl]methyl]-2H-imidazol-2-one;

1-butyl-4-pentyl-5-chloro-1,3-dihydro-3-[[6-[2-(1H-tetrazol-5-yl)phenyl]-3-pyridinyl]methyl]-2H-imidazol-2-one;

1-secbutyl-4-pentyl-5-chloro-1,3-dihydro-3-[[6-[2-(1H-tetrazol-5-yl)phenyl]-3-pyridinyl]methyl]-2H-imidazol-2-one;

1-isobutyl-4-pentyl-5-chloro-1,3-dihydro-3-[[6-[2-(1H-tetrazol-5-yl)phenyl]-3-pyridinyl]methyl]-2H-imidazol-2-one;

1-tertbutyl-4-pentyl-5-chloro-1,3-dihydro-3-[[6-[2-(1H-tetrazol-5-yl)phenyl]-3-pyridinyl]methyl]-2H-imidazol-2-one;

1,4-dipentyl-5-chloro-1,3-dihydro-3-[[6-[2-(1H-tetrazol-5-yl)-yl)phenyl]-3-pyridinyl]methyl]-2H-imidazol-2-one;

1-isopentyl-4-pentyl-5-chloro-1,3-dihydro-3-[[6-[2-(1H-tetrazol-5-yl)phenyl]-3-pyridinyl]methyl]-2H-imidazol-2-one;

1-cyclohexyl-4-pentyl-5-chloro-1,3-dihydro-3-[[6-[2-(1H-tetrazol-5-yl)phenyl]-3-pyridinyl]methyl]-2H-imidazol-2-one;

1-cyclohexylmethyl-4-pentyl-5-chloro-1,3-dihydro-3-[[6-[2-(1H-tetrazol-5-yl) -yl)phenyl]-3-pyridinyl]methyl]-2H-imidazol-2-one;

1-phenyl-4-pentyl-5-chloro-1,3-dihydro-3-[[6-[2-(1H-tetrazol-5-yl)phenyl]-3-pyridinyl]methyl]-2H-imidazol-2-one;

1-phenylmethyl-4-pentyl-5-chloro-1,3-dihydro-3-[[6-[2-(1H-tetrazol-5-yl)phenyl]-3-pyridinyl]methyl]-2H-imidazol-2-one;

1-(2-cyclohexylethyl)-4-pentyl-5-chloro-1,3-dihydro-3-[[6-[2-(1H-tetrazol-5-yl) -yl)phenyl]-3-pyridinyl]methyl]-2H-imidazol-2-one;

and 1-(2-phenylethyl)-4-pentyl-5-chloro-1,3-dihydro-3-[[6-[2-(1H-tetrazol-5-yl) -yl)phenyl]-3-pyridinyl]methyl]-2H-imidazol-2-one.

or a tautomer thereof or a pharmaceutically-acceptable salt thereof.

A family of specific compounds of particular interest within Formula III consists of compounds and pharmaceutically-acceptable salts thereof as follows:

1-propyl-4-butyl-1,3-dihydro-3-[[6-[2-(1H-tetrazol-5-yl)phenyl]-3-pyridinyl]methyl]-2H-imidazol-2-one;

1,4-dibutyl-1,3-dihydro-3-[[6-[2-(1H-tetrazol-5phenyl]-3-pyridinyl]methyl]-2H-imidazol-2-one;

1-pentyl-4-butyl-1,3-dihydro-3-[[6-[2-(1H-tetrazol-5-yl)phenyl]-3-pyridinyl]methyl]-2H-imidazol-2-one;

1-isopentyl-4-butyl-1,3-dihydro-3-[[6-[2-(1H-tetrazol-5-yl)phenyl]-3-pyridinyl]methyl]-2H-imidazol-2-one;

1-cyclohexylmethyl-4-butyl-1,3-dihydro-3-[[6-[2-(1H-tetrazol-5-yl)phenyl]-3-pyridinyl]methyl]-2H-imidazol-2-one;

1-phenylmethyl-4-butyl-1,3-dihydro-3-[[6-[2-(1H-tetrazol-5-yl)phenyl]-3-pyridinyl]methyl]-2H-imidazol-2-one;

1-(2-cyclohexylethyl)-4-butyl-1,3-dihydro-3-[[6-[2-(1H-tetrazol-5-yl)phenyl]-3-pyridinyl]methyl]-2H-imidazol-2-one;

1-(2-phenylethyl)-4-butyl-1,3-dihydro-3-[[6-[2-(1H-tetrazol-5-yl)phenyl]-3-pyridinyl]methyl]-2H-imidazol-2-one;

1-propyl-4-butyl-5-methyl-1,3-dihydro-3-[[6-[2-(1H-tetrazol-5-yl)phenyl]-3-pyridinyl]methyl]-2H-imidazol-2-one;

1,4-dibutyl-5-methyl-1,3-dihydro-3-[[6-[2-(1H-tetrazol-5-yl)phenyl]-3-pyridinyl]methyl]-2H-imidazol-2-one;

1-pentyl-4-butyl-5-methyl-1,3-dihydro-3-[[6-[2-(1H-tetrazol-5-yl)phenyl]-3-pyridinyl]methyl]-2H-imidazol-2-one;

1-isopentyl-4-butyl-5-methyl-1,3-dihydro-3-[[6-[2-(1H-tetrazol-5-yl)phenyl]-3-pyridinyl]methyl]-2H-imidazol-2-one;

1-cyclohexylmethyl-4-butyl-5-methyl-1,3-dihydro-3-[[6-[2-(1H-tetrazol-5-yl) -yl)phenyl]-3-pyridinyl]methyl]-2H-imidazol-2-one;

1-phenylmethyl-4-butyl-5-methyl-1,3-dihydro-3-[[6-[2-(1H-tetrazol-5-yl)phenyl]-3-pyridinyl]methyl]-2H-imidazol-2-one;

1-(2-cyclohexylethyl)-4-butyl-5-methyl-1,3-dihydro-3-[[6-[2-(1H-tetrazol-5-yl) -yl)phenyl]-3-pyridinyl]methyl]-2H-imidazol-2-one;

1-(2-phenylethyl)-4-butyl-5-methyl-1,3-dihydro-3-[[6-[2-(1H-tetrazol-5-yl) -yl)phenyl]-3-pyridinyl]methyl]-2H-imidazol-2-one;

1-propyl-4-butyl-5-chloro-1,3-dihydro-3-[[6-[2-(1H-tetrazol-5-yl)phenyl]-3-pyridinyl]methyl]-2H-imidazol-2-one;

1,4-dibutyl-5-chloro-1,3-dihydro-3-[[6-[2-(1H-tetrazol-5-yl)phenyl]-3-pyridinyl]methyl]-2H-imidazol-2-one;

1-pentyl-4-butyl-5-chloro-1,3-dihydro-3-[[6-[2-(1H-tetrazol-5-yl)phenyl]-3-pyridinyl]methyl]-2H-imidazol-2-one;

1-isopentyl-4-butyl-5-chloro-1,3-dihydro-3-[[6-[2-(1H-tetrazol-5-yl)phenyl]-3-pyridinyl]methyl]-2H-imidazol-2-one;

1-cyclohexylmethyl-4-butyl-5-chloro-1,3-dihydro-3-[[6-[2-(1H-tetrazol-5-yl) -yl)phenyl]-3-pyridinyl]methyl]-2H-imidazol-2-one;

1-phenylmethyl-4-butyl-5-chloro-1,3-dihydro-3-[[6-[2-(1H-tetrazol-5-yl)phenyl]-3-pyridinyl]methyl]-2H-imidazol-2-one;

1-(2-cyclohexylethyl)-4-butyl-5-chloro-1,3-dihydro-3-[[6-[2-(1H-tetrazol-5-yl) -yl)phenyl]-3-pyridinyl]methyl]-2H-imidazol-2-one;

and 1-(2-phenylethyl)-4-butyl-5-chloro-1,3-dihydro-3-[[6-[2-(1H-tetrazol-5-yl) -yl)phenyl]-3-pyridinyl]methyl]-2H-imidazol-2-one.

Within Formula I there is third sub-class of compounds of high interest as represented by Formula IV:

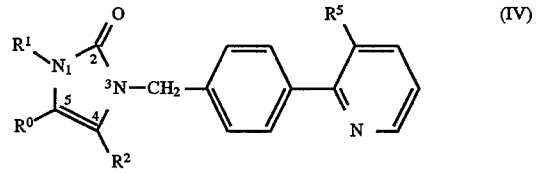

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $K^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

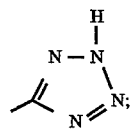

or a tautomer thereof or a pharmaceutically-acceptable salt thereof.

A family of specific compounds of particular interest within Formula IV consists of compounds and pharmaceutically-acceptable salts thereof as follows:

1-methyl-4-propyl-1,3-dihydro-3-[[4-[3-(1H-tetrazol-5-yl)-2-pyridinyl]phenyl]methyl]2H-imidazol-2-one;

1-ethyl-4-propyl-1,3-dihydro-3-[[4-[3-(1H-tetrazol-5-yl)-2-pyridinyl]-yl)phenyl]methyl]-2H-imidazol-2-one;
1,4-dipropyl-1,3-dihydro-3-[[4-[3-(1H-tetrazol-5-yl)-2-pyridinyl]-yl)phenyl]methyl]-2H-imidazol-2-one;
1-isopropyl-4-propyl-1,3-dihydro-3-[[4-[3-(1H-tetrazol-5-yl)-2-pyridinyl]phenyl]methyl]-2H-imidazol-2-one;
1-butyl-4-propyl-1,3-dihydro-3-[[4-[3-(1H-tetrazol-5-yl)-2-pyridinyl]phenyl]methyl]-2H-imidazol-2-one;
1-secbutyl-4-propyl-1,3-dihydro-3-[[4-[3-(1H-tetrazol-5-yl)-2-pyridinyl]phenyl]methyl]-2H-imidazol-2-one;
1-isobutyl-4-propyl-1,3-dihydro-3-[[4-[3-(1H-tetrazol-5-yl)-2-pyridinyl]phenyl]methyl]-2H-imidazol-2-one;
1-tertbutyl-4-propyl-1,3-dihydro-3-[[4-[3-(1H-tetrazol-5-yl)-2-pyridinyl]phenyl]methyl]-2H-imidazol-2-one;
1-pentyl-4-propyl-1,3-dihydro-3-[[4-[3-(1H-tetrazol-5-yl)-2-pyridinyl]phenyl]methyl]-2H-imidazol-2-one;
1-isopentyl-4-propyl-1,3-dihydro-3-[[4-[3-(1H-tetrazol-5-yl)-2-pyridinyl]phenyl]methyl]-2H-imidazol-2-one;
1-cyclohexyl-4-propyl-1,3-dihydro-3-[[4-[3-(1H-tetrazol-5-yl)-2-pyridinyl]phenyl]methyl]-2H-imidazol-2-one;
1-cyclohexylmethyl-4-propyl-1,3-dihydro-3-[[4-[3-(1H-tetrazol-5-yl)-2-pyridinyl]phenyl]methyl]-2H-imidazol-2-one;
1-phenyl-4-propyl-1,3-dihydro-3-[[4-[3-(1H-tetrazol-5-yl)-2-pyridinyl]phenyl]methyl]-2H-imidazol-2-one;
1-phenylmethyl-4-propyl-1,3-dihydro-3-[[4-[3-(1H-tetrazol-5-yl)-2-pyridinyl]phenyl]methyl]-2H-imidazol-2-one;
1-(2-cyclohexylethyl)-4-propyl-1,3-dihydro-3-[[4-[3-(1H-tetrazol-5-yl)-2-pyridinyl]phenyl]methyl]-2H-imidazol-2-one;
1-(2-phenylethyl)-4-propyl-1,3-dihydro-3-[[4-[3-(1H-tetrazol-5-yl)-2-pyridinyl]phenyl]methyl]-2H-imidazol-2-one;
1-methyl-4-butyl-1,3-dihydro-3-[[4-[3-(1H-tetrazol-5-yl)-2-pyridinyl]phenyl]methyl]-2H-imidazol-2-one;
1-ethyl-4-butyl-1,3-dihydro-3-[[4-[3-(1H-tetrazol-5-yl)-2-pyridinyl]phenyl]methyl]-2H-imidazol-2-one;
1-propyl-4-butyl-1,3-dihydro-3-[[4-[3-(1H-tetrazol-5-yl)-2-pyridinyl]phenyl]methyl]-2H-imidazol-2-one;
1-isopropyl-4-butyl-1,3-dihydro-3-[[4-[3-(1H-tetrazol-5-yl)-2-pyridinyl]phenyl]methyl]-2H-imidazol-2-one;
1,4-dibutyl-1,3-dihydro-3-[[4-[3-(1H-tetrazol-5-yl)-2-pyridinyl]phenyl]methyl]-2H-imidazol-2-one;
1-secbutyl-4-butyl-1,3-dihydro-3-[[4-[3-(1H-tetrazol-5-yl)-2-pyridinyl]phenyl]methyl]-2H-imidazol-2-one;
1-isobutyl-4-butyl-1,3-dihydro-3-[[4-[3-(1H-tetrazol-5-yl)-2-pyridinyl]phenyl]methyl]-2H-imidazol-2-one;
1-tertbutyl-4-butyl-1,3-dihydro-3-[[4-[3-(1H-tetrazol-5-yl)-2-pyridinyl]phenyl]methyl]-2H-imidazol-2-one;
1-pentyl-4-butyl-1,3-dihydro-3-[[4-[3-(1H-tetrazol-5-yl)-2-pyridinyl]phenyl]methyl]-2H-imidazol-2-one;
1-isopentyl-4-butyl-1,3-dihydro-3-[[4-[3-(1H-tetrazol-5-yl)-2-pyridinyl]phenyl]methyl]-2H-imidazol-2-one;
1-cyclohexyl-4-butyl-1,3-dihydro-3-[[4-[3-(1H-tetrazol-5-yl)-2-pyridinyl]phenyl]methyl]-2-H-imidazol-2-one;
1-cyclohexylmethyl-4-butyl-1,3-dihydro-3-[[4-[3-(1H-tetrazol-5-yl)-2-pyridinyl]phenyl]methyl]-2H-imidazol-2-one;
1-phenyl-4-butyl-1,3-dihydro-3-[[4-[3-(1H-tetrazol-5-yl)-2-pyridinyl]phenyl]methyl]-2H-imidazol-2-one;
1-phenylmethyl-4-butyl-1,3-dihydro-3-[[4-[3-(1H-tetrazol-5-yl)-2-pyridinyl]phenyl]methyl]-2H-imidazol-2-one;
1-(2-cyclohexylethyt)-4-butyl-1,3-dihydro-3-[[4-[3-(1H-tetrazol-5-yl)-2-pyridinyl]phenyl]methyl]-2H-imidazol-2-one;
1-(2-phenylethyl)-4-butyl-1,3-dihydro-3-[[4-[3-(1H-tetrazol-5-yl)-2-pyridinyl]phenyl]methyl]-2H-imidazol-2-one;
1-methyl-4-pentyl-1,3-dihydro-3-[[4-[3-(1H-tetrazol-5-yl)-2-pyridinyl]phenyl]methyl]-2H-imidazol-2-one;
1-ethyl-4-pentyl-1,3-dihydro-3-[[4-[3-(1H-tetrazol-5-yl)-2-pyridinyl]phenyl]methyl]-2H-imidazol-2-one;
1-propyl-4-pentyl-1,3-dihydro-3-[[4-[3-(1H-tetrazol-5-yl)-2-pyridinyl]phenyl]methyl]-2H-imidazol-2-one;
1-isopropyl-4-pentyl-1,3-dihydro-3-[[4-[3-(1H-tetrazol-5-yl)-2-pyridinyl]phenyl]methyl]-2H-imidazol-2-one;
1-butyl-4-pentyl-1,3-dihydro-3-[[4-[3-(1H-tetrazol-5-yl)-2-pyridinyl]phenyl]methyl]-2H-imidazol-2-one;
1-secbutyl-4-pentyl-1,3-dihydro-3-[[4-[3-(1H-tetrazol-5-yl)-2-pyridinyl]phenyl]methyl]-2H-imidazol-2-one;
1-isobutyl-4-pentyl-1,3-dihydro-3-[[4-[3-(1H-tetrazol-5-yl)-2-pyridinyl]phenyl]methyl]-2H-imidazol-2-one;
1-tertbutyl-4-pentyl-1,3-dihydro-3-[[4-[3-(1H-tetrazol-5-yl)-2-pyridinyl]phenyl]methyl]-2H-imidazol-2-one;
1,4-dipentyl-1,3-dihydro-3-[[4-[3-(1H-tetrazol-5-yl)-2-pyridinyl]phenyl]methyl]-2H-imidazol-2-one;
1-isopentyl-4-pentyl-1,3-dihydro-3-[[4-[3-(1H-tetrazol-5-yl)-2-pyridinyl]phenyl]methyl]-2H-imidazol-2-one;
1-cyclohexyl-4-pentyl-1,3-dihydro-3-[[4-[3-(1H-tetrazol-5-yl)-2-pyridinyl]phenyl]methyl]-2H-imidazol-2-one;
1-cyclohexylmethyl-4-pentyl-1,3-dihydro-3-[[4-[3-(1H-tetrazol-5-yl)-2-pyridinyl]phenyl]methyl]-2H-imidazol-2-one;
1-phenyl-4-pentyl-1,3-dihydro-3-[[4-[3-(1H-tetrazol-5-yl)-2-pyridinyl]phenyl]methyl]-2H-imidazol-2-one;
1-phenylmethyl-4-pentyl-1,3-dihydro-3-[[4-[3-(1H-tetrazol-5-yl)-2-pyridinyl]methyl]-2H- imidazol-2-one;
1-(2-cyclohexylethyl)-4-pentyl-1,3-dihydro-3-[[4-[3-(1H-tetrazol-5-yl)-2-pyridinyl]phenyl]methyl]-2H-imidazol-2-one;
1-(2-phenylethyl)-4-pentyl-1,3-dihydro-3-[[4-[3-(1H-tetrazol-5-yl)-2-pyridinyl]phenyl]methyl]-2H-imidazol-2-one;
1,5-dimethyl-4-propyl-1,3-dihydro-3-[[4-[3-(1H-tetrazol-5-yl)-2-pyridinyl]phenyl]methyl]-2H-imidazol-2-one;
1-ethyl-4-propyl-5-methyl-1,3-dihydro-3-[[4-[3-(1H-tetrazol-5-yl)-2-pyridinyl]phenyl]methyl]-2H-imidazol-2-one;
1, 4-dipropyl-5-methyl-1,3-dihydro-3-[[4-[3-(1H-tetrazol-5-yl)-2-pyridinyl]phenyl]methyl]-2H-imidazol-2-one;
1-isopropyl-4-propyl-5-methyl-1,3-dihydro-3-[[4-[3-(1H-tetrazol-5-yl)-2-pyridinyl]phenyl]methyl]-2H-imidazol-2-one;
1-butyl-4-propyl-5-methyl-1,3-dihydro-3-[[4-[3-(1H-tetrazol-5-yl)-2-pyridinyl]phenyl]methyl]-2H-imidazol-2-one;
1-secbutyl-4-propyl-5-methyl-1,3-dihydro-3-[[4-[3-(1H-tetrazol-5-yl)-2-pyridinyl]phenyl]methyl]-2H-imidazol-2-one;
1-isobutyl-4-propyl-5-methyl-1,3-dihydro-3-[[4-[3-(1H-tetrazol-5-yl)-2-pyridinyl]phenyl]methyl]-2H-imidazol-2-one;
1-tertbutyl-4-propyl-5-methyl-1,3-dihydro-3-[[4-[3-(1H-tetrazol-5-yl)-2-pyridinyl]phenyl]methyl]-2H-imidazol-2-one;
1-pentyl-4-propyl-5-methyl-1,3-dihydro-3-[[4-[-3-(1H-tetrazol-5-yl)-2-pyridinyl]phenyl]methyl]-2H-imidazol-2-one;
1-isopentyl-4-propyl-5-methyl-1,3-dihydro-3-[[4-[3-(1H-tetrazol-5-yl)-2-pyridinyl]phenyl]methyl]-2H-imidazol-2-one;
1-cyclohexyl-4-propyl-5-methyl-1,3-dihydro-3-[[4-[3-(1H-tetrazol-5-yl)-2-pyridinyl]phenyl]methyl]-2H-imidazol-2-one;
1-cyclohexylmethyl-4-propyl-5-methyl-1,3-dihydro-3-[[4-[3-(1H-tetrazol-5-yl)-2-pyridinyl]phenyl]methyl]-2H-imidazol-2-one;

1-phenyl-4-propyl-5-methyl-1,3-dihydro-3-[[4-[3-(1H-tetrazol-5-yl)-2-pyridinyl]phenyl]methyl]-2H-imidazol-2-one;

1-phenylmethyl-4-propyl-5-methyl-1,3-dihydro-3-[[4-[3-(1H-tetrazol-5-yl)-2-pyridinyl]phenyl]methyl]-2H-imidazol-2-one;

1-(2-cyclohexylethyl)-4-propyl-5-methyl-1,3-dihydro-3-[[4-[3-(1H-tetrazol-5-yl)-2-pyridinyl]phenyl]methyl]-2H-imidazol-2-one;

1-(2-phenylethyl)-4-propyl-5-methyl-1,3-dihydro-3-[[4-[3-(1H-tetrazol-5-yl)-2-pyridinyl]phenyl]methyl]-2H-imidazol-2-one;

1,5-dimethyl-4-butyl-1,3-dihydro-3-[[4-[3-(1H-tetrazol-5-yl)-2-pyridinyl]phenyl]methyl]-2H-imidazol-2-one;

1-ethyl-4-butyl-5-methyl-1,3-dihydro-3-[[4-[3-(1H-tetrazol-5-yl)-2-pyridinyl]phenyl]methyl]-2H-imidazol-2-one;

1-propyl-4-butyl-5-methyl-1,3-dihydro-3-[[4-[3-(1H-tetrazol-5-yl)-2-pyridinyl]phenyl]methyl]-2H-imidazol-2-one;

1-isopropyl-4-butyl-5-methyl-1,3-dihydro-3-[[4-[3-(1H-tetrazol-5-yl)-2-pyridinyl]phenyl]methyl]-2H-imidazol-2-one;

1,4-dibutyl-5-methyl-1,3-dihydro-3-[[4-[3-(1H-tetrazol-5-yl)-2-pyridinyl]phenyl]methyl]-2H-imidazol-2-one;

1-secbutyl-4-butyl-5-methyl-1,3-dihydro-3-[[4-[3-(1H-tetrazol-5-yl)-2-pyridinyl]phenyl]methyl]-2H-imidazol-2-one;

1-isobutyl-4-butyl-5-methyl-1,3-dihydro-3-[[4-[3-(1H-tetrazol-5-yl)-2-pyridinyl]phenyl]methyl]-2H-imidazol-2-one;

1-tertbutyl-4-butyl-5-methyl-1,3-dihydro-3-[[4-[3-(1H-tetrazol-5-yl)-2-pyridinyl]phenyl]methyl]-2H-imidazol-2-one;

1-pentyl-4-butyl-5-methyl-1,3-dihydro-3-[[4-[3-(1H-tetrazol-5-yl)-2-pyridinyl]phenyl]methyl]-2H-imidazol-2-one;

1-isopentyl-4-butyl-5-methyl-1,3-dihydro-3-[[4-[3-(1H-tetrazol-5-yl)-2-pyridinyl]phenyl]methyl]-2H-imidazol-2-one;

1-cyclohexyl-4-butyl-5-methyl-1,3-dihydro-3-[[4-[3-(1H-tetrazol-5-yl)-2-pyridinyl]phenyl]methyl]-2H-imidazol-2-one;

1-cyclohexylmethyl-4-butyl-5-methyl-1,3-dihydro-3-[[4-[3-(1H-tetrazol-5-yl)-2-pyridinyl]phenyl]methyl]-2H-imidazol-2-one;

1-phenyl-4-butyl-5-methyl-1,3-dihydro-3-[[4-[3-(1H-tetrazol-5-yl)-2-pyridinyl]phenyl]methyl]-2H-imidazol-2-one;

1-phenylmethyl-4-butyl-5-methyl-1,3-dihydro-3-[[4-[3-(1H-tetrazol-5-yl)-2-pyridinyl]phenyl]methyl]-2H-imidazol-2-one;

1-(2-cyclohexylethyl)-4-butyl-5-methyl-1,3-dihydro-3-[[4-[3-(1H-tetrazol-5-yl)-2-pyridinyl]phenyl]methyl]-2H-imidazol-2-one;

1-(2-phenylethyl)-4-butyl-5-methyl-1,3-dihydro-3-[[4-[3-(1H-tetrazol-5-yl)-2-pyridinyl]phenyl]methyl]-2H-imidazol-2-one;

1,5-dimethyl-4-pentyl-1,3-dihydro-3-[[4-[3-(1H-tetrazol-5-yl)-2-pyridinyl]phenyl]methyl]-2H-imidazol-2-one;

1-ethyl-4-pentyl-5-methyl-1,3-dihydro-3-[[4-[3-(1H-tetrazol-5-yl)-2-pyridinyl]phenyl]methyl]-2H-imidazol-2-one;

1-propyl-4-pentyl-5-methyl-1,3-dihydro-3-[[4-[3-(1H-tetrazol-5-yl)-2-pyridinyl]phenyl]methyl]-2H-imidazol-2-one;

1-isopropyl-4-pentyl-5-methyl-1,3-dihydro-3-[[4-[3-(1H-tetrazol-5-yl)-2-pyridinyl]phenyl]methyl]-2H-imidazol-2-one;

1-butyl-4-pentyl-5-methyl-1,3-dihydro-3-[[4-[3-(1H-tetrazol-5-yl)-2-pyridinyl]phenyl]methyl]-2H-imidazol-2-one;

1-secbutyl-4-pentyl-5-methyl-1,3-dihydro-3-[[4-[3-(1H-tetrazol-5-yl)-2-pyridinyl]phenyl]methyl]-2H-imidazol-2-one;

1-isobutyl-4-pentyl-5-methyl-1,3-dihydro-3-[[4-[3-(1H-tetrazol-5-yl)-2-pyridinyl]phenyl]methyl]-2H-imidazol-2-one;

1-tertbutyl-4-pentyl-5-methyl-1,3-dihydro-3-[[4-[3-(1H-tetrazol-5-yl)-2-pyridinyl]phenyl]methyl]-2H-imidazol-2-one;

1,4-dipentyl-5-methyl-1,3-dihydro-3-[[4-[3-(1H-tetrazol-5-yl)-2-pyridinyl]phenyl]methyl]-2H-imidazol-2-one;

1-isopentyl-4-pentyl-5-methyl-1,3-dihydro-3-[[4-[3-(1H-tetrazol-5-yl)-2-pyridinyl]phenyl]methyl]-2H-imidazol-2-one;

1-cyclohexyl-4-pentyl-5-methyl-1,3-dihydro-3-[[4-[3-(1H-tetrazol-5-yl)-2-pyridinyl]phenyl]methyl]-2H-imidazol-2-one;

1-cyclohexylmethyl-4-pentyl-5-methyl-1,3-dihydro-3-[[4-[3-(1H-tetrazol-5-yl)-2-pyridinyl]phenyl]methyl]-2H-imidazol-2-one;

1-phenyl-4-pentyl-5-methyl-1,3-dihydro-3-[[4-[3-(1H-tetrazol-5-yl)-2-pyridinyl]phenyl]methyl]-2H-imidazol-2-one;

1-phenylmethyl-4-pentyl-5-methyl-1,3-dihydro-3-[[4-[3-(1H-tetrazol-5-yl)-2-pyridinyl]phenyl]methyl]-2H-imidazol-2-one;

1-(2-cyclohexylethyl)-4-pentyl-5-methyl-1,3-dihydro-3-[[4-[3-(1H-tetrazol-5-yl)-2-pyridinyl]phenyl]methyl]-2H-imidazol-2-one;

1-(2-phenylethyl)-4-pentyl-5-methyl-1,3-dihydro-3-[[4-[3-(1H-tetrazol-5-yl)-2-pyridinyl]phenyl]methyl]-2H-imidazol-2-one;

1-methyl-4-propyl-5-chloro-1,3-dihydro-3-[[4-[3-(1H-tetrazol-5-yl)-2-pyridinyl]phenyl]methyl]-2H-imidazol-2-one;

1-ethyl-4-propyl-5-chloro-1,3-dihydro-3-[[4-[3-(1H-tetrazol-5-yl)-2-pyridinyl]phenyl]methyl]-2H-imidazol-2-one;

1,4-dipropyl-5-chloro-1,3-dihydro-3-[[4-[3-(1H-tetrazol-5-yl)-2-pyridinyl]phenyl]methyl]-2H-imidazol-2-one;

1-isopropyl-4-propyl-5-chloro-1,3-dihydro-3-[[4-[3-(1H-tetrazol-5-yl)-2-pyridinyl]phenyl]methyl]-2H-imidazol-2-one;

1-butyl-4-propyl-5-chloro-1,3-dihydro-3-[[4-[3i(1H-tetrazol-5-yl)-2-pyridinyl]phenyl]methyl]-2H-imidazol-2-one;

1-secbutyl-4-propyl-5-chloro-1,3-dihydro-3-[[4-[3-(1H-tetrazol-5-yl)-2-pyridinyl]phenyl]methyl]-2H-imidazol-2-one;

1-isobutyl-4-propyl-5-chloro-1,3-dihydro-3-[[4-[3-(1H-tetrazol-5-yl)-2-pyridinyl]phenyl]methyl]-2H-tmidazol-2-one;

1-tertbutyl-4-propyl-5-chloro-1,3-dihydro-3-[[4-[3-(1H-tetrazol-5-yl)-2-pyridinyl]phenyl]methyl]-2H-imidazol-2-one;

1-pentyl-4-propyl-5-chloro-1,3-dihydro-3-[[4-[3-(1H-tetrazol-5-yl)-2-pyridinyl]phenyl]methyl]-2H-imidazol-2-one;

1-isopentyl-4-propyl-5-chloro-1,3-dihydro-3-[[4-[3-(1H-tetrazol-5-yl)-2-pyridinyl]phenyl]methyl]-2H-imidazol-2-one;

1-cyclohexyl-4-propyl-5-chloro-1,3-dihydro-3-[[4-[3-(1H-tetrazol-5-yl)-2-pyridinyl]phenyl]methyl]-2H-imidazol-2-one;

1-cyclohexylmethyl-4-propyl-5-chloro-1,3-dihydro-3-[[4-[3-(1H-tetrazol-5-yl)-2-pyridinyl]phenyl]methyl]-2H-imidazol-2-one;
1-phenyl-4-propyl-5-chloro-1,3-dihydro-3-[[4-[3-(1H-tetrazol-5-yl)-2-pyridinyl]phenyl]methyl]-2H-imidazol-2-one;
1-phenylmethyl-4-propyl-5-chloro-1,3-dihydro-3-[[4-[3-(1H-tetrazol-5-yl)-2-pyridinyl]phenyl]methyl]-2H-imidazol-2-one;
1-(2-cyclohexylethyl)-4-propyl-5-chloro-1,3-dihydro-3-[[4-[3-(1H-tetrazol-5-yl)-2-pyridinyl]phenyl]methyl]-2H-imidazol-2-one;
1-(2-phenylethyl)-4-propyl-5-chloro-1,3-dihydro-3-[[4-[3-(1H-tetrazol-5-yl)-2-pyridinyl]phenyl]methyl]-2H-imidazol-2-one;
1-methyl-4-butyl-5-chloro-1,3-dihydro-3-[[4-[3-(1H-tetrazol-5-yl)-2-pyridinyl]phenyl]methyl]-2H-imidazol-2-one;
1-ethyl-4-butyl-5-chloro-1,3-dihydro-3-[[4-[3-(1H-tetrazol-5-yl)-2-pyridinyl]phenyl]methyl]-2H-imidazol-2-one;
1-propyl-4-butyl-5-chloro-1,3-dihydro-3-[[4-[3-(1H-tetrazol-5-yl)-2-pyridinyl]phenyl]methyl]-2H-imidazol-2-one;
1-isopropyl-4-butyl-5-chloro-1,3-dihydro-3-[[4-[3-(1H-tetrazol-5-yl)-2-pyridinyl]phenyl]methyl]-2H-imidazol-2-one;
1,4-dibutyl-5-chloro-1,3-dihydro-3-[[4-[3-(1H-tetrazol-5-yl)-2-pyridinyl]phenyl]methyl]-2H-imidazol-2-one;
1-secbutyl-4-butyl-5-chloro-1,3-dihydro-3-[[4-[3-(1H-tetrazol-5-yl)-2-pyridinyl]phenyl]methyl]-2H-imidazol-2-one;
1-isobutyl-4-butyl-5-chloro-1,3-dihydro-3-[[4-[3-(1H-tetrazol-5-yl)-2-pyridinyl]phenyl]methyl]-2H-imidazol-2-one;
1-tertbutyl-4-butyl-5-chloro-1,3-dihydro-3-[[4-[3-(1H-tetrazol-5-yl)-2-pyridinyl]phenyl]methyl]-2H-imidazol-2-one;
1-pentyl-4-butyl-5-chloro-1,3-dihydro-3-[[4-[3-(1H-tetrazol-5-yl)-2-pyridinyl]phenyl]methyl]-2H-imidazol-2-one;
1-isopentyl-4-butyl-5-chloro-1,3-dihydro-3-[[4-[3-(1H-tetrazol-5-yl)-2-pyridinyl]phenyl]methyl]-2H-imidazol-2-one;
1-cyclohexyl-4-butyl-5-chloro-1,3-dihydro-3-[[4-[3-(1H-tetrazol-5-yl)-2-pyridinyl]phenyl]methyl]-2H-imidazol-2-one;
1-cyclohexylmethyl-4-butyl-5-chloro-1,3-dihydro-3-[[4-[3-(1H-tetrazol-5-yl)-2-pyridinyl]phenyl]methyl]-2H-imidazol-2-one;
1-phenyl-4-butyl-5-chloro-1,3-dihydro-3-[[4-[3-(1H-tetrazol-5-yl)-2-pyridinyl]phenyl]methyl]-2H-imidazol-2-one;
1-phenylmethyl-4-butyl-5-chloro-1,3-dihydro-3-[[4-[3-(1H-tetrazol-5-yl)-2-pyridinyl]phenyl]methyl]-2H-imidazol-2-one;
1-(2-cyclohexylethyl)-4-butyl-5-chloro-1,3-dihydro-3-[[4-[3-(1H-tetrazol-5-yl)-2-pyridinyl]phenyl]methyl]-2H-imidazol-2-one;
1-(2-phenylethyl)-4-butyl-5-chloro-1,3-dihydro-3-[[4-[3-(1H-tetrazol-5-yl)-2-pyridinyl]phenyl]methyl]-2H-imidazol-2-one;
1-methyl-4-pentyl-5-chloro-1,3-dihydro-3-[[4-3-(1H-tetrazol-5-yl)-2-pyridinyl]phenyl]methyl]-2H-imidazol-2-one, 1-ethyl-4-pentyl-5-chloro-1,3-dihydro-3-[[4-[3-(1H-tetrazol-5-yl)-2-pyridinyl]phenyl]methyl]-2H-imidazol-2-one;
1-propyl-4-pentyl-5-chloro-1,3-dihydro-3-[[4-[3-(1H-tetrazol-5-yl)-2-pyridinyl]phenyl]methyl]-2H-imidazol-2-one;
1-isopropyl-4-pentyl-5-chloro-1,3-dihydro-3-[[4-[3-(1H-tetrazol-5-yl)-2-pyridinyl]phenyl]methyl]-2H-imidazol-2-one;
1-butyl-4-pentyl-5-chloro-1,3-dihydro-3-[[4-[3-(1H-tetrazol-5-yl)-2-pyridinyl]phenyl]methyl]-2H-imidazol-2-one;
1-secbutyl-4-pentyl-5-chloro-1,3-dihydro-3-[[4-[3-1H-tetrazol-5-yl)-2-pyridinyl]phenyl]methyl]-2H-imidazol-2-one;
1-isobutyl-4-pentyl-5-chloro-1,3-dihydro-3-[[4-[3-(1H-tetrazol-5-yl)-2-pyridinyl]phenyl]methyl]-2H-imidazol-2-one;
1-tertbutyl-4-pentyl-5-chloro-1,3-dihydro-3-[[4-[3-(1H-tetrazol-5-yl)-2-pyridinyl]phenyl]methyl]-2H-imidazol-2-one;
1,4-dipentyl-5-chloro-1,3-dihydro-3-[[4-[3-(1H-tetrazol-5-yl)-2-pyridinyl]phenyl]methyl]-2H-imidazol-2-one;
1-isopentyl-4-pentyl-5-chloro-1,3-dihydro-3-[[4-[3-(1H-tetrazol-5-yl)-2-pyridinyl]phenyl]methyl]-2H-imidazol-2-one;
1-cyclohexyl-4-pentyl-5-chloro-1,3-dihydro-3-[[4-[3-(1H-tetrazol-5-yl)-2-pyridinyl]phenyl]methyl]-2H-imidazol-2-one;
1-cyclohexylmethyl-4-pentyl-5-chloro-1,3-dihydro-3-[[4-[3-(1H-tetrazol-5-yl)-2-pyridinyl]phenyl]methyl]-2H-imidazol-2-one;
1-phenyl-4-pentyl-5-chloro-1,3-dihydro-3-[[4-[3-(1H-tetrazol-5-yl)-2-pyridinyl]phenyl]methyl]-2H-imidazol-2-one;
1-phenylmethyl-4-pentyl-5-chloro-1,3-dihydro-3-[[4-[3-(1H-tetrazol-5-yl)-2-pyridinyl]phenyl]methyl]-2H-imidazol-2-one;
1-(2-cyclohexylethyl)-4-pentyl-5-chloro-1,3-dihydro-3-[[4-[3-(1H-tetrazol-5-yl)-2-pyridinyl]phenyl]methyl]-2H-imidazol-2-one;
and 1-(2-phenylethyl)-4-pentyl-5-chloro-1,3-dihydro-3-[[4-[3-(1H-tetrazol-5-yl)-2-pyridinyl]phenyl]methyl]-2H-imidazol-2-one.

A family of compounds of more particular interest within Formula IV consists of compounds and pharmaceutically-acceptable salts thereof as follows: 1-propyl-4-butyl-1,3-dihydro-3-[[4-[3-(1H-tetrazol-5-yl)-2-pyridinyl]phenyl]methyl]-2H-imidazol-2-one;
1,4-dibutyl-1,3-dihydro-3-[[4-[3-(1H-tetrazol-5-yl)-2-pyridinyl]phenyl]methyl]-2H-imidazol-2-one;
1-pentyl-4-butyl-1,3-dihydro-3-[[4-[3-(1H-tetrazol-5-yl)-2-pyridinyl]phenyl]methyl]-2H-imidazol-2-one;
1-isopentyl-4-butyl-1,3-dihydro-3-[[4-[3-(1H-tetrazol-5-yl)-2-pyridinyl]phenyl]methyl]-2H-imidazol-2-one;
1-cyclohexylmethyl-4-butyl-1,3-dihydro-3-[[4-[3-(1H-tetrazol-5-yl)-2-pyridinyl]phenyl]methyl]-2H-imidazol-2-one;
1-phenylmethyl-4-butyl-1,3-dihydro-3-[[4-[3-(1H-tetrazol-5-yl)-2-pyridinyl]phenyl]methyl]-2H-imidazol-2-one;
1-(2-cyclohexylethyl)-4-butyl-1,3-dihydro-3-[[4-[3-(1H-tetrazol-5-yl)-2-pyridinyl]phenyl]methyl]-2H-imidazol-2-one;
1-(2-phenylethyl)-4-butyl-1,3-dihydro-3-[[4-[3-(1H-tetrazol-5-yl)-2-pyridinyl]phenyl]methyl]-2H-imidazol-2-one;
1-propyl-4-butyl-5-methyl-1,3-dihydro-3-[[4-[3-(1H-tetrazol-5-yl)-2-pyridinyl]phenyl]methyl]-2H-imidazol-2-one;
1,4-dibutyl-5-methyl-1,3-dihydro-3-[[4-[3-(1H-tetrazol-5-yl)-2-pyridinyl]phenyl]methyl]-2H-imidazol-2-one;
1-pentyl-4-butyl-5-methyl-1,3-dihydro-3-[[4-[3-(1H-tetrazol-5-yl)-2-pyridinyl]phenyl]methyl]-2H-imidazol-2-one;

1-isopentyl-4-butyl-5-methyl-1,3-dihydro-3-[[4-[3-(1H-tetrazol-5-yl)-2-pyridinyl]phenyl]methyl]-2H-imidazol-2-one;

1-cyclohexylmethyl-4-butyl-5-methyl-1,3-dihydro-3-[[4-[3-(1H-tetrazol-5-yl)-2-pyridinyl]phenyl]methyl]-2H-imidazol-2-one;

1-phenylmethyl-4-butyl-5-methyl-1,3-dihydro-3-[[4-[3-(1H-tetrazol-5-yl)-2-pyridinyl]phenyl]methyl]-2H-imidazol-2-one;

1-(2-cyclohexylethyl)-4-butyl-5-methyl-1,3-dihydro-3-[[4-[3-(1H-tetrazol-5-yl)-2-pyridinyl]phenyl]methyl]-2H-imidazol-2-one;

1-(2-phenylethyl)-4-butyl-5-methyl-1,3-dihydro-3-[[4-[3-(1H-tetrazol-5-yl)-2-pyridinyl]phenyl]methyl]-2H-imidazol-2-one;

1-propyl-4-butyl-5-chloro-1,3-dihydro-3-[[4-[3-(1H-tetrazol-5-yl)-2-pyridinyl]phenyl]methyl]-2H-imidazol-2-one;

1,4-dibutyl-5-chloro-1,3-dihydro-3-[[4-[3-(1H-tetrazol-5-yl)-2-pyridinyl]phenyl]methyl]-2H-imidazol-2-one;

1-pentyl-4-butyl-5-chloro-1,3-dihydro-3-[[4-[3-(1H-tetrazol-5-yl)-2-pyridinyl]phenyl]methyl]-2H-imidazol-2-one;

1-isopentyl-4-butyl-5-chloro-1,3-dihydro-3-[[4-[3-(1H-tetrazol-5-yl)-2-pyridinyl]phenyl]methyl]-2H-imidazol-2-one;

1-cyclohexylmethyl-4-butyl-5-chloro-1,3-dihydro-3-[[4-[3-(1H-tetrazol-5-yl)-2-pyridinyl]phenyl]methyl]-2H-imidazol-2-one;

1-phenylmethyl-4-butyl-5-chloro-1,3-dihydro-3-[[4-[3-(1H-tetrazol-5-yl)-2-pyridinyl]phenyl]methyl]-2H-imidazol-2-one;

1-(2-cyclohexylethyl)-4-butyl-5-chloro-1,3-dihydro-3-[[4-[3-(1H-tetrazol-5-yl)-2-pyridinyl]phenyl]methyl]-2H-imidazol-2-one;

and 1-(2-phenylethyl)-4-butyl-5-chloro-1,3-dihydro-3-[[4-[3-(1H-tetrazol-5-yl)-2-pyridinyl]phenyl]methyl]-2H-imidazol-2-one.

Within Formula I there is fourth a sub-class of compounds of high interest as represented by Formula V:

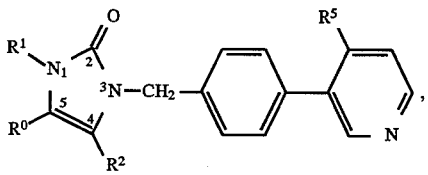

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

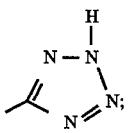

or a tautomer thereof or a pharmaceutically-acceptable salt thereof.

A family of specific compounds of particular interest within Formula V consists of compounds and pharmaceutically-acceptable salts thereof as follows:

1-methyl-4-propyl-1,3-dihydro-3-[[4-[4-(1H-tetrazol-5-yl)-3-pyridinyl]phenyl]methyl]-2H-imidazol-2-one;

1-ethyl-4-propyl-1,3-dihydro-3-[[4-[4-(1H-tetrazol-5-yl)-3-pyridinyl]phenyl]methyl]-2H-imidazol-2-one;

1,4-dipropyl-1,3-dihydro-3-[[4-[4-(1H-tetrazol-5-yl)-3-pyridinyl]phenyl]methyl]-2H-imidazol-2-one;

1-isopropyl-4-propyl-1,3-dihydro-3-[[4-[4-(1H-tetrazol-5-yl)-3-pyridinyl]phenyl]methyl]-2H-imidazol-2-one;

1-butyl-4-propyl-1,3-dihydro-3-[[4-[4-(1H-tetrazol-5-yl)-3-pyridinyl]phenyl]methyl]-2H-imidazol-2-one;

1-secbutyl-4-propyl-1,3-dihydro-3-[[4-[4-(1H-tetrazol-5-yl)-3-pyridinyl]phenyl]methyl]-2H-imidazol-2-one;

1-isobutyl-4-propyl-1,3-dihydro-3-[[4-[4-(1H-tetrazol-5-yl)-3-pyridinyl]phenyl]methyl]-2H-imidazol-2-one;

1-tertbutyl-4-propyl-1,3-dihydro-3-[[4-[4-(1H-tetrazol-5-yl)-3-pyridinyl]phenyl]methyl]-2H-imidazol-2-one;

1-pentyl-4-propyl-1,3-dihydro-3-[[4-[4-(1H-tetrazol-5-yl)-3-pyridinyl]phenyl]methyl]-2H-imidazol-2-one;

1-isopentyl-4-propyl-1,3-dihydro-3-[[4-[4-(1H-tetrazol-5-yl)-3-pyridinyl]phenyl]methyl]-2H-imidazol-2-one;

1-cyclohexyl-4-propyl-1,3-dihydro-3-[[4-[4-(1H-tetrazol-5-yl)-3-pyridinyl]phenyl]methyl]-2H-imidazol-2-one;

1-cyclohexylmethyl-4-propyl-1,3-dihydro-3-[[4-[4-(1H-tetrazol-5-yl)-3-pyridinyl]phenyl]methyl]-2H-imidazol-2-one;

1-phenyl-4-propyl-1,3-dihydro-3-[[4-[4-(1H-tetrazol-5-yl)-3-pyridinyl]phenyl]methyl]-2H-imidazol-2-one;

1-phenylmethyl-4-propyl-1,3-dihydro-3-[[4-[4-(1H-tetrazol-5-yl)-3-pyridinyl]phenyl]methyl]-2H-imidazol-2-one;

1-(2-cyclohexylethyl)-4-propyl-1,3-dihydro-3-[[4-[4-(1H-tetrazol-5-yl)-3-pyridinyl]phenyl]methyl]-2H-imidazol-2-one;

1-(2-phenylethyl)-4-propyl-1,3-dihydro-3-[[4-[4-(1H-tetrazol-5-yl)-3-pyridinyl]phenyl]methyl]-2H-imidazol-2-one;

1-methyl-4-butyl-1,3-dihydro-3-[[4-[4-(1H-tetrazol-5-yl)-3-pyridinyl]phenyl]methyl]-2H-imidazol-2-one;

1-ethyl-4-butyl-1,3-dihydro-3-[[4-[4-(1H-tetrazol-5-yl)-3-pyridinyl]phenyl]methyl]-2H-imidazol-2-one;

1-propyl-4-butyl-1,3-dihydro-3-[[4-[4-(1H-tetrazol-5-yl)-3-pyridinyl]phenyl]methyl]-2H-imidazol-2-one;

1-isopropyl-4-butyl-1,3-dihydro-3-[[4-[4-(1H-tetrazol-5-yl)-3-pyridinyl]phenyl]methyl]-2H-imidazol-2-one;

1,4-dibutyl-1,3-dihydro-3-[[4-[4-(1H-tetrazol-5-yl)-3-pyridinyl]phenyl]methyl]-2H-imidazol-2-one;

1-secbutyl-4-butyl-1,3-dihydro-3-[[4-[4-(1H-tetrazol-5-yl)-3-pyridinyl]phenyl]methyl]-2H-imidazol-2-one;

1-isobutyl-4-butyl-1,3-dihydro-3-[[4-[4-(1H-tetrazol-5-yl)-3-pyridinyl]phenyl]methyl]-2H-imidazol-2-one;

1-tertbutyl-4-butyl-1,3-dihydro-3-[[4-[4-(1H-tetrazol-5-yl)-3-pyridinyl]phenyl]methyl]-2H-imidazol-2-one;

1-pentyl-4-butyl-1,3-dihydro-3-[[4-[4-(1H-tetrazol-5-yl)-3-pyridinyl]phenyl]methyt]-2H-imidazol-2-one;

1-isopentyl-4-butyl-1,3-dihydro-3-[[4-[4-(1H-tetrazol-5-yl)-3-pyridinyl]phenyl]methyl]-2H-imidazol-2-one;

1-cyclohexyl-4-butyl-1,3-dihydro-3-[[4-[4-(1H-tetrazol-5-yl)-3-pyridinyl]phenyl]methyl]-2H-imidazol-2-one;

1-cyclohexylmethyl-4-butyl-1,3-dihydro-3-[[4-[4-(1H-tetrazol-5-yl)-3-pyridinyl]phenyl]methyl]-2H-imidazol-2-one;

1-phenyl-4-butyl-1,3-dihydro-3-[[4-[4-(1H-tetrazol-5-yl)-3-pyridinyl]phenyl]methyl]-2H-imidazol-2-one;

1-phenylmethyl-4-butyl-1,3-dihydro-3-[[4-[4-(1H-tetrazol-5-yl)-3-pyridinyl]phenyl]methyl]-2H-imidazol-2-one;

1- (2-cyclohexylethyl)-4-butyl-1,3-dihydro-3-[[4-[4-(1H-tetrazol-5-yl)-3-pyridinyl]phenyl]methyl]-2H-imidazol-2-one;

1-(2-phenylethyl)-4-butyl-1,3-dihydro-3-[[4-[4-(1H-tetrazol-5-yl)-3-pyridinyl]phenyl]methyl]-2H-imidazol-2-one;

1-methyl-4-pentyl-1,3-dihydro-3-[[4-[4-(1H-tetrazol-5-yl)-3-pyridinyl]phenyl]methyl]-2H-imidazol-2-one;

1-ethyl-4-pentyl-1,3-dihydro-3-[[4-[4-(1H-tetrazol-5-yl)-3-pyridinyl]phenyl]methyl]-2H-imidazol-2-one;

1-propyl-4-pentyl-1,3-dihydro-3-[[4-[4-(1H-tetrazol-5-yl)3-pyridinyl]phenyl]methyl]-2H-imidazol-2-one;

1-isopropyl-4-pentyl-1,3-dihydro-3-[[4-[4-(1H-tetrazol-5-yl)-3-pyridinyl]phenyl]methyl]-2H-imidazol-2-one;

1-butyl-4-pentyl-1,3-dihydro-3-[[4-[4-(1H-tetrazol-5-yl)-3-pyridinyl]phenyl]methyl]-2H-imidazol-2-one;

1-secbutyl-4-pentyl-1,3-dihydro-3-[[4-[4-(1H-tetrazol-5-yl)-3-pyridinyl]phenyl]methyl]-2H-imidazol-2-one;

1-isobutyl-4-pentyl-1,3-dihydro-3-[[4-[4-(1H-tetrazol-5-yl)-3-pyridinyl]phenyl]methyl]-2H-imidazol-2 -one;

1-tertbutyl-4-pentyl-1,3-dihydro-3-[[4-[4-(1H-tetrazol-5-yl)-3-pyridinyl]phenyl]methyl]-2H- imidazol-2 -one;

1,4-dipentyl-1,3-dihydro-3-[[4-[4-(1H-tetrazol-5-yl)-3-pyridinyl]phenyl]methyl]-2H-imidazol-2-one;

1-isopentyl-4-pentyl-1,3-dihydro-3-[[4-[4-(1H-tetrazol-5-yl)-3-pyridinyl]phenyl]methyl]-2H-imidazol-2-one;

1-cyclohexyl-4-pentyl-1,3-dihydro-3-[[4-[4-(1H-tetrazol-5-yl)-3-pyridinyl]phenyl]methyl]-2H-imidazol-2-one;

1-cyclohexylmethyl-4-pentyl-1,3-dihydro-3-[[4-[4-(1H-tetrazol-5-yl)-3-pyridinyl]phenyl]methyl]-2H-imidazol-2-one;

1-phenyl-4-pentyl-1,3-dihydro-3-[[4-[4-(1H-tetrazol-5-yl)-3-pyridinyl]phenyl]methyl]-2H-imidazol-2-one;

1-phenylmethyl-4-pentyl-1,3-dihydro-3-[[4-[4-(1H-tetrazol-5-yl)-3-pyridinyl]phenyl]methyl]-2H-imidazol-2-one;

1-(2-cyclohexylethyl)-4-pentyl-1,3-dihydro-3-[[4-[4-(1H-tetrazol-5-yl)-3-pyridinyl]phenyl]methyl]-2H- imidazol-2-one;

1- (2-phenylethyl)-4-pentyl-1,3-dihydro-3-[[4-[4-(1H-tetrazol-5-yl)-3-pyridinyl]phenyl]methyl]-2H-imidazol-2-one;

1-methyl-4-propyl-5-methyl-1,3-dihydro-3-[[4-[4-(1H-tetrazol-5-yl)-3-pyridinyl]phenyl]methyl]-2H-imidazol-2-one;

1-ethyl-4-propyl-5-methyl-1,3-dihydro-3-[[4-[4-(1H-tetrazol-5-yl)-3-pyridinyl]phenyl]methyl]-2H-imidazol-2-one;

1,4-dipropyl-5-methyl-1,3-dihydro-3-[[4-[4-(1H-tetrazol-5-yl)-3-pyridinyl]phenyl]methyl]-2H-imidazol-2-one;

1-isopropyl-4-propyl-5-methyl-1,3-dihydro-3-[[4-[4-(1H-tetrazol-5-yl)-3-pyridinyl]phenyl]methyl]-2H-imidazol-2-one;

1-butyl-4-propyl-5-methyl-1,3-dihydro-3-[[4-[4-(1H-tetrazol-5-yl)-3-pyridinyl]phenyl]methyl]-2H-imidazol-2-one;

1-secbutyl-4-propyl-5-methyl-1,3-dihydro-3-[[4-[4-(1H-tetrazol-5-yl)-3-pyridinyl]phenyl]methyl]-2H-imidazol-2-one;

1-isobutyl-4-propyl-5-methyl-1,3-dihydro-3-[[4-[4-(1H-tetrazol-5-yl)-3-pyridinyl]phenyl]methyl]-2H-imidazol-2-one;

1-tertbutyl-4-propyl-5-methyl-1,3-dihydro-3-[[4-[4-(1H-tetrazol-5-yl)-3-pyridinyl]phenyl]methyl]-2H-imidazol -2-one;

1-pentyl-4-propyl-5-methyl-1,3-dihydro-3-[[4-[4-(1H-tetrazol-5-yl)-3-pyridinyl]phenyl]methyl]-2H-imidazol-2-one;

1-isopentyl-4-propyl-5-methyl-1,3-dihydro-3-[[4-[4-(1H-tetrazol-5-yl)-3-pyridinyl]phenyl]methyl]-2H-imidazol-2-one;

1-cyclohexyl-4-propyl-5-methyl-1,3-dihydro-3-[[4-[4-(1H-tetrazol-5-yl)-3-pyridinyl]phenyl]methyl]-2H-imidazol-2-one;

1-cyclohexylmethyl-4-propyl-5-methyl-1,3-dihydro-3-[[4-[4-(1H-tetrazol-5-yl)-3-pyridinyl]phenyl]methyl]-1H-imidazol-2-one;

1-phenyl-4-propyl-5-methyl-1,3-dihydro-3-[[4-[4-(1H-tetrazol-5-yl)-3-pyridinyl]phenyl]methyl]-2H-imidazol-2-one;

1-phenylmethyl-4-propyl-5-methyl-1,3-dihydro-3-[[4-[4-(1H-tetrazol-5-yl)-3-pyridinyl]phenyl]methyl]-2H-imidazol-2-one;

1-(2-cyclohexylethyl)-4-propyl-5-methyl-1,3-dihydro-3-[[4-[4-(1H-tetrazol-5-yl)-3-pyridinyl]phenyl]methyl]-2H-imidazol-2-one;

1-(2-phenylethyl)-4-propyl-5-methyl-1,3-dihydro-3-[[4-[4-(1H-tetrazol-5-yl)-3-pyridinyl]phenyl]methyl]-2H-imidazol-2-one;

1,5-dimethyl-4-butyl-1,3-dihydro-3-[[4-[4-(1H-tetrazol-5-yl)-3-pyridinyl]phenyl]methyl]-2H-imidazol-2-one;

1-ethyl-4-butyl-5-methyl-1,3-dihydro-3-[[4-[4-(1H-tetrazol-5-yl)-3-pyridinyl]phenyl]methyl]-2H-imidazol-2-one;

1-propyl-4-butyl-5-methyl-1,3-dihydro-3-[[4-[4-(1H-tetrazol-5-yl)-3-pyridinyl]phenyl]methyl]-2H- imidazol-2-one;

1-isopropyl-4-butyl-5-methyl-1,3-dihydro-3-[[4-[4-(1H-tetrazol-5-yl)-3-pyridinyl]phenyl]methyl]-2H-imidazol-2-one;

1,4-dibutyl-5-methyl-1,3-dihydro-3-[[4-[4-(1H-tetrazol-5-yl)-3-pyridinyl]phenyl]methyl]-2H-imidazol-2 -one;

1-secbutyl-4-butyl-5-methyl-1,3-dihydro-3-[[4-[4-(1H-tetrazol-5-yl)-3-pyridinyl]phenyl]methyl]-2H-imidazol-2-one;

1-isobutyl-4-butyl-5-methyl-1,3-dihydro-3-[[4-[4-(1H-tetrazol-5-yl)-3-pyridinyl]phenyl]methyl]-2H-imidazol-2-one;

1-tertbutyl-4-butyl-5-methyl-1,3-dihydro-3-[[4-[4-(1H-tetrazol-5-yl)-3-pyridinyl]phenyl]methyl]-2H-imidazol-2-one;

1-pentyl-4-butyl-5-methyl-1,3-dihydro-3-[[4-[4-(1H-tetrazol-5-yl)-3-pyridinyl]phenyl]methyl]-2H-imidazol-2-one;

1-isopentyl-4-butyl-5-methyl-1,3-dihydro-3-[[4-[4-(1H-tetrazol-5-yl)-3-pyridinyl]phenyl]methyl]-2H-imidazol-2-one;

1-cyclohexyl-4-butyl-5-methyl-1,3-dihydro-3-[[4-[4-(1H-tetrazol-5-yl)-3-pyridinyl]phenyl]methyl]-2H-imidazol-2-one;

1-cyclohexylmethyl-4-butyl-5-methyl-1,3-dihydro-3-[[4-[4-H-tetrazol-5-yl)-3-pyridinyl]phenyl]methyl]-2H-imidazol-2-one;

1-phenyl-4-butyl-5-methyl-1,3-dihydro-3-[[4-[4-(1H-tetrazol-5-yl)-3-pyridinyl]phenyl]methyl]-2H-imidazol-2-one;

1-phenylmethyl-4-butyl-5-methyl-1,3-dihydro-3-[[4-[4-(1H-tetrazol-5-yl)-3-pyridinyl]phenyl]methyl]-2H-imidazol-2-one;

1-(2-cyclohexylethyl)-4-butyl-5-methyl-1,3-dihydro-3-[[4-[4-(1H-tetrazol-5-yl)-3-pyridinyl]phenyl]methyl]-2H-imidazol-2-one;

1-(2-phenylethyl)-4-butyl-5-methyl-1,3-dihydro-3-[[4-[4-(1H-tetrazol-5-yl)-3-pyridinyl]phenyl]methyl]-2H-imidazol-2-one;

1-methyl-4-pentyl-5-methyl-1,3-dihydro-3-[[4-4-(1H-tetrazol-5-yl)-3-pyridinyl]phenyl]methyl]-2H-imidazol-2-one;

1-ethyl-4-pentyl-5-methyl-1,3-dihydro-3-[[4-[4-(1H-tetrazol-5-yl)-3-pyridinyl]phenyl]methyl]-2H-imidazol-2-one;

1-propyl-4-pentyl-5-methyl-1,3-dihydro-3-[[4-[4-(1H-tetrazol-5-yl)-3-pyridinyl]phenyl]methyl]-2H-imidazol-2-one;

1-isopropyl-4-pentyl-5-methyl-1,3-dihydro-3-[[4-[4-(1H-tetrazol-5-yl)-3-pyridinyl]phenyl]methyl]-2H-imidazol-2-one;

1-butyl-4-pentyl-5-methyl-1,3-dihydro-3-[[4-[4-(1H-tetrazol-5-yl)-3-pyridinyl]phenyl]methyl]-2H-imidazol-2-one;

1-secbutyl-4-pentyl-5-methyl-1,3-dihydro-3-[[4-[4-(1H-tetrazol-5-yl)-3-pyridinyl]phenyl]methyl]-2H-imidazol-2-one;

1-isobutyl-4-pentyl-5-methyl-1,3-dihydro-3-[[4-[4-(1H-tetrazol-5-yl)-3-pyridinyl]phenyl]methyl]-2H-imidazol-2-one, 1-tertbutyl-4-pentyl-5-methyl-1,3-dihydro-3-[[4-[4-(1H-tetrazol-5-yl)-3-pyridinyl]phenyl]methyl]-2H-imidazol-2-one;

1,4-dipentyl-5-methyl-1,3-dihydro-3-[[4-[4-(1H-tetrazol-5-yl)-3-pyridinyl]phenyl]methyl]-2H-imidazol-2-one;

1-isopentyl-4-pentyl-5-methyl-1,3-dihydro-3-[[4-[4-(1H-tetrazol-5-yl)-3-pyridinyl]phenyl]methyl]-2H-imidazol-2-one;

1-cyclohexyl-4-pentyl-5-methyl-1,3-dihydro-3-[[4-[4-(1H-tetrazol-5-yl)-3-pyridinyl]phenyl]methyl]-2H-imidazol-2-one;

1-cyclohexylmethyt-4-pentyl-5-methyl-1,3-dihydro-3-[[4-[4-(1H-tetrazol-5-yl)-3-pyridinyl]phenyl]methyl]-2H-imidazol-2-one;

1-phenyl-4-pentyl-5-methyl-1,3-dihydro-3-[[4-[4-(1H-tetrazol-5-yl)-3-pyridinyl]phenyl]methyl]-2H-imidazol-2-one;

1-phenylmethyl-4-pentyl-5-methyl-1,3-dihydro-3-[[4-[4-(1H-tetrazol-5-yl)-3-pyridinyl]phenyl]methyl]-2H-imidazol-2-one;

1-(2-cyclohexylethyl)-4-pentyl-5-methyl-1,3-dihydro-3-[[4-[4-(1H-tetrazol-5-yl)-3-pyridinyl]phenyl]methyl]-2H-imidazol-2-one;

1-(2-phenylethyl)-4-pentyl-5-methyl-1,3-dihydro-3-[[4-[4-(1H-tetrazol-5-yl)-3-pyridinyl]phenyl]methyl]-2H-imidazol-2-one;

1-methyl-4-propyl-5-chloro-1,3-dihydro-3-[[4-[4-(1H-tetrazol-5-yl)-3-pyridinyl]phenyl]methyl]-2H-imidazol-2-one;

1-ethyl-4-propyl-5-chloro-1,3-dihydro-3-[[4-[4-(1H-tetrazol-5-yl)-3-pyridinyl]phenyl]methyl]-2H-imidazol-2-one;

1,4-dipropyl-5-chloro-1,3-dihydro-3-[[4-[4-(1H-tetrazol-5-yl)-3-pyridinyl]phenyl]methyl]-2H-imidazol-2-one;

1-isopropyl-4-propyl-5-chloro-1,3-dihydro-3-[[4-[4-(1H-tetrazol-5-yl)-3-pyridinyl]phenyl]methyl]-2H-imidazol-2-one;

1-butyl-4-propyl-5-chloro-1,3-dihydro-3-[[4-[4-(1H-tetrazol-5-yl)-3-pyridinyl]phenyl]methyl]-2H-[midazol-2-one;

1-secbutyl-4-propyl-5-chloro-1,3-dihydro-3-[[4-[4-(1H-tetrazol-5-yl)-3-pyridinyl]phenyl]methyl]-2H-imidazol-2-one;

1-isobutyl-4-propyl-5-chloro-1,3-dihydro-3-[[4-[4-(1H-tetrazol-5-yl)-3-pyridinyl]phenyl]methyl]-2H-imidazol-2-one;

1-tertbutyl-4-propyl-5-chloro-1,3-dihydro-3-[[4-[4-(1H-tetrazol-5-yl)-3-pyridinyl]phenyl]methyl]-2H-imidazol-2-one;

1-pentyl-4-propyl-5-chloro-1,3-dihydro-3-[[4-[4-(1H-tetrazol-5-yl)-3-pyridinyl]phenyl]methyl]-2H-imidazol-2-one;

1-isopentyl-4 -propyl-5-chloro-1,3-dihydro-3-[[4-[4-(1H-tetrazol-5-yl)-3-pyridinyl]phenyl]methyl]-2H-imidazol-2-one;

1-cyclohexyl-4-propyl-5-chloro-1,3-dihydro-3-[[4-[4-(1H-tetrazol-5-yl)-3-pyridinyl]phenyl]methyl]-2H-imidazol-2-one;

1-cyclohexylmethyl- 4-propyl-5-chloro- 1,3-dihydro-3-[[4-[4-(1H-tetrazol-5-yl)-3-pyridinyl]phenyl]methyl]-2H-imidazol-2-one;

1-phenyl-4-propyl-5-chloro-1,3-dihydro-3-[[4-[4-(1H-tetrazol-5-yl)-3-pyridinyl]phenyl]methyl]-2H-imidazol-2-one;

1-phenylmethyl-4-propyl-5-chloro-1,3-dihydro-3-[[4-[4-(1H-tetrazol-5-yl)-3-pyridinyl]phenyl]methyl]-2H-imidazol-2-one;

1-(2-cyclohexylethyl)-4-propyl-5-chloro-1,3-dihydro3-[[4-[4-(1H-tetrazol-5-yl)-3-pyridinyl]phenyl]methyl]-2H-imidazol-2-one;

1-(2-phenylethyl)-4-propyl-5-chloro-1,3-dihydro-3-[[4-[4-(1H-tetrazol-5-yl)-3-pyridinyl]phenyl]methyl]-2H-imidazol-2-one;

1-methyl-4-butyl-5-chloro-1,3-dihydro-3-[[4-[4-(1H-tetrazol-5-yl)-3-pyridinyl]phenyl]methyl]-2H-imidazol-2-one;

1-ethyl-4-butyl-5-chloro-1,3-dihydro-3-[[4-[4-(1H-tetrazol-5-yl)-3-pyridinyl]phenyl]methyl]-2H-imidazol-2-one;

1-propyl-4-butyl-5-chloro-1,3-dihydro-3-[[4-[4-(1H-tetrazol-5-yl)-3-pyridinyl]phenyl]methyl]-2H-imidazol-2-one;

1-isopropyl-4-butyl-5-chloro-1,3-dihydro-3-[[4-[4-(1H-tetrazol-5-yl)-3-pyridinyl]phenyl]methyl]-2H-imidazol-2-one;

1,4-dibutyl-5-chloro-1,3-dihydro-3-[[4-[4-(1H-tetrazol-5-yl)-3-pyridinyl]phenyl]methyl]-2H-imidazol-2-one;

1-secbutyl-4-butyl-5-chloro-1,3-dihydro-3-[[4-[4-(1H-tetrazol-5-yl)-3-pyridinyl]phenyl]methyl]-2H-imidazol-2-one;

1-isobutyl-4-butyl-5-chloro-1,3-dihydro-3-[[4-[4-(1H-tetrazol-5-yl)-3-pyridinyl]phenyl]methyl]-2H-imidazol-2-one;

1-tertbutyl-4-butyl-5-chloro-1,3-dihydro-3-[[4-[4-(1H-tetrazol-5-yl)-3-pyridinyl]phenyl]methyl]-2H-imidazol-2-one;

1-pentyl-4-butyl-5-chloro-1,3-dihydro-3-[[4-[4-(1H-tetrazol-5-yl)-3-pyridinyl]phenyl]methyl]-2H-imidazol-2-one;

1-isopentyl-4-butyl-5-chloro-1,3-dihydro-3-[[4-[4-(1H-tetrazol-5-yl)-3-pyridinyl]phenyl]methyl]-2H-imidazol-2-one;

1-cyclohexyl-4-butyl-5-chloro-1,3-dihydro-3-[[4-[4-(1H-tetrazol-5-yl)-3-pyridinyl]phenyl]methyl]-2H-imidazol-2-one;

1-cyclohexylmethyl-4 -butyl-5-chloro-1,3-dihydro-3-[[4-[4-(1H-tetrazol-5-yl)-3-pyridinyl]phenyl]methyl]-2H-imidazol-2-one;

1-phenyl-4-butyl-5-chloro-1,3-dihydro-3-[[4-[4-(1H-tetrazol-5-yl)-3-pyridinyl]phenyl]methyl]-2H-imidazol-2-one;

1-phenylmethyl-4-butyl-5-chloro-1,3-dihydro-3-[[4-[4-(1H-tetrazol-5-yl)-3-pyridinyl]phenyl]methyl]-2H-imidazol-2-one;

1-(2-cyclohexylethyl)-4-butyl-5-chloro-1,3-dihydro-3-[[4-[4-(1H-tetrazol-5-yl)-3-pyridinyl]phenyl]methyl]-2H-imidazol-2-one;

1-(2-phenylethyl)-4-butyl-5-chloro-1,3-dihydro-3-[[4-[4-(1H-tetrazol-5-yl)-3-pyridinyl]phenyl]methyl]-2H-imidazol-2-one;

1-methyl-4-pentyl-5-chloro-1,3-dihydro-3-[[4-[4-(1H-tetrazol-5-yl)-3-pyridinyl]phenyl]methyl]-2H-imidazol-2-one;

1-ethyl-4-pentyl-5-chloro-1,3-dihydro-3-[[4- [4-(1H-tetrazol-5-yl)-3-pyridinyl]phenyl]methyl]-2H-imidazol-2-one;

1-propyl-4-pentyl-5-chloro-1,3-dihydro-3-[[4-[4-(1H-tetrazol-5-yl)-3-pyridinyl]phenyl]methyl]-2H-imidazol-2-one;

1-isopropyl-4-pentyl-5-chloro-1,3-dihydro-3-[[4- [4-(1H-tetrazol-5-yl)-3-pyridinyl]phenyl]methyl]-2H-imidazol-2-one;

1-butyl-4-pentyl-5-chloro-1,3-dihydro-3-[[4-[4-(1H-tetrazol-5-yl)-3-pyridinyl]phenyl]methyl]-2H-imidazol-2-one;

1-secbutyl-4-pentyl-5-chloro-1,3-dihydro-3-[[4-[4-(1H-tetrazol-5-yl)-3-pyridinyl]phenyl]methyl]-2H-imidazol-2-one;

1-isobutyl-4-pentyl-5-chloro-1,3-dihydro-3-1-[[4-[4-(1H-tetrazol-5-yl)-3-pyridinyl]phenyl]methyl]-2H-imidazol-2-one;

1-tertbutyl-4-pentyl-5-chloro-1,3-dihydro-3-[[4-[4-{1H-tetrazol-5-yl)-3-pyridinyl]phenyl]methyl]-2H-imidazol-2-one;

1,4-dipentyl-5-chloro-1,3-dihydro-3-[[4-[4-(1H-tetrazol-5-yl)-3-pyridinyl]phenyl]methyl]-2H-imidazol-2-one;

1-isopentyl-4-pentyl-5-chloro-1,3-dihydro-3-[[4-[4-(1H-tetrazol-5-yl)-3-pyridinyl]phenyl]methyl]-2H-imidazol-2-one;

1-cyclohexyl-4-pentyl-5-chloro-1,3-dihydro-3-[[4-[4-(1H-tetrazol-5-yl)-3-pyridinyl]phenyl]methyl]-2H-imidazol-2-one;

1-cyclohexylmethyl-4-pentyl-5-chloro-1,3-dihydro-3-[[4-[4-(1H-tetrazol-5-yl)-3-pyridinyl]phenyl]methyl]-2H-imidazol-2-one;

1-phenyl-4-pentyl-5-chloro-1,3-dihydro-3-[[4-[4-(1H-tetrazol-5-yl)-3-pyridinyl]phenyl]methyl]-2H-imidazol-2-one;

1-phenylmethyl-4-pentyl-5-chloro-1,3-dihydro-3-[[4-[4-(1H-tetrazol-5-yl)-3-pyridinyl]phenyl]methyl]-2H-imidazol-2-one;

1-(2-cyclohexylethyl)-4-pentyl-5-chloro-1,3-dihydro-3-[[4-[4-(1H-tetrazol-5-yl)-3-pyridinyl]phenyl]methyl]-2H-imidazol-2-one;

and 1-(2-phenylethyl)-4-pentyl-5-chloro-1,3-dihydro-3-[[4-[4-(1H-tetrazol-5-yl)-3-pyridinyl]phenyl]methyl]-1H-imidazol-2-one.

A family of compounds of more particular interest within Formula V consists of compounds and pharmaceutically-acceptable salts thereof as follows: 1-propyl-4-butyl-1,3-dihydro-3-[[4-[4-(1H-tetrazol-5-yl)-3-pyridinyl]phenyl]methyl]-2H-imidazol-2-one;

1,4-dibutyl-1,3-dihydro-3-[[4-[4-(1H-tetrazol-5-yl)-3-pyridinyl]phenyl]methyl]-2H-imidazol-2-one;

1-entyl-4-butyl-1,3-dihydro-3-[[4-[4-(1H-tetrazol-5-yl)-3-pyridinyl]phenyl]methyl]-2H-imidazol-2-one;

1-isopentyl-4-butyl-1,3-dihydro-3-[[4-[4-(1H-tetrazol-5-yl)-3-pyridinyl]phenyl]methyl]-2H-imidazol-2-one;

1-cyclohexylmethyl-4-butyl-1,3-dihydro-3-[[4-[4-(1H-tetrazol-5-yl)-3-pyridinyl]phenyl]methyl]-2H-imidazol-2-one;

1-phenylmethyl-4-butyl-1,3-dihydro-3-[[4-[4-(1H-tetrazol-5-yl}-3-pyridinyl]phenyl]methyl]-2H-imidazol-2-one;

1-(2-cyclohexylethyl)-4-butyl-1,3-dihydro-3-[[4-[4-(1H-tetrazol-5-yl)-3-pyridinyl]phenyl]methyl]-2H-imidazol-2-one;

1-(2-phenylethyl)-4-butyl-1,3-dihydro-3-[[4-[4-(1H-tetrazol-5-yl)-3-pyridinyl]phenyl]methyl]-2H-imidazol-2-one;

1-propyl-4-butyl-5-methyl-1,3-dihydro-3-[[4-[4-(1H-tetrazol-5-yl)-3-pyridinyl]phenyl]methyl]-2H-imidazol-2-one;

1,4-dibutyl-5-methyl-1,3-dihydro-3-[[4-[4-(1H-tetrazol-5-yl)-3-pyridinyl]phenyl]methyl]-2H-imidazol-2-one;

1-pentyl-4-butyl-5-methyl-1,3-dihydro-3-[[4-[4-(1H-tetrazol-5-yl)-3-pyridinyl]phenyl]methyl]-2H-imidazol-2-one;

1-isopentyl-4-butyl-5-methyl-1,3-dihydro-3-[[4-[4-(1H-tetrazol-5-yl)=3-pyridinyl]phenyl]methyl]-2H-imidazol-2-one;

1-cyclohexylmethyl-4-butyl-5-methyl-1,3-dihydro-3-[[4-[4-(1H-tetrazol-5-yl)-3-pyridinyl]phenyl]methyl]-2H-imidazol-2-one;

1-phenylmethyl-4-butyl-5-methyl-1,3-dihydro-3-[[4-[4-(1H-tetrazol-5-yl)-3-pyridinyl]phenyl]methyl]-2H-imidazol-2-one;

1-(2-cyclohexylethyl)-4-butyl-5-methyl-1,3-dihydro-3-[[4-[4-(1H-tetrazol-5-yl)-3-pyridinyl]phenyl]methyl]-2H-imidazol-2-one;

1(2-phenylethyl)-4-butyl-5-methyl-1,3-dihydro-3-[[4-[4-(1H-tetrazol-5-yl)-3-pyridinyl]phenyl]methyl]-2H-imidazol-2-one;

1-propyl-4-butyl-5-chloro-1,3-dihydro-3-[[4-[4-(1H-tetrazol-5-yl)-3-pyridinyl]phenyl]methyl]-2H-imidazol-2-one;

1,4-dibutyl-5-chloro-1,3-dihydro-3-[[4-[4-(1H-tetrazol-5-yl)-3-pyridinyl]phenyl]methyl]-2H-imidazol-2-one;

1-pentyl-4-butyl-5-chloro-1,3-dihydro-3-[[4-[4-(1H-tetrazol-5-yl)-3-pyridinyl]phenyl]methyl]-2H-imidazol-2-one;

1-isopentyl-4-butyl-5-chloro-1,3-dihydro-3-[[4-[4 -(1H-tetrazol-5-yl)-3-pyridinyl]phenyl]methyl]-2H-imidazol-2-one;

1-cyclohexylmethyl-4-butyl-5-chloro-1,3-dihydro-3-[[4-[4-(1H-tetrazol-5-yl)-3-pyridinyl]phenyl]methyl]-2H-imidazol-2-one;

1-phenylmethyl-4-butyl-5-chloro-1,3-dihydro-3-[[4-[4-(1H-tetrazol-5-yl)-3-pyridinyl]phenyl]methyl]-2H-imidazol-2-one;

1(2-cyclohexylethyl)-4-butyl-5-chloro-1,3-dihydro-3-[[4-4-(1H-tetrazol-5-yl)-3-pyridinyl]phenyl]methyl]-2H-imidazol-2-one;

and 1-(2-phenylethyl)-4-butyl-5-chloro-1,3-dihydro-3-[[4-[4-(1H-tetrazol-5-yl)-3-pyridinyl]phenyl]methyl]-2H-imidazol-2-one.

Within Formula I there is fifth sub-class of compounds of high interest as represented by Formula VI:

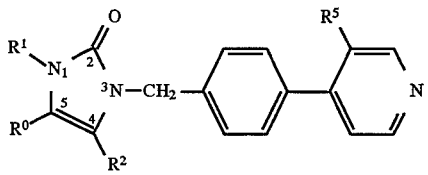 (VI)

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

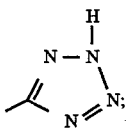

or a tautomer thereof or a pharmaceutically-acceptable salt thereof.

A family of specific compounds of particular interest within Formula VI consists of compounds and pharmaceutically-acceptable salts thereof as follows:

1-methyl-4-propyl-1,3-dihydro-3-[[4-[3-(1H-tetrazol-5-yl)-4-pyridinyl]phenyl]methyl]-2H-imidazol-2-one;
1-ethyl-4-propyl-1,3-dihydro-3-[[4-[3-(1H-tetrazol-5-yl)-4-pyridinyl]phenyl]methyl]-2H-imidazol-2-one;
1,4-dipropyl-1,3-dihydro-3-[[4-[3-(1H-tetrazol-5-yl)-4-pyridinyl]phenyl]methyl]-2H-imidazol-2-one;
1-isopropyl-4-propyl-1,3-dihydro-3-[[4-[3-(1H-tetrazol-5-yl)-4-pyridinyl]phenyl]methyl]-2H-imidazol-2-one;
1-butyl-4-propyl-1,3-dihydro-3-[[4-[3-(1H-tetrazol-5-yl)-4-pyridinyl]phenyl]methyl]-2H-imidazol-2-one;
1-secbutyl-4-propyl-1,3-dihydro-3-[[4-[3-(1H-tetrazol-5-yl)-4-pyridinyl]phenyl]methyl]-2H-imidazol-2-one;
1-isobutyl-4-propyl-1,3-dihydro-3-[[4-[3-(1H-tetrazol-5-yl)-4-pyridinyl]phenyl]methyl]-2H-imidazol-2-one;
1-tertbutyl-4-propyl-1,3-dihydro-3-[[4-[3-(1H-tetrazol-5-yl)-4-pyridinyl]phenyl]methyl]-2H-imidazol-2-one;
1-pentyl-4-propyl-1,3-dihydro-3-[[4-[3-(1H-tetrazol-5-yl)-4-pyridinyl]phenyl]methyl]-2H-imidazol-2-one;
1-isopentyl-4-propyl-1,3-dihydro-3-[[4-[3-(1H-tetrazol-5-yl)-4-pyridinyl]phenyl]methyl]-2H-imidazol-2-one;
1-cyclohexyl-4-propyl-1,3-dihydro-3-[[4-[3-(1H-tetrazol-5-yl)-4-pyridinyl]phenyl]methyl]-2H-imidazol-2-one;
1-cyclohexylmethyl-4-propyl-1,3-dihydro-3-[[4-[3-(1H-tetrazol-5-yl)-4-pyridinyl]phenyl]methyl]-2H-imidazol-2-one;
1-phenyl-4-propyl-1,3-dihydro-3-[[4-[3-(1H-tetrazol-5-yl)-4-pyridinyl]phenyl]methyl]-2H-imidazol-2-one;
1-phenylmethyl-4-propyl-1,3-dihydro-3-[[4-[3-(1H-tetrazol-5-yl)-4-pyridinyl]phenyl]methyl]-2H-imidazol-2-one;
1-(2-cyclohexylethyl)-4-propyl-1,3-dihydro-3-[[4-[3-(1H-tetrazol-5-yl)-4-pyridinyl]phenyl]methyl]-2H-imidazol-2-one;
1-(2-phenylethyl)-4-propyl-1,3-dihydro-3-[[4-[3-(1H-tetrazol-5-yl)-4-pyridinyl]phenyl]methyl]-2H-imidazol-2-one;
1-methyl-4-butyl-1,3-dihydro-3-[[4-[3-(1H-tetrazol-5-yl)-4-pyridinyl]phenyl]methyl]-2H-imidazol-2-one;
1-ethyl-4-butyl-1,3-dihydro-3-[[4-[3-(1H-tetrazol-5-yl)-4-pyridinyl]phenyl]methyl]-2H-imidazol-2-one;
1-propyl-4-butyl-1,3-dihydro-3-[[4-[3-(1H-tetrazol-5-yl)-4-pyridinyl]phenyl]methyl]-2H-imidazol-2-one;
1-isopropyl-4-butyl-1,3-dihydro-3-[[4-[3-(1H-tetrazol-5-yl)-4-pyridinyl]phenyl]methyl]-2H-imidazol-2-one;
1,4-dibutyl-1,3-dihydro-3-[[4-[3-(1H-tetrazol-5-yl)-4-pyridinyl]phenyl]methyl]-2H-imidazol-2-one;
1-secbutyl-4-butyl-1,3-dihydro-3-[[4-[3-(1H-tetrazol-5-yl)-4-pyridinyl]phenyl]methyl]-2H-imidazol-2-one;
1-isobutyl-4-butyl-1,3-dihydro-3-[[4-[3-(1H-tetrazol-5-yl)-4-pyridinyl]phenyl]methyl]-2H-imidazol-2-one;
1-tertbutyl-4-butyl-1,3-dihydro-3-[[4-[3-(1H-tetrazol-5-yl)-4-pyridinyl]phenyl]methyl]-2H-imidazol-2-one;
1-pentyl-4-butyl-1,3-dihydro-3-[[4-[3-(1H-tetrazol-5-yl)-4-pyridinyl]phenyl]methyl]-2H-imidazol-2-one;
1-isopentyl-4-butyl-1,3-dihydro-3-[[4-[3-(1H-tetrazol-5-yl)-4-pyridinyl]phenyl]methyl]-2H-imidazol-2-one;
1-cyclohexyl-4-butyl-1,3-dihydro-3-[[4-[3-(1H-tetrazol-5-yl)-4-pyridinyl]phenyl]methyl]-2H-imidazol-2-one;
1-cyclohexylmethyl-4-butyl-1,3-dihydro-3-[[4-[3-(1H-tetrazol-5-yl)-4-pyridinyl]phenyl]methyl]-2H-imidazol-2-one;
1-phenyl-4-butyl-1,3-dihydro-3-[[4-[3-(1H-tetrazol-5-yl)-4-pyridinyl]phenyl]methyl]-2H-imidazol-2-one;
1-phenylmethyl-4-butyl-1,3-dihydro-3-[[4-[3-(1H-tetrazol-5-yl)-4-pyridinyl]phenyl]methyl]-2H-imidazol-2-one;
1-(2-cyclohexylethyl)-4-butyl-1,3-dihydro-3-[[4-[3-(1H-tetrazol-5-yl)-4-pyridinyl]phenyl]methyl]-2H-imidazol-2-one;
1(2-phenylethyl)-4-butyl-1,3-dihydro-3-[[4-[3-(1H-tetrazol-5-yl)-4-pyridinyl]phenyl]methyl]-2H-imidazol-2-one;
1-methyl-4-pentyl-1,3-dihydro-3-[[4-[3-(1H-tetrazol-5-yl)-4-pyridinyl]phenyl]methyl]-2H-imidazol-2-one;
1-ethyl-4-pentyl-1,3-dihydro-3-[[4-[3-(1H-tetrazol-5-yl)-4-pyridinyl]phenyl]methyl]-2H-imidazol-2-one;
1-propyl-4-pentyl-1,3-dihydro-3-[[4-[3-(1H-tetrazol-5-yl)-4-pyridinyl]phenyl]methyl]-2H-imidazol-2-one;
1-isopropyl-4-pentyl-1,3-dihydro-3-[[4-[3-(1H-tetrazol-5-yl)-4-pyridinyl]phenyl]methyl]-2H-imidazol-2-one;
1-butyl-4-pentyl-1,3-dihydro-3-[[4-[3-(1H-tetrazol-5-yl)-4-pyridinyl]phenyl]methyl]-2H-imidazol-2-one;
1-secbutyl-4-pentyl-1,3-dihydro-3-[[4-[3-(1H-tetrazol-5-yl)-4-pyridinyl]phenyl]methyl]-2H-imidazol-2-one;
1-isobutyl-4-pentyl-1,3-dihydro-3-[[4-[3-(1H-tetrazol-5-yl)-4-pyridinyl]phenyl]methyl]-2H-imidazol-2-one;
1-tertbutyl-4-pentyl-1,3-dihydro-3-[[4-[3-(1H-tetrazol-5-yl)-4-pyridinyl]phenyl]methyl]-2H-imidazol-2-one;
1,4-dipentyl-1,3-dihydro-3-[[4-[3-(1H-tetrazol-5-yl)-4-pyridinyl]phenyl]methyl]-2H-imidazol-2-one;
1-isopentyl-4-pentyl-1,3-dihydro-3-[[4-[3-(1H-tetrazol-5-yl)-4-pyridinyl]phenyl]methyl]-2H-imidazol-2-one;
1-cyclohexyl-4-pentyl-1,3-dihydro-3-[[4-[3-(1H-tetrazol-5-yl)-4-pyridinyl]phenyl]methyl]-2H-imidazol-2-one;
1-cyclohexylmethyl-4-pentyl-1,3-dihydro-3-[[4-[3-(1H-tetrazol-5-yl)-4-pyridinyl]phenyl]methyl]-2H-imidazol-2-one;
1-phenyl-4-pentyl-1,3-dihydro-3-[[4-[3-(1H-tetrazol-5-yl)-4-pyridinyl]phenyl]methyl]-2H-imidazol-2-one;
1-phenylmethyl-4-pentyl-1,3-dihydro-3-[[4-[3-(1H-tetrazol-5-yl)-4-pyridinyl]phenyl]methyl]-2H-imidazol-2-one;

1-(2-cyclohexylethyl)-4-pentyl-1,3-dihydro-3-[[4-[3-(1H-tetrazol-5-yl)-4-pyridinyl]phenyl]methyl]-2H-imidazol-2-one;

1-(2-phenylethyl)-4-pentyl-1,3-dihydro-3-[[4-[3-(1H-tetrazol-5-yl)-4-pyridinyl]phenyl]methyl]-2H-imidazol-2-one;

1,5-methyl-4-propyl-1,3-dihydro-3-[[4-[3-(1H-tetrazol-5-yl)-4-pyridinyl]phenyl]methyl]-2H-imidazol-2-one;

1-ethyl-4-propyl-5-methyl-1,3-dihydro-3-[[4-[3-(1H-tetrazol-5-yl)-4-pyridinyl]phenyl]methyl]-2H-imidazol-2-one;

1,4-dipropyl-5-methyl-1,3-dihydro-3-[[4-[3-(1H-tetrazol-5-yl)-4-pyridinyl]phenyl]methyl]-2H-imidazol-2-one;

1-isopropyl-4-propyl-5-methyl-1,3-dihydro-3-[[4-[3-(1H-tetrazol-5-yl)-4-pyridinyl]phenyl]methyl]-2H-imidazol-2-one;

1-butyl-4-propyl-5-methyl-1,3-dihydro-3-[[4-[3-(1H-tetrazol-5-yl)-4-pyridinyl]phenyl]methyl]-2H-imidazol-2-one;

1-secbutyl-4-propyl-5-methyl-1,3-dihydro-3-[[4-[3-(1H-tetrazol-5-yl)-4-pyridinyl]phenyl]methyl]-2H-imidazol-2-one;

1-isobutyl-4-propyl-5-methyl-1,3-dihydro-3-[[4-[3-(1H-tetrazol-5-yl)-4-pyridinyl]phenyl]methyl]-2H-imidazol-2-one;

1-tertbutyl-4-propyl-5-methyl-1,3-dihydro-3-[[4-[3-(1H-tetrazol-5-yl)-4-pyridinyl]phenyl]methyl]-2H-imidazol-2-one;

1-pentyl-4-propyl-5-methyl-1,3-dihydro-3-[[4-[3-(1H-5 tetrazol-5-yl)-4-pyridinyl]phenyl]methyl]-2H-imidazol-2-one;

1-isopentyl-4-propyl-5-methyl-1,3-dihydro-3-[[4-[3-(1H-tetrazol-5-yl)-4-pyridinyl]phenyl]methyl]-2H-imidazol-2-one;

1-cyclohexyl-4-propyl-5-methyl-1,3-dihydro-3-[[4-[3-(1H-tetrazol-5-yl)-4-pyridinyl]phenyl]methyl]-2H-imidazol-2-one;

1-cyclohexylmethyl-4-propyl-5-methyl-1,3-dihydro-3-[[4-[3-(1H-tetrazol-5-yl)-4-pyridinyl]phenyl]methyl]-2H-imidazol-2-one;

1-phenyl-4-propyl-5-methyl-1,3-dihydro-3-[[4-[α-(1H-tetrazol-5-yl)-4-pyridinyl]phenyl]methyl]-2H-imidazol-2-one;

1-phenylmethyl-4-propyl-5-methyl-1,3-dihydro-3-[[4-[3-(1H-tetrazol-5-yl)-4-pyridinyl]phenyl]methyl]-2H-imidazol-2-one;

1-(2-cyclohexylethyl)-4-propyl-5-methyl-1,3-dihydro-3-[[4-3-(1H-tetrazol-5-yl)-4-pyridinyl]phenyl]methyl]-2H-imidazol-2-one;

1-(2-phenylethyl)-4-propyl-5-methyl-1,3-dihydro-3-[[4-[3-(1H-tetrazol-5-yl)-4-pyridinyl]phenyl]methyl]-2H-imidazol-2-one;

1,5-dimethyl-4-butyl-1,3-dihydro-3-[[4-[3-(1H-tetrazol-5-yl)-4-pyridinyl]phenyl]methyl]-2H-imidazol-2-one;

1-ethyl-4-butyl-5-methyl-1,3-dihydro-3-[[4-[3-(1H-tetrazol-5-yl)-4-pyridinyl]phenyl]methyl]-2H-imidazol-2-one;

1-propyl-4-butyl-5-methyl-1,3-dihydro-3-[[4-[3-(1H-tetrazol-5-yl)-4-pyridinyl]phenyl]methyl]-2H-imidazol-2-one;

1-isopropyl-4-butyl-5-methyl-1,3-dihydro-3-[[4-[3-(1H-tetrazol-5-yl)-4-pyridinyl]phenyl]methyl]-2H-imidazol-2-one;

1,4-dibutyl-5-methyl-1,3-dihydro-3-[[4-[3-(1H-tetrazol-5-yl)-4-pyridinyl]phenyl]methyl]-2H-imidazol-2-one;

1-secbutyl-4-butyl-5-methyl-1,3-dihydro-3-[[4-[3-(1H-tetrazol-5-yl)-4-pyridinyl]phenyl]methyl]-2H-imidazol-2-one;

1-isobutyl-4-butyl-5-methyl-1,3-dihydro-3-[[4-[3-(1H-tetrazol-5-yl)-4-pyridinyl]phenyl]methyl]-2H-imidazol-2-one;

1-tertbutyl-4-butyl-5-methyl-1,3-dihydro-3-[[4-[3-(1H-tetrazol-5-yl)-4-pyridinyl]phenyl]methyl]-2H-imidazol-2-one;

1-pentyl-4-butyl-5-methyl-1,3-dihydro-3-[[4-[3-(1H-tetrazol-5-yl)-4-pyridinyl]phenyl]methyl]-2H-imidazol-2-one;

1-isopentyl-4-butyl-5-methyl-1,3-dihydro-3-[[4-[3-(1H-tetrazol-5-yl)-4-pyridinyl]phenyl]methyl]-2H-imidazol-2-one;

1-cyclohexyl-4-butyl-5-methyl-1,3-dihydro-3-[[4-[3-(1H-tetrazol-5-yl)-4-pyridinyl]phenyl]methyl]-2H-imidazol-2-one;

1-cyclohexylmethyl-4-butyl-5-methyl-1,3-dihydro-3-[[4-[3-(1H-tetrazol-5-yl)-4-pyridinyl]phenyl]methyl]-2H-imidazol-2-one;

1-phenyl-4-butyl-5-methyl-1,3-dihydro-3-[[4-[3-(1H-tetrazol-5-yl)-4-pyridinyl]phenyl]methyl]-2H-imidazol-2-one;

1-phenylmethyl-4-butyl-5-methyl-1,3-dihydro-3-[[4-[3-(1H-tetrazol-5-yl)-4-pyridinyl]phenyl]methyl]-2H-imidazol-2-one;

1-(2-cyclohexylethyl)-4-butyl-5-methyl-1,3-dihydro-3-[[4-[3-(1H-tetrazol-5-yl)-4-pyridinyl]phenyl]methyl]-2H-imidazol-2-one;

1-(2-phenylethyl)-4-butyl-5-methyl-1,3-dihydro-3-[[4-[3-(1H-tetrazol-5-yl)-4-pyridinyl]phenyl]methyl]-2H-imidazol-2-one;

1,5-dimethyl-4-pentyl-1,3-dihydro-3-[[4-[3-(1H-tetrazol-5-yl)-4-pyridinyl]phenyl]methyl]-2H-imidazol-2-one;

1-ethyl-4-pentyl-5-methyl-1,3-dihydro-3-[[4-[3-(1H-tetrazol-5-yl)-4-pyridinyl]phenyl]methyl]-2H-imidazol-2-one;

1-propyl-4-pentyl-5-methyl-1,3-dihydro-3-[[4-[3-(1H-tetrazol-5-yl)-4-pyridinyl]phenyl]methyl]-2H-imidazol-2-one;

1-isopropyl-4-pentyl-5-methyl-1,3-dihydro-3-[[4-[3-(1H-tetrazol-5-yl)-4-pyridinyl]phenyl]methyl]-2H-imidazol-2-one;

1-butyl-4-pentyl-5-methyl-1,3-dihydro-3-[[4-[3-(1H-tetrazol-5-yl)-4-pyridinyl]phenyl]methyl]-2H-imidazol-2-one;

1-secbutyl-4-pentyl-5-methyl-1,3-dihydro-3-[[4-[3-(1H-tetrazol-5-yl)-4-pyridinyl]phenyl]methyl]-2H-imidazol-2-one;

1-isobutyl-4-pentyl-5-methyl-1,3-dihydro-3-[[4-[3-(1H-tetrazol-5-yl)-4-pyridinyl]phenyl]methyl]-2H-imidazol-2-one;

1-tertbutyl-4-pentyl-5-methyl-1,3-dihydro-3-[[4-[3-(1H-tetrazol-5-yl)-4-pyridinyl]phenyl]methyl]-2H-imidazol-2-one;

1,4-dipentyl-5-methyl-1,3-dihydro-3-[[4-[3-(1H-tetrazol-5-yl)-4-pyridinyl]phenyl]methyt]-2H-imidazol-2-one;

1-isopentyl-4-pentyl-5-methyl-1,3-dihydro-3-[[4-[3-(1H-tetrazol-5-yl)-4-pyridinyl]phenyl]methyl]-2H-imidazol-2-one;

1-cyclohexyl-4-pentyl-5-methyl-1,3-dihydro-3-[[4-[3-(1H-tetrazoi-5-yl)-4-pyridinyl]phenyl]methyl]-2H-imidazol-2-one;

1-cyclohexylmethyl-4-pentyl-5-methyl-1,3-dihydfo-3-[[4-[3-(1H-tetrazol-5-yl)-4-pyridinyl]phenyl]methyl]-2H-imidazol-2-one;

1-phenyl-4-pentyl-5-methyl-1,3-dihydro-3-[[4-[3-(1H-tetrazol-5-yl)-4-pyridinyl]phenyl]methyl]-2H-imidazol-2-one;

1-phenylmethyl-4-pentyl-5-methyl-1,3-dihydro-3-[[4-[3-(1H-tetrazol-5-yl)-4-pyridinyl]phenyl]methyl]-2H-imidazol-2-one;

1-(2-cyclohexylethyl)-4-pentyl-5-methyl-1,3-dihydro-3-[[4-[3-(1H-tetrazol-5-yl)-4-pyridinyl]phenyl]methyl]-2H-imidazol-2-one;

1-(2-phenylethyl)-4-pentyl-5-methyl-1,3-dihydro-3-[[4-[3-(1H-tetrazol-5-yl)-4-pyridinyl]phenyl]methyl]-2H-imidazol-2-one;

1-methyl-4-propyl-5-chloro-1,3-dihydro-3-[[4-[3-(1H-tetrazol-5-yl)-4-pyridinyl]phenyl]methyl]-2H-imidazol-2-one;

1-ethyl-4-propyl-5-chloro-1,3-dihydro-3-[[4-[3-(1H-tetrazol-5-yl)-4-pyridinyl]phenyl]methyl]-2H-imidazol-2-one;

1,4-dipropyl-5-chloro-1,3-dihydro-3-[[4-[3-(1H-tetrazol-5-yl)-4-pyridinyl]phenyl]methyl]-2H-imidazol-2-one;

1-isopropyl-4-propyl-5-chloro-1,3-dihydro-3-[[4-[3-(1H-tetrazol-5-yl)-4-pyridinyl]phenyl]methyl]-2H-imidazol-2-one;

1-butyl-4-propyl-5-chloro-1,3-dihydro-3-[[4-[3-(1H-tetrazol-5-yl)-4-pyridinyl]phenyl]methyl]-2H-imidazol-2-one;

1-secbutyl-4-propyl-5-chloro-1,3-dihydro-3-[[4-[3-(1H-tetrazol-5-yl) -4-pyridinyl]phenyl]methyl]-2H-imidazol-2-one;

1-isobutyl-4-propyl-5-chloro-1,3-dihydro-3-[[4-[3-(1H-tetrazol-5-yl)-4-pyridinyl]phenyl]methyl]-2H-imidazol-2-one;

1-tertbutyl-4-propyl-5-chloro-1,3-dihydro-3-[[4- [3-(1H-tetrazol-5-yl)-4-pyridinyl]phenyl]methyl]-2H-imidazol-2-one;

1-pentyl-4-propyl-5-chloro-1,3-dihydro-3-[[4-[3-(1H-tetrazol-5-yl)-4-pyridinyl]phenyl]methyl]-2H-imidazol-2-one;

1-isopentyl-4 -propyl-5-chloro-1,3-dihydro-3-[[4-[3-(1H-tetrazol-5-yl)-4-pyridinyl]phenyl]methyl]-2H-imidazol-2-one;

1-cyclohexyl-4-propyl-5-chloro-1,3-dihydro-3-[[4-[3-(1H-tetrazol-5-yl)-4-pyridinyl]phenyl]methyl]-2H-imidazol-2-one;

1-cyclohexylmethyl-4-propyl-5-chloro-1,3-dihydro-3-[[4-[3-(1H-tetrazol-5-yl)-4-pyridinyl]phenyl]methyl]-2H-imidazol-2-one;

2-phenyl-4-propyl-5-chloro-1,3-dihydro-3-[[4-[3-(1H-tetrazol-5-yl)-4-pyridinyl]phenyl]methyl]-2H-imidazol-2-one;

1-phenylmethyl-4-propyl-5-chloro-1,3-dihydro-3-[[4-[3-(1H-tetrazol-5-yl)-4-pyridinyl]phenyl]methyl]-2H-imidazol-2-one;

1-(2-cyclohexylethyl)-4-propyl-5-chloro-1,3-dihydro-3-[[4-3-(1H-tetrazol-5-yl)-4-pyridinyl]phenyl]methyl]-2H-imidazol-2-one;

1-(2-phenylethyl)-4-propyl-5-chloro-1,3-dihydro-3-[[4-[3-(1H-tetrazol-5-yl)-4-pyridinyl]phenyl]methyl]-2H-imidazol-2-one;

1-methyl-4-butyl-5-chloro-1,3-dihydro-3-[[4-[3-(1H-tetrazol-5-yl)-4-pyridinyl]phenyl]methyl]-2H-imidazol-2-one;

1-ethyl-4-butyl-5-chloro-1,3-dihydro-3-[[4-[3-(1H-tetrazol-5-yl)-4-pyridinyl]phenyl]methyl]-2H-imidazol-2-one;

1-propyl-4-butyl-5-chloro-1,3-dihydro-3-[[4-[3-(1H-tetrazol-5-yl)-4-pyridinyl]phenyl]methyl]-2H-imidazol-2-one;

1-isopropyl-4-butyl-5-chloro-1,3-dihydro-3-[[4-[3-(1H-tetrazol-5-yl)-4-pyridinyl]phenyl]methyl]-2H-imidazol-2-one;

1,4-dibutyl-5-chloro-1,3-dihydro-3-[[4-[3-(1H-tetrazol-5-yl)-4-pyridinyl]phenyl]methyl]-2H-imidazol-2-one;

1-secbutyl-4-butyl-5-chloro-1,3-dihydro-3-[[4-[3-(1H-tetrazol-5-yl)-4-pyridinyl]phenyl]methyl]-2H-imidazol-2-one;

1-isobutyl-4-butyl-5-chloro-1,3-dihydro-3-[[4-[3-(1H-tetrazol-5-yl)-4-pyridinyl]phenyl]methyl]-2H-imidazol-2-one;

1-tertbutyl-4-butyl-5-chloro-1,3-dihydro-3-[[4-[3-(1H-tetrazol-5-yl)-4-pyridinyl]phenyl]methyl]-2H-imidazol-2-one;

1-pentyl-4-butyl-5-chloro-1,3-dihydro-3-[[4-[3-(1H-tetrazol-5-yl)-4-pyridinyl]phenyl]methyl]-2H-imidazol-2-one;

1-isopentyl-4-butyl-5-chloro-1,3-dihydro-3-[[4-[3-(1H-tetrazol-5-yl)-4-pyridinyl]phenyl]methyl]-2H-imidazol-2-one;

1-cyclohexyl-4-butyl-5-chloro-1,3-dihydro-3-[[4-[3-(1H-tetrazol-5-yl)-4-pyridinyl]phenyl]methyl]-2H-imidazol-2-one;

1-cyclohexylmethyl-4-butyl-5-chloro-1,3-dihydro-3-[[4-[3-(1H-tetrazol-5-yl)-4-pyridinyl]phenyl]methyl]-2H-imidazol-2-one;

1-phenyl-4-butyl-5-chloro-1,3-dihydro-3-[[4-[3-(1H-tetrazol-5-yl)-4-pyridinyl]phenyl]methyl]-2H-imidazol-2-one;

1-phenylmethyl-4-butyl-5-chloro-1,3-dihydro-3-[[4-[3-(1H-tetrazol-5-yl)-4-pyridinyl]phenyl]methyl]-2H-imidazol-2-one;

1-(2-cyclohexylethyl)-4-butyl-5-chloro-1,3-dihydro-3-[[4-[3-(1H-tetrazol-5-yl)-4-pyridinyl]phenyl]methyl]-2H-imidazol-2-one;

1-(2-phenylethyl)-4-butyl-5-chloro-1,3-dihydro-3-[[4-[3-(1H-tetrazol-5-yl)-4-pyridinyl]phenyl]methyl]-2H-imidazol-2-one;

1-methyl-4-pentyl-5-chloro-1,3-dihydro-3-[[4-[3-(1H-tetrazol-5-yl)-4-pyridinyl]phenyl]methyl]-2H-imidazol-2-one;

1-ethyl-4-pentyl-5-chloro-1,3-dihydro-3-[[4-[3-(1H-tetrazol-5-yl)-4-pyridinyl]phenyl]methyl]-2H-imidazol-2-one;

1-propyl-4-pentyl-5-chloro-1,3-dihydro-3-[[4-[3-(1H-tetrazol-5-yl)-4-pyridinyl]phenyl]methyl]-2H-imidazol-2-one;

1-isopropyl-4-pentyl-5-chloro-1,3-dihydro-3-[[4-[3-(1H-tetrazol-5-yl)-4-pyridinyl]phenyl]methyl]-2H-imidazol-2-one;

1-butyl-4-pentyl-5-chloro-1,3-dihydro-3-[[4- [3-(1H-tetrazol-5-yl)-4-pyridinyl]phenyl]methyl]-2H-imidazol-2-one;

1-secbutyl-4-pentyl-5-chloro-1,3-dihydro-3-[[4-[3-(1H-tetrazol-5-yl)-4-pyridinyl]phenyl]methyl]-2H-imidazol-2-one;

1-isobutyl-4-pentyl-5-chloro-1,3-dihydro-3-[[4-[3-(1H-tetrazol-5-yl)-4-pyridinyl]phenyl]methyl]-2H-imidazol-2-one;

1-tertbutyl-4-pentyl-5-chloro-1,3-dihydro-3-[[4-[3-(1H-tetrazol-5-yl)-4-pyridinyl]phenyl]methyl]-2H-imidazol-2-one;

1,4-dipentyl-5-chloro-1,3-dihydro-3-[[4-[3-(1H-tetrazol-5-yl)-4-pyridinyl]phenyl]methyl]-2H-imidazol-2-one;

1-isopentyl-4-pentyl-5-chloro-1,3-dihydro-3-[[4-[3-(1H-tetrazol-5-yl) -4-pyridinyl]phenyl]methyl]-2H-imidazol-2-one;

1-cyclohexyl-4 -pentyl-5-chloro-1,3-dihydro-3-[[4-[3-(1H-tetrazol-5-yl)-4-pyridinyl]phenyl]methyl]-2H-imidazol-2-one;

1-cyclohexylmethyl-4-pentyl-5-chloro-1,3-dihydro-3-[[4-[3-(1H-tetrazol-5-yl)-4-pyridinyl]phenyl]methyl]-2H-imidazol-2-one;

1-phenyl-4-pentyl-5-chloro-1,3-dihydro-3-[[4-[3-(1H-tetrazol-5-yl)-4-pyridinyl]phenyl]methyl]-2H-imidazol-2-one;

1-phenylmethyl-4-pentyl-5-chloro-1,3-dihydro-3-[[4-[3-(1H-tetrazol-5-yl)-4-pyridinyl]phenyl]methyl]-2H-imidazol-2-one;

1-(2-cyclohexylethyl)-4-pentyl-5-chloro-1,3-dihydro-3-[[4-[3-(1H-tetrazol-5-yl)-4-pyridinyl]phenyl]methyl]-2H-imidazol-2-one;

and 1- (2-phenylethyl) -4-pentyl-5-chloro-1,3-dihydro-3-[[4-[3-(1H-tetrazol-5-yl) -4-pyridinyl]phenyl]methyl]-2H-imidazol-2-one.

A family of compounds of more particular interest within Formula VI consists of compounds and pharmaceutically-acceptable salts thereof as follows:

1-propyl-4-butyl-1,3-dihydro-3-[[4-[3-(1H-tetrazol-5-yl)-4-pyridinyl]phenyl]methyl]-2H-imidazol-2-one;

1,4-dibutyl-1,3-dihydro-3-[[4-[3-(1H-tetrazol-5-yl)-4-pyridinyl]phenyl]methyl]-2H-imidazol-2-one;

1-pentyl-4-butyl-1,3-dihydro-3-[[4-[3-(1H-tetrazol-5-yl)-4-pyridinyl]phenyl]methyl]-2H-imidazol-2-one;

1-isopentyl-4-butyl-1,3-dihydro-3-[[4-[3-(1H-tetrazol-5-yl) -4-pyridinyl]phenyl]methyl]-2H-imidazol-2-one;

1-cyclohexylmethyl-4-butyl-1,3-dihydro-3-[[4-[3-(1H-tetrazol-5-yl)-4-pyridinyl]phenyl]methyl]-2H-imidazol-2-one;

1-phenylmethyl-4-butyl-1,3-dihydro-3-[[4-[3-(1H-tetrazol-5-yl)-4-pyridinyl]phenyl]methyl]-2H-imidazol-2-one;

1-(2-cyclohexylethyl)-4-butyl-1,3-dihydro-3-[[4-[3-(1H-tetrazol-5-yl)-4-pyridinyl]phenyl]methyl]-2H-imidazol-2-one;

1-(2-phenylethyl)-4-butyl-1,3-dihydro-3-[[4-[3-(1H-tetrazol-5-yl)-4-pyridinyl]phenyl]methyl]-2H-imidazol-2-one;

1-propyl-4-butyl-5-methyl-1,3-dihydro-3-[[4-[3-(1H-tetrazol-5-yl)-4-pyridinyl]phenyl]methyl]-2H-imidazol-2-one;

1,4-dibutyl-5-methyl-1,3-dihydro-3-[[4-[3-(1H-tetrazol-5-yl)-4-pyridinyl]phenyl]methyl]-2H-imidazol-2-one;

1-pentyl-4-butyl-5-methyl-1,3-dihydro-3-[[4-[3-(1H-tetrazol-5-yl)-4-pyridinyl]phenyl]methyl]-2H-imidazol-2-one;

1-isopentyl-4-butyl-5-methyl-1,3-dihydro-3-[[4-[3-(1H-tetrazol-5-yl)-4-pyridinyl]phenyl]methyl]-2H-imidazol-2-one;

1-cyclohexylmethyl-4-butyl-5-methyl-1,3-dihydro-3-[[4-[3-(1H-tetrazol-5-yl)-4-pyridinyl]phenyl]methyl]-2H-imidazol-2-one;

1-phenylmethyl-4-butyl-5-methyl-1,3-dihydro-3-[[4-[3-(1H-tetrazol-5-yl)-4-pyridinyl]phenyl]methyl]-2H-imidazol-2-one;

1-(2-cyclohexylethyl)-4-butyl-5-methyl-1,3-dihydro-3-[[4-[3-(1H-tetrazol-5-yl)-4-pyridinyl]phenyl]methyl]-2H-imidazol-2-one;

1-(2-phenylethyl)-4-butyl-5-methyl-1,3-dihydro-3-[[4-[3-(1H-tetrazol-5-yl)-4-pyridinyl]phenyl]methyl]-2H-imidazol-2-one;

1-propyl-4-butyl-5-chloro-1,3-dihydro-3-[[4-[3-(1H-tetrazol-5-yl)-4-pyridinyl]phenyl]methyl]-2H-imidazol-2-one;

1,4-dibutyl-5-chloro-1,3-dihydro-3-[[4-[3-(1H-tetrazol-5-yl)-4-pyridinyl]phenyl]methyl]-2H-imidazol-2-one;

1-pentyl-4-butyl-5-chloro-1,3-dihydro-3-[[4-[3-(1H-tetrazol-5-yl)-4-pyridinyl]phenyl]methyl]-2H-imidazol-2-one;

1-isopentyl-4-butyl-5-chloro-1,3-dihydro-3-[[4-[3-(1H-tetrazol-5-yl)-4-pyridinyl]phenyl]methyl]-2H-imidazol-2-one;

1-cyclohexylmethyl-4-butyl-5-chloro-1,3-dihydro-3-[[4-[3-(1H-tetrazol-5-yl)-4-pyridinyl]phenyl]methyl]-2H-imidazol-2-one;

1-phenylmethyl-4-butyl-5-chloro-1,3-dihydro-3-[[4-[3-(1H-tetrazol-5-yl)-4-pyridinyl]phenyl]methyl]-2H-imidazol-2-one;

1-(2-cyclohexylethyl)-4-butyl-5-chloro-1,3-dihydro-3-[[4-[3-(1H-tetrazol-5-yl)-4-pyridinyl]phenyl]methyl]-2H-imidazol-2-one; and 1-(2-phenylethyl)-4-butyl-5-chloro-1,3-dihydro-3-[[4-[3-(1H-tetrazol-5-yl)-4-pyridinyl]phenyl]methyl]-2H-imidazol-2-one.

Within Formula I there is sixth sub-class of compounds of high interest as represented by Formula VII:

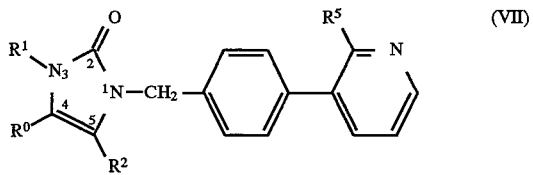

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

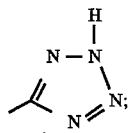

or a tautomer thereof or a pharmaceutically-acceptable salt thereof.

A family of specific compounds of particular interest within Formula VII consists of compounds and pharmaceutically-acceptable salts thereof as follows:

1-methyl-4-propyl-1,3-dihydro-3-[[4-[2-(1H-tetrazol-5-yl)-3-pyridinyl]phenyl]methyl]-2H-imidazol-2-one;

1-ethyl-4-propyl-1,3-dihydro-3-[[4-[2-(1H-tetrazol-5-yl)-3-pyridinyl]phenyl]methyl]-2H-imidazol-2-one;

1,4-dipropyl-1,3-dihydro-3-[[4-[2-(1H-tetrazol-5-yl)-3-pyridinyl]phenyl]methyl]-2H-imidazol-2-one;

1-isopropyl-4-propyl-1,3-dihydro-3-[[4-[2-(1H-tetrazol-5-yl)-3-pyridinyl]phenyl]methyl]-2H-imidazol-2-one;

1-butyl-4-propyl-1,3-dihydro-3-[[4-[2-(1H-tetrazol-5-yl)-3-pyridinyl]phenyl]methyl]-2H-imidazol-2-one;

1-secbutyl-4-propyl-1,3-dihydro-3-[[4-[2-(1H-tetrazol-5-yl) -3-pyridinyl]phenyl]methyl]-2H-imidazol-2-one;

1-isobutyl-4-propyl-1,3-dihydro-3-[[4-[2-(1H-tetrazol-5-yl) -3-pyridinyl]phenyl]methyl]-2H-imidazo-2-one;

1-tertbutyl-4-propyl-1,3-dihydro-3-[[4-[2-(1H-tetrazol-5-yl)-3-pyridinyl]phenyl]methyl]-2H-imidazol-2-one;

1-pentyl-4-propyl-1,3-dihydro-3-[[4-[2-(1H-tetrazol-5-yl)-3-pyridinyl]phenyl]methyl]-2H-imidazol-2-one;

1-isopentyl-4-propyl-1,3-dihydro-3-[[4-[2-(1H-tetrazol-5-yl)-3-pyridinyl]phenyl]methyl]-2H-imidazol-2-one;

1-cyclohexyl-4-propyl-1,3-dihydro-3-[[4-[2-(1H-tetrazol-5-yl)-3-pyridinyl]phenyl]methyl]-2H-imidazol-2-one;

1-cyclohexylmethyl-4-propyl-1,3-dihydro-3-[[4-[2-(1H-tetrazol-5-yl)-3-pyridinyl]phenyl]methyl]-2H-imidazol-2-one;

1-phenyl-4-propyl-1,3-dihydro-3-[[4-[2-(1H-tetrazol-5-yl)-3-pyridinyl]phenyl]methyl]-2H-imidazol-2-one;

1-phenylmethyl-4-propyl-1,3-dihydro-3-[[4-[2-(1H-tetrazol-5-yl)-3-pyridinyl]phenyl]methyl]-2H-imidazol-2-one;

1-(2-cyclohexylethyl)-4-propyl-1,3-dihydro-3-[[4-[2-(1H-tetrazol-5-yl)-3-pyridinyl]phenyl]methyl]-2H-imidazol-2-one;

1-(2-phenylethyl)-4-propyl-1,3-dihydro-3-[[4-[2-(1H-tetrazol-5-yl)-3-pyridinyl]phenyl]methyl]-2H-imidazol-2-one;

1-methyl-4-butyl-1,3-dihydro-3-[[4-[2-(1H-tetrazol-5-yl)-3-pyridinyl]phenyl]methyl]-2H-imidazol-2-one;

1-ethyl-4-butyl-1,3-dihydro-3-[[4-[2-(1H-tetrazol-5-yl)-3-pyridinyl]phenyl]methyl]-2H-imidazol-2-one;

1-propyl-4-butyl-1,3-dihydro-3-[[4-[2-(1H-tetrazol-5-yl)-3-pyridinyl]phenyl]methyl]-2H-imidazol-2-one;

1-isopropyl-4-butyl-1,3-dihydro-3-[[4-[2-(1H-tetrazol-5-yl)-3-pyridinyl]phenyl]methyl]-2H-imidazol-2-one;

1,4-dibutyl-1,3-dihydro-3-[[4-[2-(1H-tetrazol-5-yl)-3-pyridinyl]phenyl]methyl]-2H-imidazol-2-one;

1-secbutyl-4-butyl-1,3-dihydro-3-[[4-[2-(1H-tetrazol-5-yl)-3-pyridinyl]phenyl]methyl]-2H-imidazol-2-one;

1-isobutyl-4-butyl-1,3-dihydro-3-[[4-[2-(1H-tetrazol-5-yl)-3-pyridinyl]phenyl]methyl]-2H-imidazol-2-one;

1-tertbutyl-4-butyl-1,3-dihydro-3-[[4-[2-(1H-tetrazol-5-yl)-3-pyridinyl]phenyl]methyl]-2H-imidazol-2-one;

1-pentyl-4-butyl-1,3-dihydro-3-[[4-[2-(1H-tetrazol-5-yl)-3-pyridinyl]phenyl]methyl]-2H-imidazol-2-one;

1-isopentyl-4-butyl-1,3-dihydro-3-[[4-[2-(1H-tetrazol-5-yl)-3-pyridinyl]phenyl]methyl]-2H-imidazol-2-one;

1-cyclohexyl-4-butyl-1,3-dihydro-3-[[4-[2-(1H-tetrazol-5-yl)-3-pyridinyl]phenyl]methyl]-2H-imidazol-2-one;

1-cyclohexylmethyl-4-butyl-1,3-dihydro-3-[[4-[2-(1H-tetrazol-5-yl)-3-pyridinyl]phenyl]methyl]-2H-imidazol-2-one;

1-phenyl-4-butyl-1,3-dihydro-3-[[4-[2-(1H-tetrazol-5-yl)-3-pyridinyl]phenyl]methyl]-2H-imidazol-2-one;

1-phenylmethyl-4-butyl-1,3-dihydro-3-[[4-[2-(1H-tetrazol-5-yl)-3-pyridinyl]phenyl]methyl]-2H-imidazol-2-one;

1-(2-cyclohexylethyl)-4-butyl-1,3-dihydro-3-[[4-[2-(1H-tetrazol-5-yl)-3-pyridinyl]phenyl]methyl]-2H-imidazol-2-one;

1-(2-phenylethyl)-4-butyl-1,3-dihydro-3-[[4-[2-(1H-tetrazol-5-yl)-3-pyridinyl]phenyl]methyl]-2H-imidazol-2-one;

1-methyl-4-pentyl-1,3-dihydro-3-[[4-[2-(1H-tetrazol-5-yl)-3-pyridinyl]phenyl]methyl]-2H-imidazol-2-one;

1-ethyl-4-pentyl-1,3-dihydro-3-[[4-[2-(1H-tetrazol-5-yl)-3-pyridinyl]phenyl]methyl]-2H-imidazol-2-one;

1-propyl-4-pentyl-1,3-dihydro-3-[[4-[2-(1H-tetrazol-5-yl)-3-pyridinyl]phenyl]methyl]-2H-imidazol-2-one;

1-isopropyl-4-pentyl-1,3-dihydro-3-[[4-[2-(1H-tetrazol-5-yl)-3-pyridinyl]phenyl]methyl]-2H-imidazol-2-one;

1-butyl-4-pentyl-1,3-dihydro-3-[[4-[2-(1H-tetrazol-5-yl)-3-pyridinyl]phenyl]methyl]-2H-imidazol-2-one;

1-secbutyl-4-pentyl-1,3-dihydro-3-[[4-[2-(1H-tetrazol-5-yl)-3-pyridinyl]phenyl]methyl]-2H-imidazol-2-one;

1-isobutyl-4-pentyl-1,3-dihydro-3-[[4-[2-(1H-tetrazol-5-yl)-3-pyridinyl]phenyl]methyl]-2H-imidazol-2-one;

1-tertbutyl-4-pentyl-1,3-dihydro-3-[[4-[2-(1H-tetrazol-5-yl)-3-pyridinyl]phenyl]methyl]-2H-imidazol-2-one;

1,4-dipentyl-1,3-dihydro-3-[[4-[2-(1H-tetrazol-5-yl)-3-pyridinyl]phenyl]methyl]-2H-imidazol-2-one;

1-isopentyl-4-pentyl-1,3-dihydro-3-[[4-[2-(1H-tetrazol-5-yl)-3-pyridinyl]phenyl]methyl]-2H-imidazol-2-one;

1-cyclohexyl-4-pentyl-1,3-dihydro-3-[[4-[2-(1H-tetrazol-5-yl)-3-pyridinyl]phenyl]methyl]-2H-imidazol-2-one;

1-cyclohexylmethyl-4-pentyl-1,3-dihydro-3-[[4-[2-(1H-tetrazol-5-yl)-3-pyridinyl]phenyl]methyl]-2H-imidazol-2-one;

1-phenyl-4-pentyl-1,3-dihydro-3-[[4-[2-(1H-tetrazol-5-yl)-3-pyridinyl]phenyl]methyl]-2H-imidazol-2-one;

1-phenylmethyl-4-pentyl-1,3-dihydro-3-[[4-[2-(1H-tetrazol-5-yl)-3-pyridinyl]phenyl]methyl]-2H-imidazol-2-one;

1-(2-cyclohexylethyl)-4-pentyl-1,3-dihydro-3-[[4-[2-(1H-tetrazol-5-yl)-3-pyridinyl]phenyl]methyl]-2H-imidazol-2-one;

1-(2-phenylethyl)-4-pentyl-1,3-dihydro-3-[[4-[2-(1H-tetrazol-5-yl)-3-pyridinyl]phenyl]methyl]-2H-imidazol-2-one;

1,5-dimethyl-4-propyl-1,3-dihydro-3-[[4-[2-(1H-tetrazol-5-yl)-3-pyridinyl]phenyl]methyl]-2H-imidazol-2-one;

1-ethyl-4-propyl-5-methyl-1,3-dihydro-3-[[4-[2-(1H-tetrazol-5-yl)-3-pyridinyl]phenyl]methyl]-2H-imidazol-2-one;

1,4-dipropyl-5-methyl-1,3-dihydro-3-[[4-[2-(1H-tetrazol-5-yl)-3-pyridinyl]phenyl]methyl]-2H-imidazol-2-one;

1-isopropyl-4-propyl-5-methyl-1,3-dihydro-3-[[4-[2-(1H-tetrazol-5-yl)-3-pyridinyl]phenyl]methyl]-2H-imidazol-2-one;

1-butyl-4-propyl-5-methyl-1,3-dihydro-3-[[4-[2-(1H-tetrazol-5-yl)-3-pyridinyl]phenyl]methyl]-2H-imidazol-2-one;

1-secbutyl-4-propyl-5-methyl-1,3-dihydro-3-[[4-[2-(1H-tetrazol-5-yl)-3-pyridinyl]phenyl]methyl]-2H-imidazol-2-one;

1-isobutyl-4-propyl-5-methyl-1,3-dihydro-3-[[4-[2-(1H-tetrazol-5-yl)-3-pyridinyl]phenyl]methyl]-2H-imidazol-2-one;

1-tertbutyl-4-propyl-5-methyl-1,3-dihydro-3-[[4-[2-(1H-tetrazol-5-yl)-3-pyridinyl]phenyl]methyl]-2H-imidazol-2-one;

1-pentyl-4-propyl-5-methyl-1,3-dihydro-3-[[4-[2-(1H-tetrazol-5-yl)-3-pyridinyl]phenyl]methyl]-2H-imidazol-2-one;

1-isopentyl-4-propyl-5-methyl-1,3-dihydro-3-[[4-[2-(1H-tetrazol-5-yl)-3-pyridinyl]phenyl]methyl]-2H-imidazol-2-one;

1-cyclohexyl-4-propyl-5-methyl-1,3-dihydro-3-[[4-[2-(1H-tetrazol-5-yl)-3-pyridinyl]phenyl]methyl]-2H-imidazol-2-one;

1-cyclohexylmethyl-4-propyl-5-methyl-1,3-dihydro-3-[[4-[2-(1H-tetrazol-5-yl)-3-pyridinyl]phenyl]methyl]-2H-imidazol-2-one;

1-phenyl-4-propyl-5-methyl-1,3-dihydro-3-[[4-[2-(1H-tetrazol-5-yl)-3-pyridinyl]phenyl]methyl]-2H-imidazol-2-one;

1-phenylmethyl-4-propyl-5-methyl-1,3-dihydro-3-[[4-[2-(1H-tetrazol-5-yl)-3-pyridinyl]phenyl]methyl]-2H-imidazol-2-one;

1-(2-cyclohexylethyl)-4-propyl-5-methyl-1,3-dihydro-3-[[4-[2-(1H-tetrazol-5-yl)-3-pyridinyl]phenyl]methyl]-2H-imidazol-2-one;

1-(2-phenylethyl)-4-propyl-5-methyl-1,3-dihydro-3-[[4-[2-(1H-tetrazol-5-yl)-3-pyridinyl]phenyl]methyl]-2H-imidazol-2-one;

1,5-dimethyl-4-butyl-1,3-dihydro-3-[[4-[2-(1H-tetrazol-5-yl)-3-pyridinyl]phenyl]methyl]-2H-imidazol-2-one;

1-ethyl-4-butyl-5-methyl-1,3-dihydro-3-[[4-[2-(1H-tetrazol-5-yl)-3-pyridinyl]phenyl]methyl]-2H-imidazol-2-one;

1-propyl-4-butyl-5-methyl-1,3-dihydro-3-[[4-[2-(1H-tetrazol-5-yl)-3-pyridinyl]phenyl]methyl]-2H-imidazol-2-one;

1-isopropyl-4-butyl-5-methyl-1,3-dihydro-3-[[4-[2-(1H-tetrazol-5-yl)-3-pyridinyl]phenyl]methyl]-2H-imidazol-2-one;

1,4-dibutyl-5-methyl-1,3-dihydro-3-[[4-[2-(1H-tetrazol-5-yl)-3-pyridinyl]phenyl]methyl]-2H-imidazol-2-one;

1-secbutyl-4-butyl-5-methyl-1,3-dihydro-3-[[4-[2-(1H-tetrazol-5-yl)-3-pyridinyl]phenyl]methyl]-2H-imidazol-2-one;

1-isobutyl-4-butyl-5-methyl-1,3-dihydro-3-[[4-[2-(1H-tetrazol-5-yl)-3-pyridinyl]phenyl]methyl]-2H-imidazol-2-one;

1-tertbutyl-4-butyl-5-methyl-1,3-dihydro-3-[[4-[2-(1H-tetrazol-5-yl)-3-pyridinyl]phenyl]methyl]-2H-imidazol-2-one;

1-pentyl-4-butyl-5-methyl-1,3-dihydro-3-[[4-[2-(1H-tetrazol-5-yl)-3-pyridinyl]phenyl]methyl]-2H-imidazol-2-one;

1-isopentyl-4-butyl-5-methyl-1,3-dihydro-3-[[4-[2-(1H-tetrazol-5-yl)-3-pyridinyl]phenyl]methyl]-2H-imidazol-2-one;

1-cyclohexyl-4-butyl-5-methyl-1,3-dihydro-3-[[4-[2-(1H-tetrazol-5-yl)-3-pyridinyl]phenyl]methyl]-2H-imidazol-2-one;

1-cyclohexylmethyl-4-butyl-5-methyl-1,3-dihydro-3-[[4-[2-(1H-tetrazol-5-yl)-3-pyridinyl]phenyl]methyl]-2H-imidazol-2-one;

1-phenyl-4-butyl-5-methyl-1,3-dihydro-3-[[4-[2-(1H-tetrazol-5-yl)-3-pyridinyl]phenyl]methyl]-2H-imidazol-2-one;

1-phenylmethyl-4-butyl-5-methyl-1,3-dihydro-3-[[4-[2-(1H-tetrazol-5-yl)-3-pyridinyl]phenyl]methyl]-2H-imidazol-2-one;

1-(2-cyclohexylethyl)-4-butyl-5-methyl-1,3-dihydro-3-[[4-[2-(1H-tetrazol-5-yl)-3-pyridinyl]phenyl]methyl]-2H-imidazol-2-one;

1-(2-phenylethyl)-4-butyl-5-methyl-1,3-dihydro-3-[[4-[2-(1H-tetrazol-5-yl)-3-pyridinyl]phenyl]methyl]-2H-imidazol-2-one;

1,5-dimethyl-4-pentyl-1,3-dihydro-3-[[4-[2-(1H-tetrazol-5-yl)-3-pyridinyl]phenyl]methyl]-2H-imidazol-2-one;

1-ethyl-4-pentyl-5-methyl-1,3-dihydro-3-[[4-[2-(1H-tetrazol-5-yl)-3-pyridinyl]phenyl]methyl]-2H-imidazol-2-one;

1-propyl-4-pentyl-5-methyl-1,3-dihydro-3-[[4-[2-(1H-tetrazol-5-yl)-3-pyridinyl]phenyl]methyl]-2H-imidazol-2-one;

1-isopropyl-4-pentyl-5-methyl-1,3-dihydro-3-[[4-[2-(1H-tetrazol-5-yl)-3-pyridinyl]phenyl]methyl]-2H-imidazol-2-one;

1-butyl-4-pentyl-5-methyl-1,3-dihydro-3-[[4-[2-(1H-tetrazol-5-yl)-3-pyridinyl]phenyl]methyl]-2H-imidazol-2-one;

1-secbutyl-4-pentyl-5-methyl-1,3-dihydro-3-[[4-[2-(1H-tetrazol-5-yl)-3-pyridinyl]phenyl]methyl]-2H-imidazol-2-one;

1-isobutyl-4-pentyl-5-methyl-1,3-dihydro-3-[[4-[2-(1H-tetrazol-5-yl)-3-pyridinyl]phenyl]methyl]-2H-imidazol-2-one;

1-tertbutyl-4-pentyl-5-methyl-1,3-dihydro-3-[[4-[2-(1H-tetrazol-5-yl)-3-pyridinyl]phenyl]methyl]-2H-imidazol-2-one;

1,4-dipentyl-5-methyl-1,3-dihydro-3-[[4-[2-(1H-tetrazol-5-yl)-3-pyridinyl]phenyl]methyl]-2H-imidazol-2-one;

1-isopentyl-4-pentyl-5-methyl-1,3-dihydro-3-[[4-[2-(1H-tetrazol-5-yl)-3-pyridinyl]phenyl]methyl]-2H-imidazol-2-one;

1-cyclohexyl-4-pentyl-5-methyl-1,3-dihydro-3-[[4-[2-(1H-tetrazol-5-yl)-3-pyridinyl]phenyl]methyl]-2H-imidazol-2-one;

1-cyclohexylmethyl-4-pentyl-5-methyl-1,3-dihydro-3-[[4-[2-(1H-tetrazol-5-yl)-3-pyridinyl]phenyl]methyl]-2H-imidazol-2-one;

1-phenyl-4-pentyl-5-methyl-1,3-dihydro-3-[[4-[2-(1H-tetrazol-5-yl)-3-pyridinyl]phenyl]methyl]-2H-imidazol-2-one;

1-phenylmethyl-4-pentyl-5-methyl-1,3-dihydro-3-[[4-[2-(1H-tetrazol-5-yl)-3-pyridinyl]phenyl]methyl]-2H-imidazol-2-one;

1-(2-cyclohexylethyl)-4-pentyl-5-methyl-1,3-dihydro-3-[[4-[2-(1H-tetrazol-5-yl)-3-pyridinyl]phenyl]methyl]-2H-imidazol-2-one;

1-(2-phenylethyl)-4-pentyl-5-methyl-1,3-dihydro-3-[[4-[2-(1H-tetrazol-5-yl)-3-pyridinyl]phenyl]methyl]-2H-imidazol-2-one;

1-methyl-4-propyl-5-chloro-1,3-dihydro-3-[[4-[2-(1H-tetrazol-5-yl)-3-pyridinyl]phenyl]methyl]-2H-imidazol-2-one;

1-ethyl-4-propyl-5-chloro-1,3-dihydro-3-[[4-[2-(1H-tetrazol-5-yl)-3-pyridinyl]phenyl]methyl]-2H-imidazol-2-one;

1,4-dipropyl-5-chloro-1,3-dihydro-3-[[4-[2-(1H-tetrazol-5-yl)-3-pyridinyl]phenyl]methyl]-2H-imidazol-2-one;

1-isopropyl-4-propyl-5-chloro-1,3-dihydro-3-[[4-[2-(1H-tetrazol-5-yl)-3-pyridinyl]phenyl]methyl]-2H-imidazol-2-one;

1-butyl-4-propyl-5-chloro-1,3-dihydro-3-[[4-[2-(1H-tetrazol-5-yl)-3-pyridinyl]phenyl]methyl]-2H-imidazol-2-one;

1-secbutyl-4-propyl-5-chloro-1,3-dihydro-3-[[4-[2-(1H-tetrazol-5-yl)-3-pyridinyl]phenyl]methyl]-2H-imidazol-2-one;

1-isobutyl-4-propyl-5-chloro-1,3-dihydro-3-[[4-[2-(1H-tetrazol-5-yl)-3-pyridinyl]phenyl]methyl]-2H-imidazol-2-one;

1-tertbutyl-4-propyl-5-chloro-1,3-dihydro-3-[[4-[2-(1H-tetrazol-5-yl)-3-pyridinyl]phenyl]methyl]-2H-imidazol-2-one;

1-pentyl-4-propyl-5-chloro-1,3-dihydro-3-[[4-[2-(1H-tetrazol-5-yl)-3-pyridinyl]phenyl]methyl]-2H-imidazol-2-one;

1-isopentyl-4-propyl-5-chloro-1,3-dihydro-3-[[4-[2-(1H-tetrazol-5-yl)-3-pyridinyl]phenyl]methyl]-2H-imidazol-2-one;

1-cyclohexyl-4-propyl-5-chloro-1,3-dihydro-3-[[4-[2-(1H-tetrazol-5-yl)-3-pyridinyl]phenyl]methyl]-2H-imidazol-2-one;

1-cyclohexylmethyl-4-propyl-5-chloro-1,3-dihydro-3-[[4-[2-(1H-tetrazol-5-yl)-3-pyridinyl]phenyl]methyl]-2H-imidazol-2-one;

1-phenyl-4-propyl-5-chloro-1,3-dihydro-3-[[4-[2-(1H-tetrazol-5-yl)-3-pyridinyl]phenyl]methyl]-2H-imidazol-2-one;

1-phenylmethyl-4-propyl-5-chloro-1,3-dihydro-3-[[4-[2-(1H-tetrazol-5-yl)-3-pyridinyl]phenyl]methyl]-2H-imidazol-2-one; 1-(2-cyclohexylethyl)-4-propyl-5- chloro-1,3-dihydro-3-[[4-[2-(1H-tetrazol-5-yl)-3-pyridinyl]phenyl]methyl]-2H-imidazol-2-one;

1-(2-phenylethyl)-4-propyl-5-chloro-1,3-dihydro-3-[[4-[2-(1H-tetrazol-5-yl)-3-pyridinyl]phenyl]methyl]-2H-imidazol-2-one;

1-methyl-4-butyl-5-chloro-1,3-dihydro-3-[[4-[2-(1H-tetrazol-5-yl)-3-pyridinyl]phenyl]methyl]-2H-imidazol-2-one;

1-ethyl-4-butyl-5-chloro-1,3-dihydro-3-[[4-[2-(1H-tetrazol-5-yl)-3-pyridinyl]phenyl]methyl]-2H-imidazol-2-one;

1-propyl-4-butyl-5-chloro-1,3-dihydro-3-[[4-[2(1H-tetrazol-5-yl)-3-pyridinyl]phenyl]methyl]-2H-imidazol-2-one;

1-isopropyl-4-butyl-5-chloro-1,3-dihydro-3-[[4-[2-(1H-tetrazol-5-yl)-3-pyridinyl]phenyl]methyl]-2H-imidazol-2-one;

1,4-dibutyl-5-chloro-1,3-dihydro-3-[[4-[2-(1H-tetrazol-5-yl)-3-pyridinyl]phenyl]methyl]-2H-imidazol-2-one;

1-secbutyl-4-butyl-5-chloro-1,3-dihydro-3-[[4-[2-(1H-tetrazol-5-yl)-3-pyridinyl]phenyl]methyl]-2H-imidazol-2-one;

1-isobutyl-4-butyl-5-chloro-1,3-dihydro-3-[[4-[2-(1H-tetrazol-5-yl)-3-pyridinyl]phenyl]methyl]-2H-imidazol-2-one;

1-tertbutyl-4-butyl-5-chloro-1,3-dihydro-3-[[4-[2-(1H-tetrazol-5-yl)-3-pyridinyl]phenyl]methyl]-2H-imidazol-2-one;

1-pentyl-4-butyl-5-chloro-1,3-dihydro-3-[[4-[2-(1H-tetrazol-5-yl)-3-pyridinyl]phenyl]methyl]-2H-imidazol-2-one;

1-isopentyl-4-butyl-5-chloro-1,3-dihydro-3-[[4-[2-(1H-tetrazol-5-yl)-3-pyridinyl]phenyl]methyl]-2H-imidazol-2-one;

1-cyclohexyl-4-butyl-5-chloro-1,3-dihydro-3-[[4-[2-(1H-tetrazol-5-yl)-3-pyridinyl]phenyl]methyl]-2H-imidazol-2-one;

1-cyclohexylmethyl-4-butyl-5-chloro-1,3-dihydro-3-[[4-[2-(1H-tetrazol-5-yl)-3-pyridinyl]phenyl]methyl]-2H-imidazol-2-one;

1-phenyl-4-butyl-5-chloro-1,3-dihydro-3-[[4-[2-(1H-tetrazol-5-yl)-3-pyridinyl]phenyl]methyl]-2H-imidazol-2-one;

1-phenylmethyl-4-butyl-5-chloro-1,3-dihydro-3-[[4-[2-(1H-tetrazol-5-yl)-3-pyridinyl]phenyl]methyl]-2H-imidazol-2-one;

1-(2-cyclohexylethyl)-4-butyl-5-chloro-1,3-dihydro-3-[[4-[2-(1H-tetrazol-5-yl)-3-pyridinyl]phenyl]methyl]-2H-imidazol-2-one;

1-(2-phenylethyl)-4-butyl-5-chloro-1,3-dihydro-3-[[4-[2-(1H-tetrazol-5-yl)-3-pyridinyl]phenyl]methyl]-2H-imidazol-2-one;

1-methyl-4-pentyl-5-chloro-1,3-dihydro-3-[[4-[2-(1H-tetrazol-5-yl)-3-pyridinyl]phenyl]methyl]-2H-imidazol-2-one;

1-ethyl-4-pentyl-5-chloro-1,3-dihydro-3-[[4-[2-(1H-tetrazol-5-yl)-3-pyridinyl]phenyl]methyl]-2H-imidazol-2-one;

1-propyl-4-pentyl-5-chloro-1,3-dihydro-3-[[4-[2-(1H-tetrazol-5-yl)-3-pyridinyl]phenyl]methyl]-2H-imidazol-2-one;

1-isopropyl-4-pentyl-5-chloro-1,3-dihydro-3-[[4-[2-(1H-tetrazol-5-yl)-3-pyridinyl]phenyl]methyl]-2H-imidazol-2-one;

1-butyl-4-pentyl-5-chloro-1,3-dihydro-3-[[4-[2-(1H-tetrazol-5-yl)-3-pyridinyl]phenyl]methyl]-2H-imidazol-2-one;

1-secbutyl-4-pentyl-5-chloro-1,3-dihydro-3-[[4-[2-(1H-tetrazol-5-yl)-3-pyridinyl]phenyl]methyl]-2H-imidazol-2-one;

1-isobutyl-4-pentyl-5-chloro-1,3-dihydro-3-[[4-[2-(1H-tetrazol-5-yl)-3-pyridinyl]phenyl]methyl]-2H-imidazol-2-one;

1-tertbutyl-4-pentyl-5-chloro-1,3-dihydro-3-[[4-[2-(1H-tetrazol-5-yl)-3-pyridinyl]phenyl]methyl]-2H-imidazol-2-one;

1,4-dipentyl-5-chloro-1,3-dihydro-3-[[4-[2-(1H-tetrazol-5-yl)-3-pyridinyl]phenyl]methyl]-2H-imidazol-2-one;

1-isopentyl-4-pentyl-5-chloro-1,3-dihydro-3-[[4-[2-(1H-tetrazol-5-yl)-3-pyridinyl]phenyl]methyl]-2H-imidazol-2-one;

1-cyclohexyl-4-pentyl-5-chloro-1,3-dihydro-3-[[4-[2-(1H-tetrazol-5-yl)-3-pyridinyl]phenyl]methyl]-2H-imidazol-2-one;

1-cyclohexylmethyl-4-pentyl-5-chloro-1,3-dihydro-3-[[4-[2-(1H-tetrazol-5-yl)-3-pyridinyl]phenyl]methyl]-2H-imidazol-2-one;

1-phenyl-4-pentyl-5-chloro-1,3-dihydro-3-[[4-[2-(1H-tetrazol-5-yl)-3-pyridinyl]phenyl]methyl]-2H-imidazol-2-one;

1-phenylmethyl-4-pentyl-5-chloro-1,3-dihydro-3-[[4-[2-(1H-tetrazol-5-yl)-3-pyridinyl]phenyl]methyl]-2H-imidazol-2-one;

1-(2-cyclohexylethyl)-4-pentyl-5-chloro-1,3-dihydro-3-[[4-[2-(1H-tetrazol-5-yl)-3-pyridinyl]phenyl]methyl]-2H-imidazol-2-one; and 1-(2-phenylethyl)-4-pentyl-5-chloro-1,3-dihydro-3-[[4-[2-(1H-tetrazol-5-yl)-3-pyridinyl]phenyl]methyl]-2H-imidazol-2-one.

A family of compounds of more particular interest within Formula VII consists of compounds and pharmaceutically-acceptable salts as follows:

1-propyl-4-butyl-1,3-dihydro-3-[[4-[2-(1H-tetrazol-5-yl)-3-pyridinyl]phenyl]methyl]-2H-imidazol-2-one;

1,4-dibutyl-1,3-dihydro-3-[[4-[2-(1H-tetrazol-5-yl)-3-pyridinyl]phenyl]methyl]-2H-imidazol-2-one;

1-pentyl-4-butyl-1,3-dihydro-3-[[4-[2-(1H-tetrazol-5-yl)-3-pyridinyl]phenyl]methyl]-2H-imidazol-2-one;

1-isopentyl-4-butyl-1,3-dihydro-3-[[4-[2-(1H-tetrazol-5-yl)-3-pyridinyl]phenyl]methyl]-2H-imidazol-2-one;

1-cyclohexylmethyl-4-butyl-1,3-dihydro-3-[[4-[2-(1H-tetrazol-5-yl)-3-pyridinyl]phenyl]methyl]-2H-imidazol-2-one;

1-phenylmethyl-4-butyl-1,3-dihydro-3-[[4-[2-(1H-tetrazol-5-yl)-3-pyridinyl]phenyl]methyl]-2H-imidazol-2-one;

1-(2-cyclohexylethyl)-4-butyl-1,3-dihydro-3-[[4-[2-(1H-tetrazol-5-yl)-3-pyridinyl]phenyl]methyl]-2H-imidazol-2-one;

1-(2-phenylethyl)-4-butyl-1,3-dihydro-3-[[4-[2-(1H-tetrazol-5-yl)-3-pyridinyl]phenyl]methyl]-2H-imidazol-2-one;

1-propyl-4-butyl-5-methyl-1,3-dihydro-3-[[4-[2-(1H-tetrazol-5-yl)-3-pyridinyl]phenyl]methyl]-2H-imidazol-2-one;

1,4-dibutyl-5-methyl-1,3-dihydro-3-[[4-[2-(1H-tetrazol-5-yl)-3-pyridinyl]phenyl]methyl]-2H-imidazol-2-one;

1-pentyl-4-butyl-5-methyl-1,3-dihydro-3-[[4-[2-(1H-tetrazol-5-yl)-3-pyridinyl]phenyl]methyl]-2H-imidazol-2-one;

1-isopentyl-4-butyl-5-methyl-1,3-dihydro-3-[[4-[2-(1H-tetrazol-5-yl)-3-pyridinyl]phenyl]methyl]-2H-imidazol-2-one;

1-cyclohexylmethyl-4-butyl-5-methyl-1,3-dihydro-3-[[4-[2-(1H-tetrazol-5-yl)-3-pyridinyl]phenyl]methyl]-2H-imidazol-2-one;

1-phenylmethyl-4-butyl-5-methyl-1,3-dihydro-3-[[4-[2-(1H-tetrazol-5-yl)-3-pyridinyl]phenyl]methyl]-2H-imidazol-2-one;

1-(2-cyclohexylethyl)-4-butyl-5-methyl-1,3-dihydro-3-[[4-[2-(1H-tetrazol-5-yl)-3-pyridinyl]phenyl]methyl]-2H-imidazol-2-one;

1-(2-phenylethyl)-4-butyl-5-methyl-1,3-dihydro-3-[[4-[2-(1H-tetrazol-5-yl)-3-pyridinyl]phenyl]methyl]-2H-imidazol-2-one;

1-propyl-4-butyl-5-chloro-1,3-dihydro-3-[[4-[2-(1H-tetrazol-5-yl)-3-pyridinyl]phenyl]methyl]-2H-imidazol-2-one;

1,4-dibutyl-5-chloro-1,3-dihydro-3-[[4-[2-(1H-tetrazol-5-yl)-3-pyridinyl]phenyl]methyl]-2H-imidazol-2-one;

1-pentyl-4-butyl-5-chloro-1,3-dihydro-3-[[4-[2-(1H-tetrazol-5-yl)-3-pyridinyl]phenyl]methyl]-2H-imidazol-2-one;

1-isopentyl-4-butyl-5-chloro-1,3-dihydro-3-[[4-[2-(1H-tetrazol-5-yl)-3-pyridinyl]phenyl]methyl]-2H-imidazol-2-one;

1-cyclohexylmethyl-4-butyl-5-chloro-1,3-dihydro-3-[[4-[2-(1H-tetrazol-5-yl)-3-pyridinyl]phenyl]methyl]-2H-imidazol-2-one;

1-phenylmethyl-4-butyl-5-chloro-1,3-dihydro-3-[[4-[2-(1H-tetrazol-5-yl)-3-pyridinyl]phenyl]methyl]-2H-imidazol-2-one;

1-(2-cyclohexylethyl)-4-butyl-5-chloro-1,3-dihydro-3-[[4-2-(1H-tetrazol-5-yl)-3-pyridinyl]phenyl]methyl]-2H-imidazol-2-one; and 1-(2-phenylethyl)-4-butyl-5-chloro-1,3-dihydro-3-[[4-[2-(1H-tetrazol-5-yl)-3-pyridinyl]phenyl]methyl]-2H-imidazol-2-one.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perflhoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl; phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin II is a potent vasoconstrictor and participates in the formation of aldosterone which regulates sodium and water balance in meals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from or afflicted by the effects of hypertension or susceptible to a hypertensive condition if not treated to prevent or control such hypertension.

Also included in the family of compounds of Formula I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, sailcyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–XX, wherein the R substituents are as defined for Formula I, above, except where further noted.

Scheme I

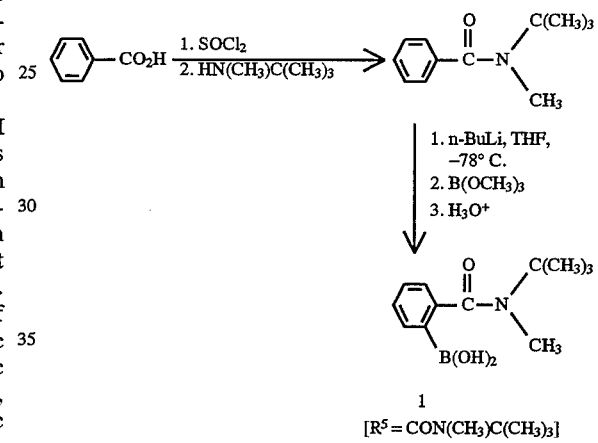

Synthetic Scheme I shows the preparation of the boronic acid 1 where $R^5$ equals N-tertbutyl-N-methylcarboxamide. In step 1, benzoic acid is treated with thionyl chloride to give the corresponding acid chloride which is subsequently reacted with N-tertbutyl-N-methylamine to give N-tertbutyl-N-methylbenzamide. In step 2, the amide is ortho-metalated and subsequently reacted with trimethyl borate. The free boronic acid 1 is produced on hydroylsis.

Scheme II

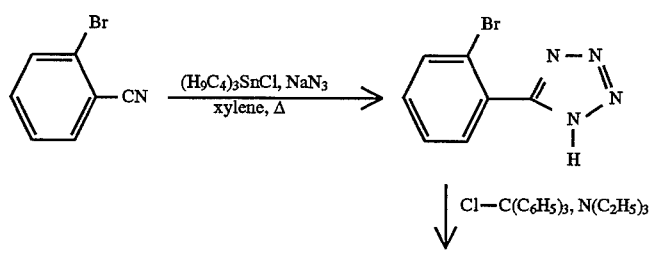

-continued
Scheme II

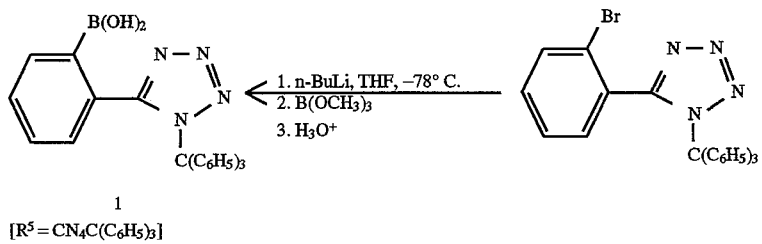

1

[$R^5 = CN_4C(C_6H_5)_3$]

Synthetic Scheme II shows the preparation of the boronic acid 1 where $R^5$ equals N-triphenylmethyl-1H-tetrazole. In step 1, 2-bromobenzonitrile (Aldrich) is reacted with tributyltin azide to give the corresponding tetrazole. In step 2, the tetrazole is reacted with triphenylmethyl chloride in the presence of triethylamine to give the protected bromophenyltetrazole. In step 3, halogen-metal interchange with n-butyllithium generates the corresponding ortho-lithiated species which is reacted with trimethyl borate. The free boronic acid 1 is produced on hydrolysis.

Scheme III

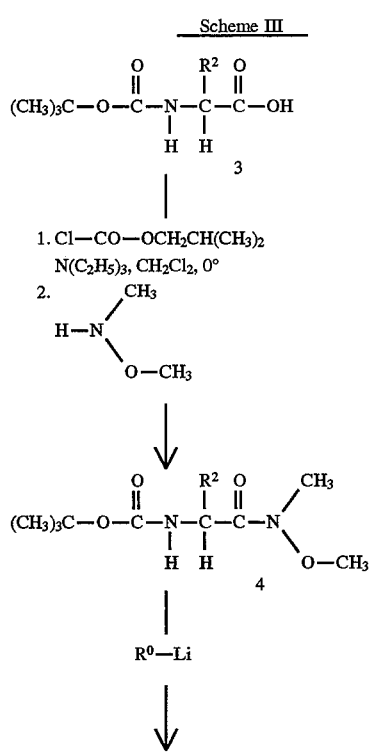

-continued
Scheme III

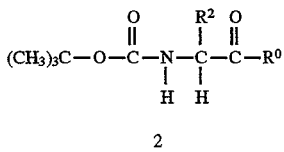

2

Synthetic Scheme III shows the preparation of N-Boc-amino ketones 2 (or aldehydes when $R^0$=H) from the corresponding N-Boc-amino acides 3. In step 1, the amino acid 3 is reacted with isobutyl chloroformate in the presence of triethylamine and subsequently with N,O-dimethylhydroxylamine to give the corresponding N-methoxy-N-methylamide 4. In step 2, the amide 4 is reacted with an organolithium reagent $R^0$-Li (or lithium aluminum hydride (LAH) when $R^0$=H) to give the desired ketone 2 (or aldehyde when $R^0$=H).

Scheme IV

METHOD A:

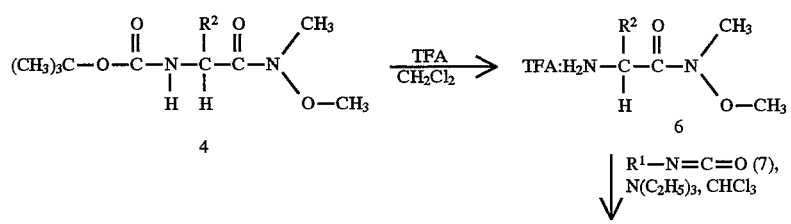

-continued
Scheme IV

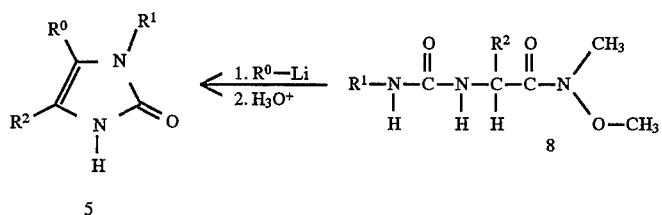

Synthetic Scheme IV shows the preparation of imidazol-2-ones 5 from the corresponding amides 4 via Method A. In step 1, the protected amide 4 (prepared in Scheme III) is reacted with trifluoroacetic acid (TFA) to give the TFA salt 6 of the free amine. In step 2, the salt 6 is reacted with the appropriate isocyanate 2 in the presence of triethylamine to give the urea 8. In step 3, the urea 8 is reacted with an organolithium reagent $R^0$-Li (or lithium aluminum hydride (LAH) when $R^0$=H) and subsequently cyclized to the imidazole-2-one 5 on treatment with dilute acid during the work-up procedure.

Scheme V

METHOD B:

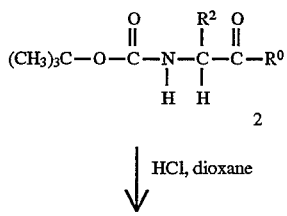

-continued
Scheme V

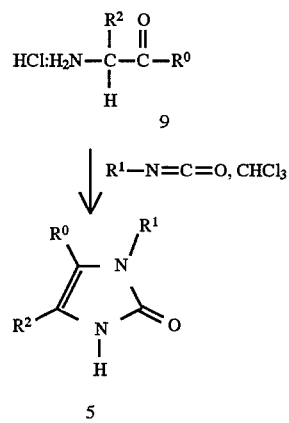

Synthetic Scheme V shows the preparation of imidazol-2-ones 5 from the corresponding N-Boc-protected amino ketones 2 (or aldehydes when $R^0$=H) via Method B. In step 1, the carbonyl compound 2 (prepared in Scheme III) is reacted with anhydrous hydrogen chloride in dioxane to give the HCl salt 9. In step 2, the salt 9 is reacted with the appropriate isocyanate 2 in chloroform to give the imidazol-2-one 5 directly.

Scheme VI

METHOD C:

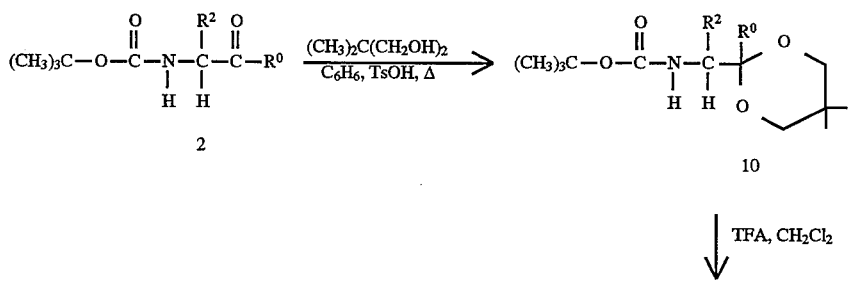

-continued
Scheme VI

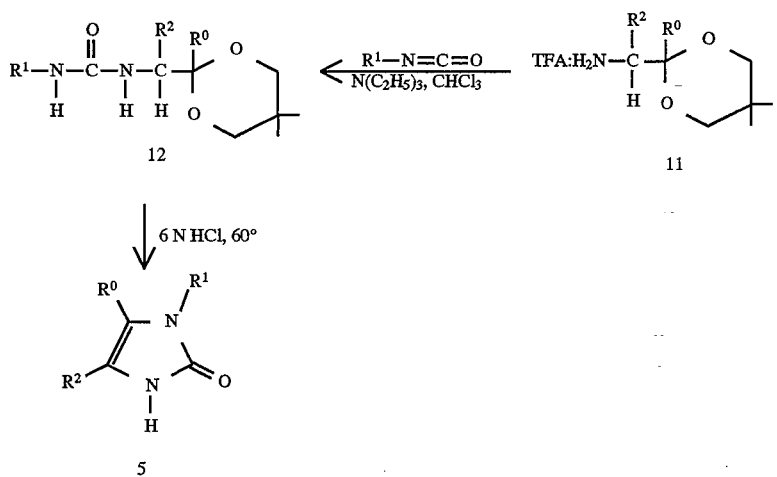

Synthetic Scheme VI shows the preparation of imidazol-2-ones 5 from the corresponding N-Boc-protected amino ketones 2 (or aldehydes when $R^0$=H) via Method C. In step 1, the carbonyl compound 2 (prepared in Scheme III) is reacted with 2,2-dimethyl-1,3-propandiol to give the cyclic ketal 10. In step 2, the ketal 10 is reacted with TFA to give the TFA salt 11 of the free amine. In step 3, the salt 11 is reacted with the appropriate isocyanate 7 in the presence of triethylamine to give the urea ketal 12. In step 4, the urea ketal 12 is reacted with 6N hydrochloric acid at 60° C. to give the desired imidazol-2-one 5 directly.

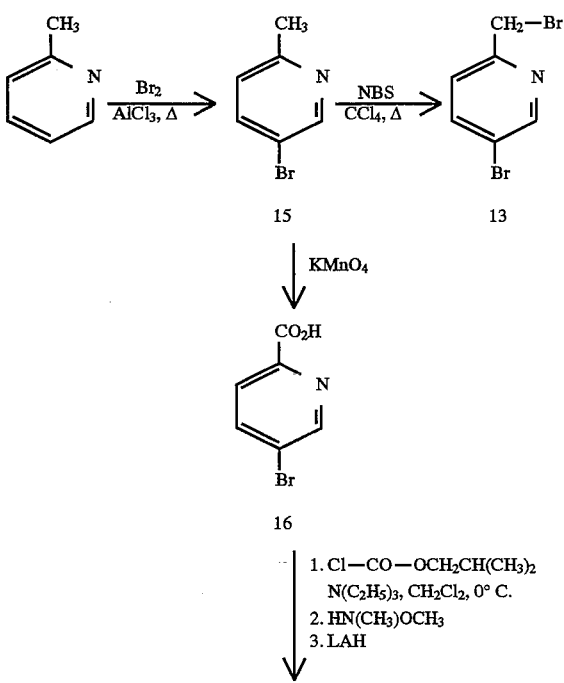

-continued
Scheme VII

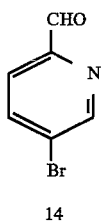

14

Synthetic Scheme VII shows the preparation of 2-bromomethyl-5-bromopyridine (13) and 5-bromo-2-pyridinecarboxaldehyde (14) from 2-picoline (Aldrich). In step 1, 2-picoline is reacted with bromine in the presence of a large excess of aluminum chloride at elevated temperatures to give 5-bromo-2-picoline (15). In step 2a, 15 is reacted with NBS to give the 2-pyridinylmethyl bromide 13. In step 2b, the intermediate 15 is treated with potassium permanganate to give the corresponding picolinic acid 16. In step 3b, the acid 16 is first converted to its N-methoxy-N-methylamide and subsequently reduced with LAH to provide 5-bromo-2-pyridinecarboxaldehyde (14).

Scheme VIII

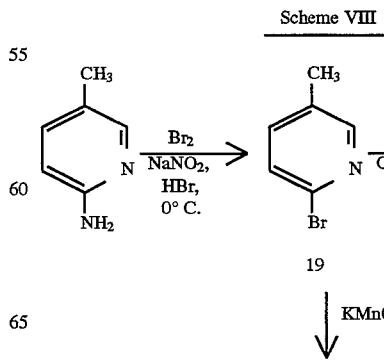

-continued
Scheme VIII

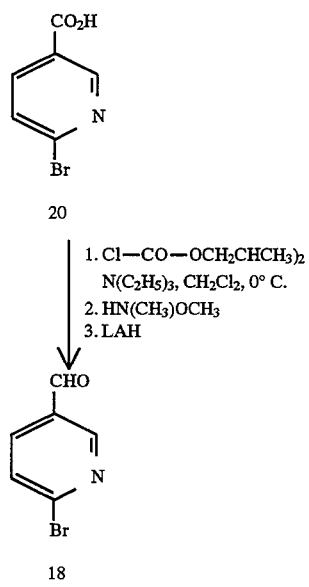

Synthetic Scheme VIII shows the preparation of 2-bromo-5-bromomethylpyridine (17) and 2-bromo-5-pyridinecarboxaldehyde (18) from 2-amino-5-picoline (Aldrich). In step 1, 2-amino-5-picoline is reacted with bromine in the presence of hydrobromic acid and sodium nitrite at 0° C. to give 2-bromo-5-picoline (19). In step 2a, 19 is reacted with NBS to give the 3-pyridinylmethyl bromide 17. In step 2b, the intermediate 19 is treated with potassium permanganate to give the corresponding nicotinic acid 20. In step 3b, the acid 20 is first converted to its N-methoxy-N-methylamide and subsequently reduced with LAH to provide 2-bromo-5-pyridinecarboxaldehyde (18).

Scheme IX

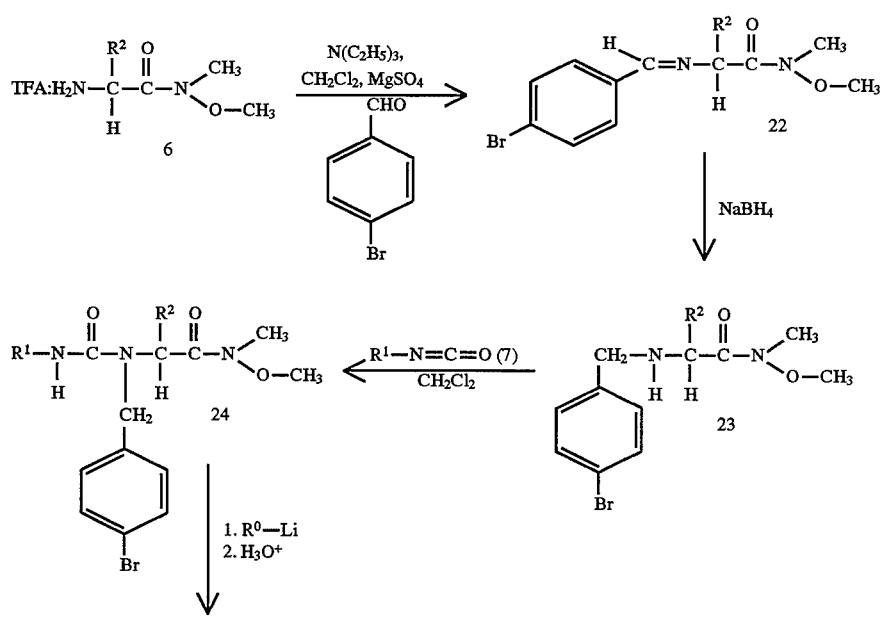

-continued
Scheme IX

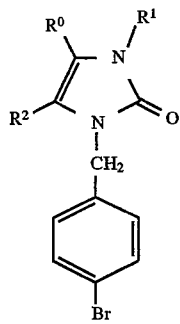

21

Synthetic Scheme IX shows the preparation of (4-bromobenzyl)imidazol-2-ones 21 from the TFA salt of the amino amide 6 (prepared in Scheme III). In step 1, the TFA salt 6 is allowed to react with the 4-bromobenzaldehyde in the presence of triethylamine and anhydrous magnesium sulfate to give the imine 22. In step 2, the imine 22 is allowed to react with sodium borohydride to give the substituted benzylamine 23. In step 3, the benzylamine 23 is allowed to react with the appropriate isocyanate 7 to give the substituted benzylurea 24. In step 4, the urea 23 is first allowed to react with an organolithium reagent $R^0Li$ (or lithium aluminum hydride (LAH) when $R^0=H$) and subsequently with dilute aqueous acid to give the desired 3-(4-bromobenzyl)imidazol-2-ones.

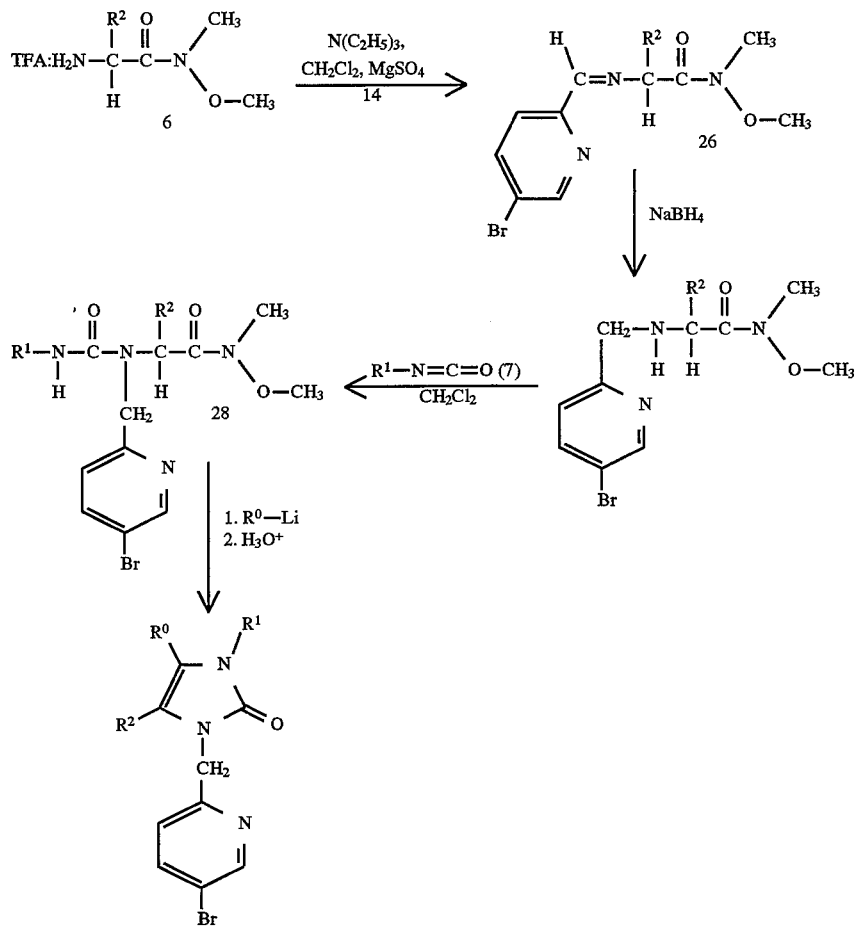

Synthetic Scheme X shows the preparation of 3-(5-bromo-2-pyridinyimethyl)imidazol-2-ones 25 from the TFA salt of the amino amide 6 (prepared in Scheme III). In step 1, the TFA salt 6 is allowed to react with the 5-bromo-2-pyridinylaldehyde 14 (prepared in Scheme VII) in the presence of triethylamine and anhydrous magnesium sulfate to give the imine 26. In step 2, the imine 26 is allowed to react with sodium borohydride to give the substituted benzylamine 27. In step 3, the benzylamine 27 is allowed to react with the appropriate isocyanate 7 to give the substituted benzylurea 28. In step 4, the urea 28 is first allowed to react with an organolithium reagent R⁰-Li (or lithium aluminum hydride (LAH) when R⁰=H) and subsequently with dilute aqueous acid to give the desired 3-(5-bromo-2-pyridinylmethyl)imidazol-2-ones 25.

Synthetic Scheme XI shows the preparation of 3-(2-bromo-5-pyridinylmethyl)imidazol-2-ones 29 from the TFA salt of the amino amide 6 (prepared in Scheme III). In step 1, the TFA salt 6 is allowed to react with 2-bromo-5-pyridinylaldehyde 18 (prepared in Scheme VIII) in the presence of triethylamine and anhydrous magnesium sulfate to give the imine 30. In step 2, the imine 30 is allowed to react with sodium borohydride to give the substituted benzylamine 31. In step 3, the benzylamine 31 is allowed to react with the appropriate isocyanate 7 to give the substituted benzylurea 32. In step 4, the urea 32 is first allowed to react with an organolithium reagent R⁰-Li (or lithium aluminum hydride (LAH) when R⁰=H) and subsequently with dilute aqueous acid to give the desired 3-(2-bromo-5-pyridinylmethyl)imidazol-2-ones 29.

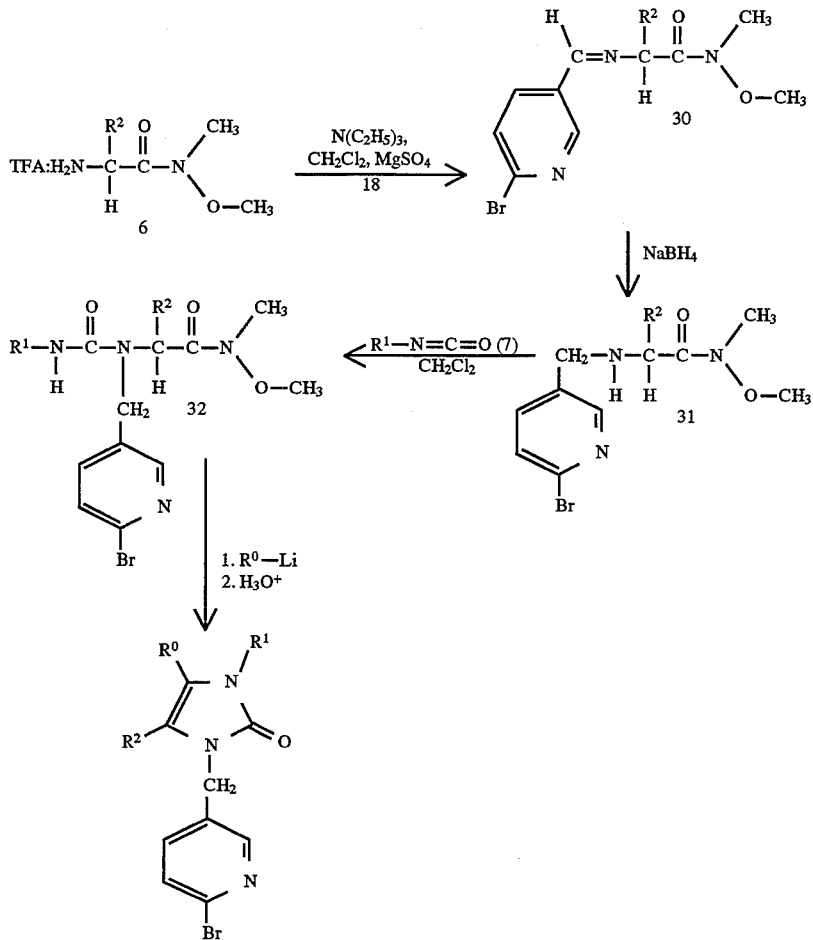

Scheme XI

Scheme XII

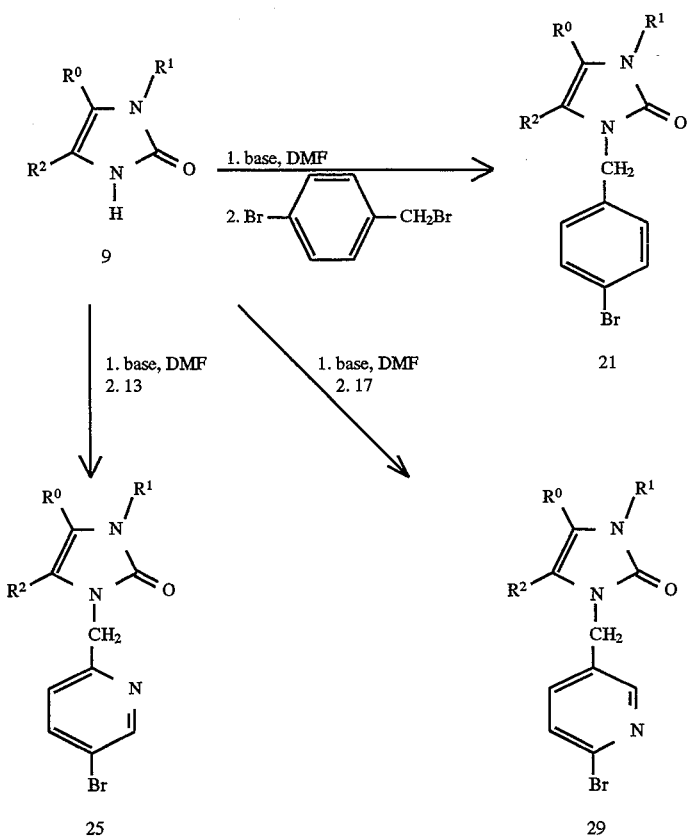

Synthetic Scheme XII shows the preparation of 3-(4-bromobenzyl)imidazol-2-ones 21, 3-(5-bromo-2-pyridinylmethyl)imidazol-2-ones 25, and 3-(2-bromo-5-pyridinylmethyl)imidazol-2-ones 29 from the parent imidazol-2-ones 9 (prepared in Scheme IV, Scheme V, or Scheme VI). The imidazol-2-one 9 is first treated with a base, such as potassium t-butoxide, and subsequently with the alkylating agent 4-bromobenzyl bromide, 13 (prepared in Scheme VII), and 17 (prepared in Scheme VIII) to give 3-(4-bromobenzyl)imidazol-2-ones 21, 3-(5-bromo-2-pyridinylmethyl)imidazol-2-ones 25, and 3-(2-bromo-5-pyridinylmethyl)imidazol-2-ones 29, respectively.

Scheme XIII

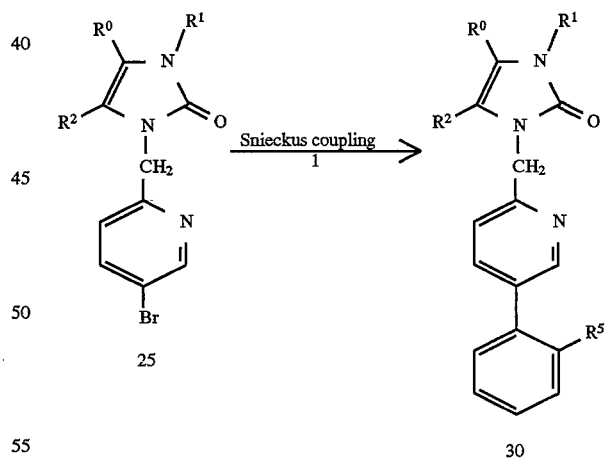

Synthetic Scheme XIII shows the preparation of 3-[[5-[2-(1H-tetrazol-5-yl)phenyl]-2-pyridinyl]methyl]-2H-imidazol-2-ones 30 from the boronic acid 1 (prepared in Scheme I and Scheme II) and the bromoimidazol-2-one coupling reagent 25 (prepared in Scheme X and Scheme XII). The boronic acid 1 is reacted with the bromoimidazol-2-one coupling reagent 25 in the presence of a palladium zero catalyst via a Snieckus coupling [see M. J. Sharp and V. Snieckus, *Tetrahedron Lett.*, 5997(1985)] to give the angiotensin II antagonists 30 of this invention.

Scheme XIV

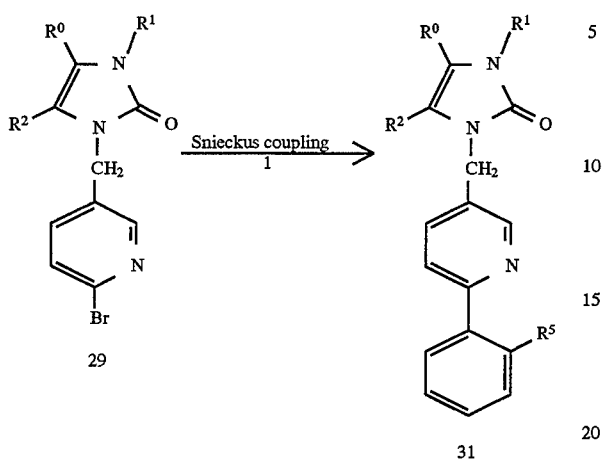

Synthetic Scheme XIV shows the preparation of 3-[[6-[2-(1H-tetrzol-5-yl)phenyl]-3-pyridinyl]methyl]-2H-imidazol-2-ones 31 from the boronic acid 1 (prepared in Scheme I and Scheme II) and the bromoimidazol-2-one coupling reagent 29 (prepared in Scheme XI and Scheme XII). The boronic acid 1 is reacted with the bromoimidazol-2-one coupling reagent 29 in the presence of a palladium zero catalyst via a Snieckus coupling [see M. J. Sharp and V. Snieckus, *Tetrahedron Lett.*, 5997(1985)] to give the angiotensin II antagonists 31 of this invention.

Scheme XV

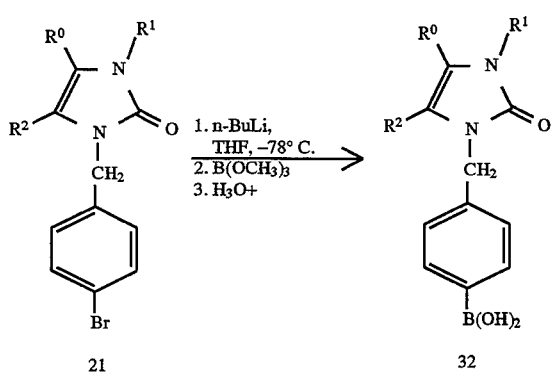

Synthetic Scheme XV shows the preparation of the imidazol-2-one boronic acid coupling reagents 32 from the corresponding 3-(4-bromobenzyl)imidazol-2-ones 21 (prepared in Scheme IX and Scheme XII). Halogen-metal interchange generates the corresponding lithiated species from 21 which is reacted with trimethyl borate. The free imidazol-2-one boronic acid coupling reagents 32 are produced on acid hydrolysis.

Scheme XVI

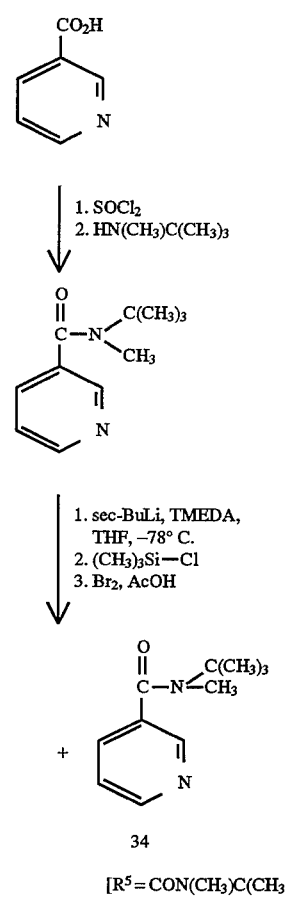

Synthetic Scheme XVI shows the preparation of the 4-bromopyridine coupling reagent 33 [R$^5$=CON(CH$_3$)C(CH$_3$)$_3$] and the 2-bromopyridine coupling reagent 34 [R$^5$= CON(CH$_3$)C(CH$_3$)$_3$] from nicotinic acid. In step 1, N-tertbuty-N-methylnicotinamide is prepared from nicotinoyl chloride and N-tertbutyl-N-methylamine. In step 2, ortho-metalation with sec-butyllithium gives a mixture of regioanions which are reacted with trimethylsilyl chloride; subsequent conversion to the corresponding bromides on treatment with bromine in acetic acid and separation of the regioisomers by chromatography provides 33 and 34.

Scheme XVII

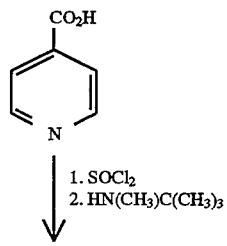

-continued
Scheme XVII

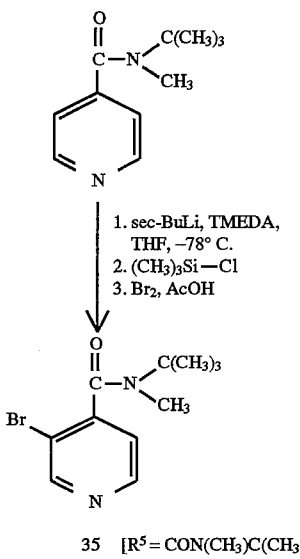

35  [R⁵ = CON(CH₃)C(CH₃)₃]

Synthetic Scheme XVII shows the preparation of the 3-bromopyridine coupling reagent 35 [R⁵=CON(CH₃)C(CH₃)₃] from isonicotinic acid. In step 1, N-tertbutyl-N-methylisonicotinamide is prepared from isonicotinoyl chloride and N-tertbutyl-N-methylamine. In step 2, reaction with sec-butyllithium gives the ortho-lithiated species which is reacted with trimethylsilyl chloride and subsequently converted to the corresponding bromide 35 on treatment with bromine in acetic acid.

Scheme XVIII

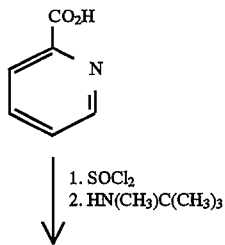

-continued
Scheme XVIII

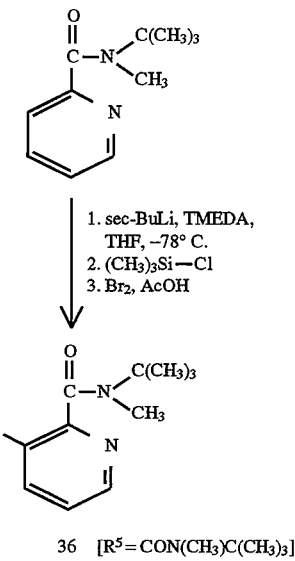

36  [R⁵ = CON(CH₃)C(CH₃)₃]

Synthetic Scheme XVIII shows the preparation of the 3-bromopyridine coupling reagent 36 [R⁵=CON(CH₃)C(CH₃)₃] from picolinic acid. In step 1, N-tertbutyl-N-methylpicolinamide is prepared from picolinoyl chloride and N-tertbutyl-N-methylamine. In step 2, reaction with sec-butyllithium gives the ortho-lithiated species which is reacted with trimethylsilyl chloride and subsequently converted to the corresponding bromide 36 on treatment with bromine in acetic acid.

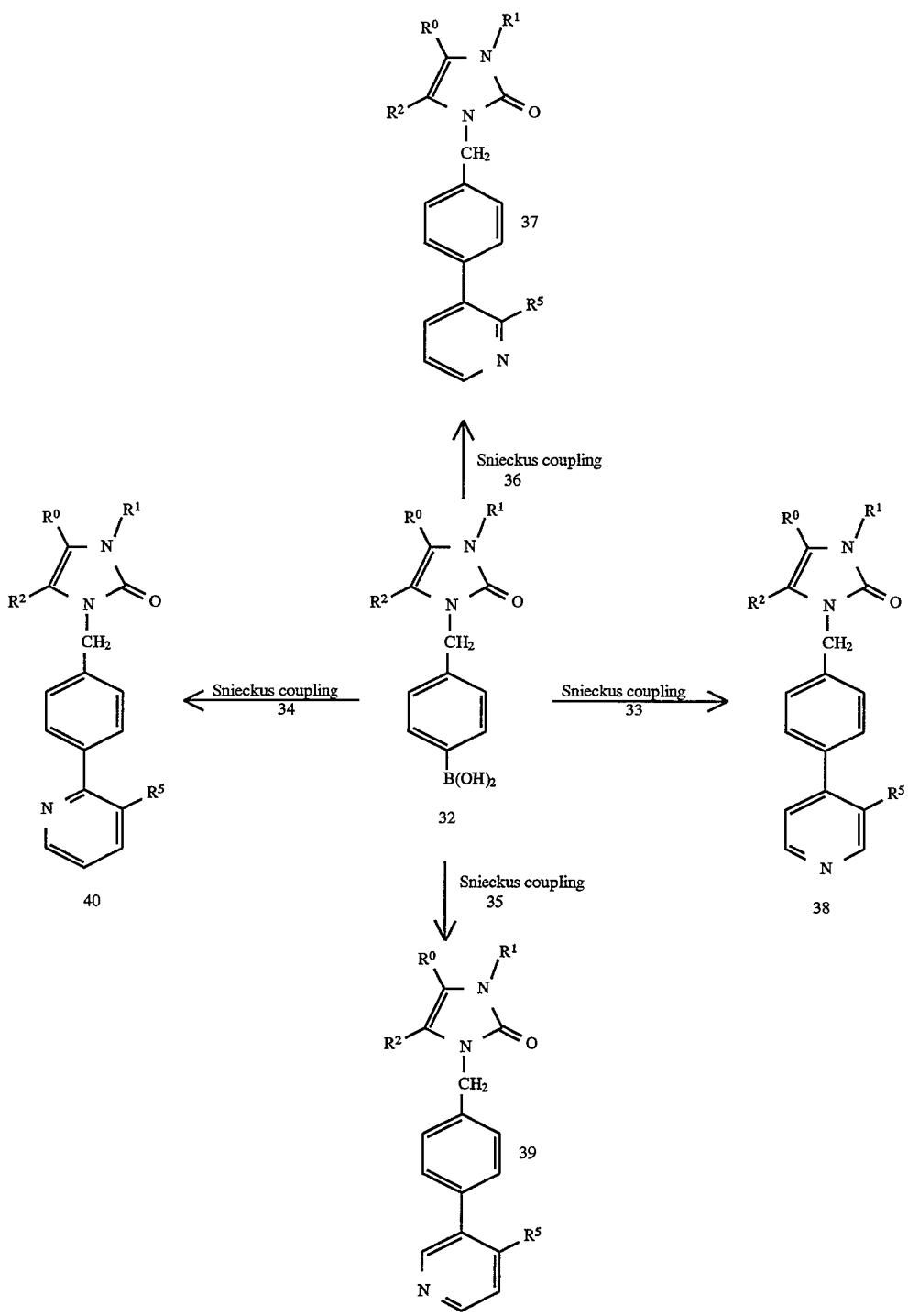

Synthetic Scheme XIX shows the preparation of 3-(pyridinylbenzyl)imidazol-2-ones 37, 38, 39 and 40 from the common imidazol-2-one boronic acids 32 (Scheme XV) and the corresponding bromo coupling reagents 36 (Scheme XVIII), 33 (Scheme XVI), 35 (Scheme XVII), and 34 (Scheme XVI), respectively. The boronic acids 32 are reacted with the bromo coupling reagents 36, 33, 35 and 34 in the presence of a palladium zero catalyst via a Snieckus coupling [see M. J. Sharp and V. Snieckus, *Tetrahedron Lett.*, 5997 (1985)] to give the angiotensin II antagonists 37, 38, 39 and 40, respectively, of this invention.

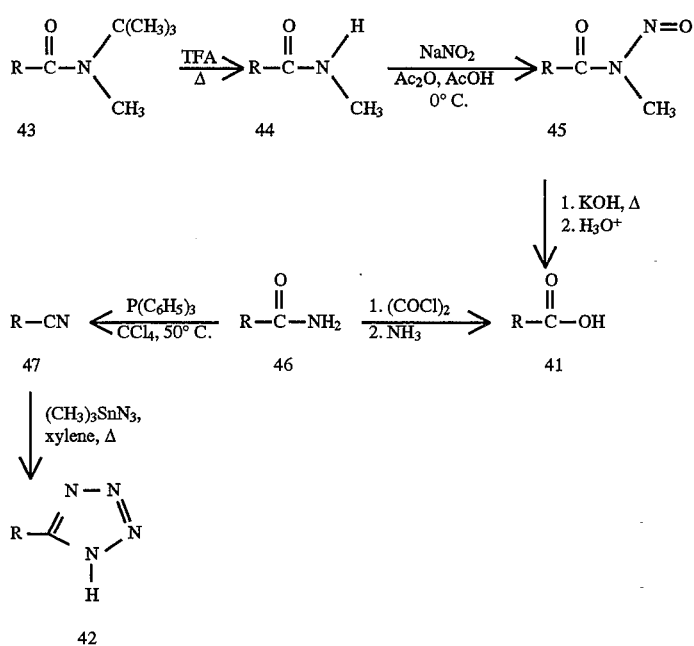

EXAMPLE 1

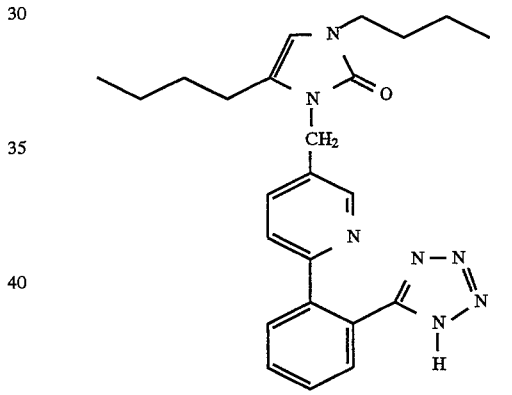

1,4-dibutyl-1,3-dihydro-3-[[6-[2-(1H-tetrazol-5-yl)phenyl]-3-pridinyl]methyl]-2H-imidazol-2-one Synthetic Scheme XX shows the preparation of carboxylic acid analogs 41 and 1H-tetrazole analogs 42 from analogs which have $R^5$=CON(CH$_3$)C(CH$_3$)$_3$. In step 1, the N-tertbutyl-N-methylamide analog 43 is reacted with trifluoroacetic acid at reflux to give the N-methylamide 44. In step 2, the N-methylamide 44 is reacted with sodium nitrite in acetic anhydride/acetic acid at 0° C. to give the corresponding N-methyl-N-nitrosoamide 45. In step 3, the N-methyl-N-nitrosoamide 45 is hydrolyzed in bake to give the corresponding carboxylic acid angiotensin II antagonists of this invention. In step 4, the acid analog 41 is reacted with oxalyl chloride and subsequently with anhydrous ammonia to give the primary amide 46. In step 5, the amide 46 is reacted with triphenylphosphine in carbon tetrachloride at 50° C. to give the corresponding nitrile 47. In step 6, the nitrile 47 is reacted with trimethyltin azide in xylene at reflux to provide the 1H-tetrazole angiotensin II antagonists of this invention.

The following Example contains detailed descriptions of the methods of preparation of compounds of Formula I. These detailed descriptions fall within the scope of, and serve to exemplify, the above described General Synthetic Procedures which form part of the invention. These detailed descriptions are presented for illustrative purposes only and are not intended as a restriction on the scope of the invention. All parts are by weight and temperatures are in degrees Centigrade, unless otherwise indicated.

Step 1: Preparation of N-t-BoC-L-norleucine-N-methoxy-N-methylamide

Under nitrogen, a stirred solution of 400 g (1.73 mol) of N-t-Boc-norleucine (BACHEM) and 193 g (1.9 mol) of triethylamine (TEA) in 3000 mL of dichloromethane (DCM) at −50° C. was treated with 258 g (1.9 mol) of isobutyl chlorformate. After 30 min, 203 g (2.08 mol) of solid N,O-dimethylhydroxylamine hydrochloride was added followed by 210.5 g (2.08 mol) of TEA at such a rate as to maintain the reaction temperature at −35° C. The reaction was stirred at −15° C. for 1 h and then allowed to warm to ambient temperature and stir overnight. The reaction was washed with 1M citric acid, NaHCO$_3$ (sat), and brine. The solution was dried (Na$_2$SO$_4$) and concentrated in vacuo to give 499.3 g of crude product as a pale green oil: NMR (CDCl$_3$) δ 0.88 (t, J=7 Hz, 3H), 1.28–1.38 (m, 4H), 1.43 (s, 9H), 1.49–1.57 (m, 1H), 1.63–1.75 (m, 1H), 3.20 (s, 3H), 3.76 (s, 3H), 4.60–4.72 (m, 1H), 5.13 (d, J=8 Hz, 1H).

Step 2A: Preparation of 1,4-dibutyl-1,3-dihydro-2H-imidazol-2-one: Method A.

Under nitrogen, a stirred solution of 449 g of crude N-t-Boc-L-norleucine-N-methoxy-N-methylamide from Step 1 in 1350 mL of methylene chloride at 0° C. was treated with 1350 mL of trifluoroacetic acid (TFA). The reaction was allowed to warm to ambient temperature and stir. After 2 h, the reaction was concentrated in vacuo to give the TFA salt of L-norleucine-N-methoxy-N-methylamide as a viscous colorless oil: NMR (CDCl$_3$) δ 0.88 (t, J=7 Hz, 3H), 1.30–1.40 (m, 4H), 1.88 (t, J=7 Hz, 2H), 3.25 (s, 3H), 3.75 (s, 3H), 4.35–4.46 (m, 1H), 7.55–7.76 (br s, 3H). The TFA salt was cooled to 0° C. and treated with aqueous sodium hydroxide until the pH was 10. The resulting solution was continuously extracted with ether for 24 h, continuously extracted with ether/DCM (3:1) for 24 h, and continuously extracted with ether/DCM (1:1) for 24 h. The organic layer was dried (Na$_2$SO$_4$) and concentrated in vacuo to give 245 g (83% from N-t-Boc-norleucine) as the monohydrate. Under nitrogen, a solution of this material in 100 mL of chloroform at 0° C., was slowly treated with 208 g (2.1 mol) of neat n-butylisocyanate over 15 min. The reaction was allowed to warm to ambient temperature and stir for 3 h. The reaction was concentrated in vacuo; purification by silica gel chromatography (Waters Prep-500A) using ethyl acetate gave 299.5 g as a colorless oil: NMR (CDCl$_3$) δ 0.83–0.95 (m, 6H), 1.25–1.47 (m, 8H), 1.48–1.60 (m, 1H), 1.63–1.75 (m, 1H), 3.02–3.26 (m, 2H), 3.21 (s, 3H), 3.84 (s, 3H), 4.82–4.93 (m, 1H). Under nitrogen, 299 g (1.09 mol) of this material was dissolved in 600 mL of anhydrous diethyl ether; the solution was cooled to −15° C. and slowly treated with 720 mL (720 mmol) of a 1.0M solution of lithium aluminum hydride (LAH) in ether. The reaction was allowed to warm to ambient temperature and stir overnight prior to the addition of 50 mL of ethyl acetate. A solution of 285 g (2 mol) of potassium bisulfate in 1500 mL of water was added cautiously and the reaction stirred for 4 h. The reaction mixture was transferred to a separatory funnel and the phases separated. The aqueous phase was extracted 8 times with additional ether. The combined ether extracts were washed 3 times each with 3N hydrochloric acid, saturated sodium bicarbonate, and brine. The ether extracts were then dried (MgSO$_4$) and concentrated in vacuo to give 228 g (68% from N-t-Boc-norleucine) of 1,4-dibutyl-1,3-dihydro-2H-imidazol-2-one as a viscous colorless oil which solidified on storage in the refrigerator: NMR (CDCl$_3$) δ 0.91 (t, J=7 Hz, 3H), 0.93 (t, J=7 Hz, 3H), 1.28–1.41 (m, 4H), 1.47–1.65 (m, 4H), 2.36 (td, J=7 and 1 Hz, 2H), 3.55 (t, J=7 Hz, 2H), 5.84 (t, J=1 Hz, 1H), 9.78 (br s, 1H).

Step 2B: Preparation of 1,4-dibutyl-1,3-dihydro-2H-imidazo-2-one: Method B

Under nitrogen, a stirred solution of 67.8 g (0.26 mol) of N-t-Boc-norleucine-N-methoxy-N-methylamide from Step 1 in 550 mL of anhydrous diethyl ether at 0° C. was treated with 145 mL (145 mmol) of a 1M solution of lithium aluminum hydride (LAH) in ether over a 30 min period. The reaction was allowed to stir for an additional 30 min and then was quenched with the addition of 10 mL of ethyl acetate. The reaction was diluted with 1 L of cold water to which 63 g (0.46 mol) of potassium hydrogen sulfate had been added and the mixture stirred vigorously for 15 min. The phases were separated and the aqueous phase extracted 4 times with ether; the extracts were combined, washed 3 times with 3N hydrochloric acid, once with saturated sodium bicarbonate, and once with brine, dried (Na$_2$SO$_4$) and concentrated in vacuo to give 47.6 g (84%) of N-t-Boc-L-norleucinal as a colorless waxy solid: NMR (CDCl$_3$) δ 0.91 (t, J=7 Hz, 3H), 1.34–1.41 (m, 4H), 1.46 (s, 9H), 1.55–1.64 (m, 1H), 1.80–1.95 (m, 1H), 4.16–4.30 (m, 1H), 5.07–5.15 (m, 1H), 9.59 (s, 1H). Under nitrogen, a stirred solution of 10.0 g (46.4 mmol) of this material in 10 mL of dioxane (anhydrous) at 0° C. was treated with 120 mL (480 mmol) of 4N hydrogen chloride in dioxane over a 10 min period. The reaction was allowed to stir at 0° C. for an additional 20 min after the addition was complete and then concentrated in vacuo. The residue was dissolved in 200 mL of chloroform and treated with 77.4 g (0.78 mol) of butyl isocyanate. The mixture was stirred at ambient temperature for 24 h, stirred at 40° C. for 24 h, and concentrated in vacuo. Purification of the reddish colored residue by silica gel chromatography (Harrison Chromatotron) using ethyl acetate/2-propanol (95:5) gave 160 mg (1.7% from N-t-Boc-L-norleucinal) of 1,4-dibutyl-1,3-dihydro2H-imidazol-2-one as an yellowish oil: NMR (CDCl$_3$) δ 0.91 (t, J=7 Hz, 3H), 0.93 (t, J=7 Hz, 3H), 1.28–1.41 (m, 4H), 1.47–1.65 (m, 4H), 2.36 (td, J=7 and 1 Hz, 2H), 3.55 (t, J=7 Hz, 2H), 5.84 (t, J=1 Hz, 1H), 9.78 (br s, 1H); MS (FAB) m/e (rel intensity) 197 (100), 153 (12), 141 (t2), 125 (8), 111 (7).

Step 2C: Preparation of 1,4-dibutyl-1,3-dihydro-2H-imidazol-2-one: Method C

Under nitrogen, a solution of 27.0 g (125 mmol) of N-t-Boc-L-norleucinal from step 2B, 39.1 g (376 mmol) of 2,2-dimethyl-1,3-propanediol, and 1.18 g (6.2 mmol) of p-toluenesulfonic acid monohydrate in 220 mL of benzene was stirred at reflux for 22 h over a Dean-Stark trap. The reaction was cooled, diluted with 300 mL of ethyl acetate, washed sequentially with saturated sodium bicarbonate and brine, dried (Na$_2$SO$_4$), and concentrated in vacuo to give 38.27 g of crude ketal which was a red oil: NMR (CDCl$_3$) δ 0.71 (s, 3H), 0.89 (t, J=7Hz 3H), 1.16 (s, 3H), 1.20–1.52 (m, 5H), 1.45 (s, 9H), 1.58–1.72 (m, 1H), 3.35–3.46 (m, 2H), 3.56–3.63 (m, 2H), 4.43 (s, 1H), 4.66 (d, J=9 Hz, 1H). Under nitrogen, a 38.2 g sample of the crude ketal was dissolved in 200 mL of methylene chloride; the solution was cooled to 0° C. and treated with 200 mL of trifluoracetic acid. The reaction was allowed to warm to ambient temperature and stir for 2 h. Concentration in vacuo gave the crude TFA salt of the free amino ketal as a red viscous oil: NMR (CDCl$_3$) δ 0.75 (s, 3H), 0.90 (t, J=7 Hz, 3H), 1.13 (s, 3H), 1.27–1.42 (m, 4H), 1.60–1.82 (m, 2H), 3.27–3.38 (m, 1H), 3.42–3.52 (m, 2H), 3.63–3.72 (m, 2H), 4.58 (d, J=3 Hz, 1H), 7.1–7.5 (br s, 3H). Under nitrogen, the crude TFA salt was redissolved in 100 mL of methylene chloride and treated with 264 g (2.66 mol) of butyl isocyanate. The reaction was stirred at ambient temperature for 17 h. The reaction was concentrated in vacuo to give the crude N-butyl urea of the ketal as a red oil. Purification of a small sample by silica gel chromatography (Harrison Chromatotron) using ethyl acetate/hexane (1:1) gave the pure N-butyl urea as a pale yellow oil: NMR (CDCl$_3$) δ 0.71 (s, 3H), 0.89 (t, J=7 Hz, 3H), 0.92 (t, J=7 Hz, 3H), 1.16 (s, 3H), 1.23–1.54 (m, 9H), 1.61–1.75 (m, 1H), 3.09–3.21 (m, 2H), 3.37–3.46 (m, 2H), 3.56–3.64 (m, 2H), 3.68–3.79 (m, 1H), 4.32–4.47 (br s, 1H), 4.42 (d, J=3 Hz, 1H). Under nitrogen, a solution of the crude N-butyl urea ketal in 1 L of 1,4-dioxane was treated with 1 L of 6N hydrochloric acid. The reaction was allowed to stir at ambient temperature for 16 h and then warmed to 60° C. and stirred for an additional 24 h. The reaction was concentrated in vacuo; the residue was treated with ethyl acetate and filtered. The ethyl acetate solution was dried (MgSO$_4$) and concentrated in vacuo to give the crude product. Purification by silica gel chromatography (Waters Prep-500A) using methylene chloride/2-propanol (95:5) gave 4.95 g (20% from N-t-Boc-L-norleucinal) of 1,4-dibutyl-1,3-dihydro-2-one as a pale yellow oil: NMR (CDCl$_3$) δ 0.91 (t, J=7 Hz, 3H), 0.93 (t, J=7 Hz, 3H) 1.28–1.41 (m, 4H), 1.47–1.65 (m, 4H), 2.36 (td, J=7 and 1 Hz, 2H), 3.55 (t, J=7 Hz, 2H), 5.84 (t, J=1 Hz, 1H), 9.78 (br s, 1H).

Step 3: Preparation of 2-bromo-5-picoline

A solution of 1500 mL (14 mol) of 48% hydrobromic acid was cooled to 10° C. and 300 g (2.8 mol) of 2-amino-5-picoline (Aldrich) was added slowly. The solution was maintained at or below 0° C. while 450 mL (8.8 mol) of bromine was added dropwise. After the bromine addition was complete, a solution of 500 g (7.3 mol) of sodium nitrite in 1000 mL of water was added slowly over 6 h. The reaction pH was adjusted by the careful addition of 1500 mL (56 mol) of 50% sodium hydroxide at such a rate that the temperature was maintained below 30° C. The product precipitated from the nearly colorless reaction mixture; filtration gave 450 g (94%) of 2-bromo-5-picoline as a yellow powder: mp 38°–40° C.; NMR 7.27 (s, 1H), 7.28 (s, 1H), 7.12 (br s, 1H).

Step 4: Preparation of 2-bromo-5-bromomethylpyridine

A solution of 296.3 g (1.72 mol) of 2-bromo-5-picoline from step 3 in 6 L of carbon tetrachloride was treated with 306.5 g (1.72 mol) of N-bromosuccinimide (NBS) and 28.3 g (173 mmol) of azobisisobutyronitrile (AIBN). The reaction was stirred at reflux under nitrogen for 3 h, filtered, and concentrated in vacuo providing 476 g of crude 2-bromo-5-bromomethylpyridine as a brownish yellow solid (NMR indicates that this material is only 69% monobromomethyl product): NMR (CDCl$_3$) δ 4.42 (s, 2H), 7.48 (d, J=9 Hz, 1H), 7.60 (dd, J=9 and 3 Hz, 1H), 8.37 (d, J=3 Hz, 1H).

Step 5: Preparation of 1,4-dibutyl-1,3-dihydro-3-[(6-bromo-3-pyridinyl)methyl]-2H-imidazol-2-one Under nitrogen, 138 mL (138 mmol) of 1.0M potassium t-butoxide in THF was added to a stirred solution of 24.5 g (125 mmol) of 1,4-dibutylimidazol-2-one from step 2A in 370 mL of DMF at −30° C. at such a rate to maintain the solution temperature below −20° C. After 10 min, 50 g [138 mmol (69% purity)] of 2-bromo-5-bromomethylpyridine from step 4 and 2.7 g (18.1 mmol) of sodium iodide were added. The reaction was stirred at 0° C. for 2 h and then allowed to slowly warm to ambient temperature overnight. The reaction was partitioned between ethyl acetate and water; the organic layer was washed twice with brine and the combined aqueous phases were back-extracted with ethyl acetate. The ethyl acetate extractions were combined, dried (MgSO$_4$), and concentrated in vacuo. Purification by silica gel chromatography (Waters Prep-500A) using hexane/ethyl acetate (25:75) gave 33 g (73%) of 1,4-dibutyl-1,3-dihydro-3-[(6-bromo-3-pyridinyl)methyl]-2H-imdazol-2-one as a reddish-brown waxy solid: NMR (CDCl$_3$) δ 0.89 (t, J=7 Hz, 3H), 0.95 (t, J=7 Hz, 3H), 1.25–1.51 (m, 6H), 1.57–1.71 (m, 2H), 2.22 (t, J=8 Hz, 2H), 3.60 (t, J=7 Hz, 2H), 4.80 (s, 2H), 5.90 (s, 1H), 7.43 (d, J=9 Hz, 1H), 7.49 (dd, J=9 and 2 Hz, 1H), 8.24 (d, J=2 Hz, 1H).

Step 6: Preparation of 2-(N-triphenylmethyltetrazol-5-yl) phenylboronic acid

A 64 g (350 mmol) sample of 2-bromobenzonitrile (Aldrich) was dissolved in 650 mL of xylene and treated with 22.75 g (350 mmol) of sodium azide and 95 mL (350 mmol) of tributyltin chloride at reflux for 48 h. The reaction was filtered; the filtrate was treated with 50 mL of anhydrous tetrahydrofuran (THF) and 20 g (550 mmol) of hydrogen chloride. The reaction was stirred for 2 h; filtration gave 59.6 g (76%) of 5-(2-bromophenyl)-1H-tetrazole: mp 178°–180° C.; NMR (DMSO-d$_6$) δ 7.50–7.64 (m, 2H), 7.67–7.74 (m, 1H), 7.83–7.91 (m, 1H). A 41.8 g (187 mmol) sample of this material was dissolved in 650 mL of methylene chloride and treated with 55.5 g (193 mmol) of triphenylmethyl chloride and 30 mL (220 mmol) of anhydrous triethylamine. The reaction was stirred overnight at reflux, cooled to ambient tempeature, washed with water, dried (MgSO$_4$), and concentrated in vacuo. Recrystallization from toluene/hexane gave 80.7 g (92%) of N-triphenylmethyl-5-(2-bromophenyl)-1H-tetrazole: mp 160°–162° C.; NMR (CDCl$_3$) δ 7.14–7.21 (m, 6H), 7.26–7.45 (m, 11H), 7.70 (dd, J=8 and 1.5 Hz, 1H), 7.89 (dd, J=7.5 and 2 Hz, 1H). A 34.05 g (73.0 mmol) sample of this material was dissolved in 1700 mL of THF under a nitrogen atmosphere and treated with 73 mmol of n-butyllithium in hexane. The reaction was allowed to stir for 17 min and then was treated with 24.9 mL (220 mmol) of trimethyl borate. The reaction was allowed to come to ambient temperature overnight while stirring, quenched with 10 mL of methanol, and concentrated in vacuo. The residue was dissolved in 1M NaOH and extracted with toluene to remove any unreacted starting material. The pH was adjusted to 6 with 6M HCl and the product extracted with toluene and dried (MgSO$_4$). Hexane was added and the solution kept in the freezer overnight. Filtration provided 31.3 g (99%) of 2-(N-triphenylmethyltetrazol-5-yl) phenylboronic acid: NMR (CDCl$_3$) δ 7.13–7.21 (m, 7H), 7.33–7.42 (m, 8H), 7.49–7.55 (m, 2H), 8.15–8.19 (m, 1H), 8.21–8.26 (m, 1H).

Step 7: Preparation of 1,4-dibutyl-1,4-dihydro-3-[[6-[2-(1H-tetrazol-5-yl)phenyl]-3-pyridinyl]methyl]-2H-imidazo-2-one A solution of 21.7 g (50.2 mmol) of 2-(N-triphenylmethyltetrazol-5-yl)phenylboronic acid from step 6 in 80 mL of ethanol and 130 mL of toluene was added to a mixture of 5 g (4 mmol) of tetrakis (triphenylphosphine) Pd(0), 16.75 g (45.8 mmol) of 1,4-dibutyl-1,3-dihydro-3-[(6-bromo-3-pyridinyl)methyl]-2H-imidazol-2-one from step 5, 225 mL of toluene, 100 mL of 2M sodium carbonate, and 150 mL of ethanol. The reaction mixture was heated to reflux and vigorously stirred under nitrogen for 14 h. The pH was adjusted to 6 with acetic acid and the reaction concentrated in vacuo. The product was.purified by silica gel chromatography (Waters Prep-500A) using 2-propanol/methylene chloride (0–50%) followed by reverse phase chromatography (Waters Deltaprep-3000) using acetonitrile/water (30–35:70-65) (0.05% TFA). The pure fractions (by analytical HPLC) were combined, the acetonitrile removed in vacuo, and the water extracted 4 times with chloroform. The extracts were combined, dried (MgSO$_4$), and concentrated in vacuo. Recrystallization from ethyl acetate gave 8.5 g (43%) of colorless 1,4-dibutyl-1,3-dihydro-3-[[6-[2-(1H-tetrazol-5-yl)phenyl]-3-pyridinyl]methyl]-2H-imidazol-2-one as a colorless solid: mp 170°–171° C.; NMR (CDCl$_3$) δ 0.88 (t, J=7 Hz, 3H), 0.96 (t, J=7 Hz, 3H), 1.28–1.54 (m, 6H), 1.61–1.72 (m, 2H), 2.28 (t, J=8 Hz, 2H), 3.63 (t, J=7 Hz, 2H), 4.96 (s, 2H), 5.96 (s, 1H), 7.36 (d, J=9 Hz, 1H), 7.47–7.58 (m, 3H), 7.67 (dd, J=9 and 2 Hz, 1H), 8.06–8.13 (m, 1H), 8.52 (d, J=2 Hz, 1H); MS (FAB) m/e (rel intensity) 432 (100), 404 (18), 237 (14), 209 (92), 180 (82); HRMS. Calc'd for M+H: 432.2512. Found: 432.2554. Anal. Calc'd for C$_{24}$H$_{29}$N$_7$O: C, 66.80; H, 6.77; N, 22.72. Found: C, 66.59; H, 6.85; N, 22.57.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mMEDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM $MgCl_2$, 2 m MEDTA, 0.5% bovine serum albumin, 50 mM Tris-HCl pH 7.5 and $^{125}$I-AII (approximately $10^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 µM of unlabelled AII. Specific binding was calculated as total binding minus nonspecific binding. The receptor binding affinity of an AII antagonist compound was indicated by the concentration ($IC_{50}$) of the tested AII antagonist which gives 50% displacement of the total specifically bound $^{125}$I-AII from the high affinity AII receptor. Binding data were analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 $NaHCO_3$, 15 KCl, 1.2 $NaH_2PO_4$, 1.2 $MgSO_4$, 2.5 $CaCl_2$, and 11.4 glucose. The preparations were equilibrated for one hour before approximately one gram of passive tension was placed on the rings. Angiotensin II concentration-response curves were then recorded ($3\times10^{-10}$ to $1\times10^{-5}$ M). Each concentration of AII was allowed to elicit its maximal contraction, and then AII was washed out repeatedly for 30 minutes before rechallenging, with a higher concentration of AII. Aorta rings were exposed to the test antagonist at $10^{-5}$ M for 5 minutes before challenging with AII. Adjacent segments of the same aorta ring were used for all concentration-response curves in the presence or absence of the test antagonist. The effectiveness of the test compound was expressed in terms of $pA_2$ values and were calculated according to H. O. Schild [*Br. J. Pharmcol. Chemother.*, 2, 189–206 (1947)]. The $pA_2$ value is the concentration of the antagonist which increases the $EC_{50}$ value for AII by a factor of two. Each test antagonist was evaluated in aorta rings from two rabbits. Results are reported in Table I.

TABLE I

| | In Vitro Angiotensin II Activity of Compounds of the Invention | |
|---|---|---|
| Test Compound Example # | [1]Assay A $IC_{50}$ (nM) | [2]Assay B $pA_2$ |
| 1 | 6.5 | 8.68 |

[1]Assay A: Angiotensin II Binding Activity
[2]Assay B: In Vitro Vascular Smooth Muscle Response Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A method for treating a glaucoma disorder related to elevated intraocular pressure, which elevated intraocular pressure is mediated by action of an angiotensin II receptor antagonist, said method comprising administering to a subject susceptible to or afflicted with such glaucoma disorder a therapeutically-effective amount of an angiotensin II receptor antagonist compound of Formula I

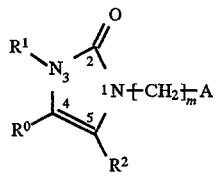

wherein A is selected from

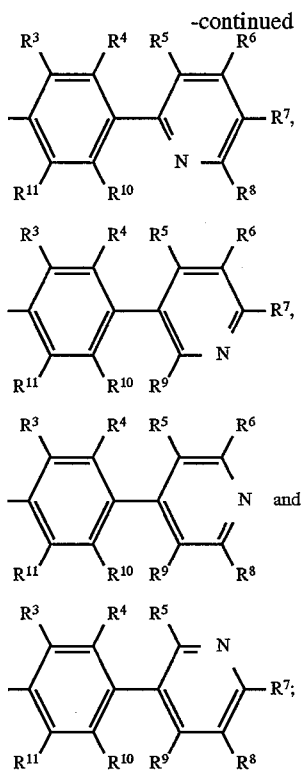

wherein m is one; wherein $R^1$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxoethyl, 1-oxopropyl, 1-oxobutyl, 1-oxopentyl, 2-butenyl, 3-butenyl, 2-butynyl, 3-butynyl and 2-hydroxybutyl; wherein $R^o$ is selected from hydrido, $C_4H_9$ (n), $CH_3CH_2CH=CH$, $C_3H_7$(n), $SC_3H_7$,

$C_2H_5$, $C_5H_{11}$(n), $C_6H_{13}$(n), $SC_4H_9$,

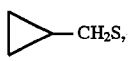

$CH_3CH=CH$, $CH_3CH_2CH_2CH=CH-$, amino, aminomethyl, aminoethyl, aminopropyl, $CH_2OH$, $CH_2OCOCH_3$, $CH_2Cl$, $CH_2OCH_3$, $CH_2OCH(CH_3)_2$, CHO, $CH_2CO_2H$, $CH(CH_3)CO_2H$,

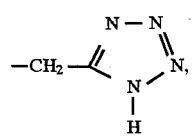

-continued

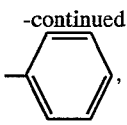

—CO$_2$CH$_3$, —CONH$_2$, —CONHCH$_3$, CON(CH$_3$)$_2$, —CH$_2$—NHCO$_2$C$_2$H$_5$,

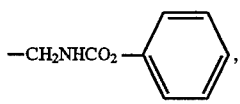

—CH$_2$NHCO$_2$CH$_3$, —CH$_2$NHCO$_2$C$_3$H$_7$, —CH$_2$NHCO$_2$CH$_2$(CH$_3$)$_2$, —CH$_2$NHCO$_2$C$_4$H$_9$, CH$_2$NHCO$_2$-adamantyl, —CH$_2$NHCO$_2$-(1-napthyl), —CH$_2$NHCONHCH$_3$, —CH$_2$NHCONHC$_2$H$_5$, —CH$_2$NHCONHC$_3$H$_7$, —CH$_2$NHCONHC$_4$H$_9$, —CH$_2$NHCONHCH(CH$_3$)$_2$, —CH$_2$NHCONH(1-napthyl), —CH$_2$NHCONH(1-adamantyl), CO$_2$H,

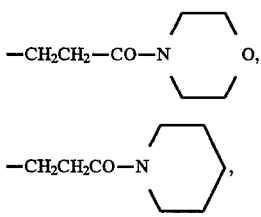

—CH$_2$CH$_2$CH$_2$CO$_2$H, —CH$_2$CH$_2$F, —CH$_2$OCONHCH$_3$, —CH$_2$OCSNHCH$_3$, —CH$_2$NHCSOC$_3$H$_7$, —CH$_2$CH$_2$CH$_2$F, —CH$_2$ONO$_2$,

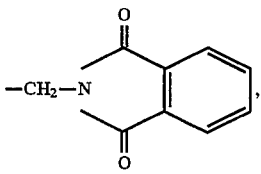

—CH$_2$SH,

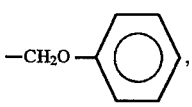

H, NO$_2$,CF$_3$, Br, Cl, F, I, methyl, ethyl, n-propyl, isopropyl, -butyl, sec-butyl, isobutyl, tert-butyl, n-pentyl, isopentyl, neopentyl, phenyl, cyclohexyl, cyclohexylmethyl, carboxyl, formyl, 1-oxoethyl, 1-oxopropyl, 1-oxobutyl, 1-oxopentyl, dimethoxymethyl, 1,1-dimethoxypropyl, 1,1-dimethoxypentyl, hydroxyalkyl, halo, 1-oxo-2-phenylethyl, 1-oxo-2-cyclohexylethyl, 1,1-difluoro-2-phenylethyl, monofluoromethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, difluoromethyl, CO$_2$H, SH, PO$_3$H$_2$, SO$_3$H, CONHNH$_2$, CONHNHSO$_2$CF$_3$, OH,

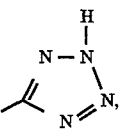

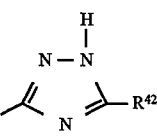

and

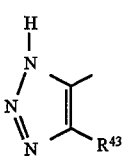

wherein each of R$^{42}$ and R$^{43}$ is independently selected from chloro, cyano, nitro, trifluoromethyl, methoxycarbonyl and trifluoromethylsulfonyl; wherein R$^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of R$^3$ through R$^{11}$ is hydrido with the proviso that at least one of R$^5$, R$^6$, R$^8$ and R$^9$ is an acidic group selected from CO$_2$H, SH, PO$_3$H$_2$, SO$_3$H, CONHNH$_2$, CONHNHSO$_2$CF$_3$, OH,

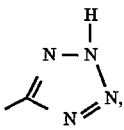

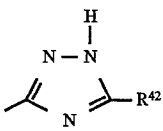

and

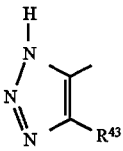

wherein each of R$^{42}$ and R$^{43}$ is independently selected from chloro, cyano, nitro, trifluoromethyl, methoxycarbonyl and trifluoromethylsulfonyl;

or a tautomer thereof or a pharmaceutically-acceptable salt thereof.

2. The method of claim 1 wherein m is one; wherein R$^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxoethyl, 1-oxopropyl, 1-oxo-butyl, 1-oxo-pentyl, 2-butenyl, 3-butenyl, 2-butynyl, 3-butynyl and 2-hydroxybutyl; wherein R$^o$ is selected from hydrido, methyl, ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, fluoro, chloro, monofluoromethyl, difluoromethyl, trifluoromethyl, formyl, carboxyl, dimethoxymethyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylmethyl, cyclohexylethyl, cyclohexanoyl, 1-butenyl, 2-butenyl, 3-butenyl, 1-butynyl, 2-butynyl, 3-butynyl, propylthio, butylthio, CO$_2$H, SH, PO$_3$H$_2$, SO$_3$H, CONHNH$_2$, CONHNHSO$_2$CF$_3$, OH,

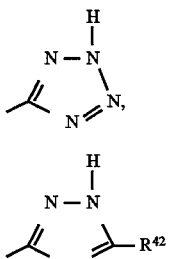

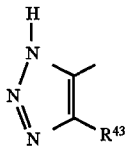

wherein each of R$^{42}$ and R$^{43}$ is independently selected from chloro, cyano, nitro, trifluoromethyl, methoxycarbonyl and trifluoromethylsulfonyl; wherein R$^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of R$^3$ through R$^{11}$ is hydrido with the proviso that at least one of R$^5$, R$^6$, R$^8$ and R$^9$ is an acidic group selected from CO$_2$H, SH, PO$_3$H$_2$, SO$_3$H, CONHNH$_2$, CONHNHSO$_2$CF$_3$, OH,

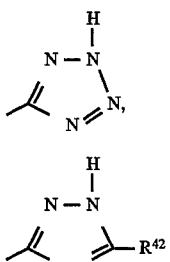

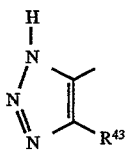

wherein each of R$^{42}$ and R$^{43}$ is independently selected from chloro, cyano, nitro, trifluoromethyl, methoxycarbonyl and trifluoromethylsulfonyl;

or a tautomer thereof or a pharmaceutically-acceptable salt thereof.

3. The method of claim 2 wherein m is one; wherein R$^1$ is selected from methyl, ethyl, n-propyl, isopropyl, n-butyl, sec-butyl, isobutyl, tertbutyl, 4-methylbutyl, n-pentyl, neopentyl, phenyl, benzyl, phenethyl, cyclohexyl, cyclohexylmethyl, cyclohexylethyl cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein R$^0$ is selected from hydrido, methyl, ethyl, n-propyl, isopropyl, n-butyl, sec-butyl, isobutyl, 4-methylbutyl, n-pentyl, 1-oxo-2-phenylethyl, 1-oxo-2-cyclohexylethyl, fluoro, chloro, monofluoromethyl, difluoromethyl, trifluoromethyl, formyl, carboxyl, dimethoxymethyl, 1,1-difluoro-2-phenylethyl, 1,1-difluoro-2-cyclohexylethyl, 2-cyclohexylethyl, 1,1-difluoro-3-cyclohexylpropyl, dimethoxymethyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexylethyl, cyclohexanoyl, 1-butenyl, 2-butenyl, 3-butenyl, 1-butynyl, 2-butynyl, 3-butynyl, propylthio and butylthio; wherein R$^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of R$^3$, R$^4$, R$^6$, R$^7$, R$^8$, R$^{10}$ and R$^{11}$ is hydrido; wherein one of R$^5$ and R$^9$ is hydrido and the other of R$^5$ and R$^9$ is an acidic group selected from COOH, SH, PO$_3$H$_2$, SO$_3$H, CONHNH$_2$, CONHNHSO$_2$CF$_3$, OH,

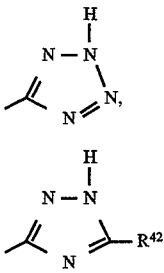

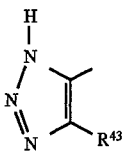

wherein each of R$^{42}$ and R$^{43}$ is independently selected from chloro, cyano, nitro, trifluoromethyl, methoxycarbonyl and trifluoromethylsulfonyl;

or a tautomer thereof or a pharmaceutically-acceptable salt thereof.

4. The method of claim 3 wherein m is one; wherein R$^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein R$^0$ is selected from hydrido, methyl, fluoro, chloro, monofluoromethyl, difluoromethyl, trifluoromethyl, formyl, carboxyl and dimethoxymethyl; wherein R$^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of R$^3$, R$^4$, R$^6$, R$^7$, R$^8$, R$^{10}$ and R$^{11}$ is hydrido; with the proviso that at least one of R$^5$ and R$^9$ must be selected from COOH, SH, $PO_3H_2$, $SO_3H$, $CONHNH_2$, $CONHNHSO_2CF_3$, OH,

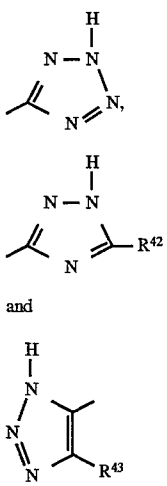

and

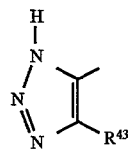

wherein each of $R^{42}$ and $R^{43}$ is independently selected from chloro, cyano, nitro, trifluoromethyl, methoxycarbonyl and trifluoromethylsulfonyl;
or a tautomer thereof or a pharmaceutically-acceptable salt thereof.

5. The method of claim 4 wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, cyclohexylethyl, propylthio, butylthio, and hydroxyalkyl; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from $CO_2H$ and

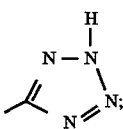

or a tautomer thereof or a pharmaceutically-acceptable salt thereof.

6. The method of claim 5 wherein said angiotensin II receptor antagonist compound is selected from a family of compounds of Formula II

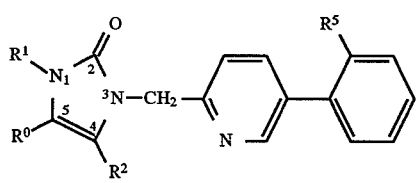

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

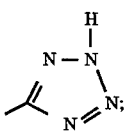

or a tautomer thereof or a pharmaceutically-acceptabler salt thereof.

7. The method of claim 6 wherein said angiotensin II receptor antagonist compound is selected from compounds and their pharmaceutically-acceptable salts of the group of compounds consisting of 1-propyl-4-butyl-1,3-dihydro-3-[[5-[2-(1H-tetrazol-5-yl)phenyl]-2-pyridinyl]methyl]-2H-imidazol-2-one;

1,4-dibutyl-1,3-dihydro-3-[[5-[2-(1H-tetrazol-5-yl)phenyl]-2-pyridinyl]methyl]-2H-imidazol-2-one;

1-pentyl-4-butyl-1,3-dihydro-3-[[5-[2-(1H-tetrazol-5-yl)phenyl]-2-pyridinyl]methyl]-2H-imidazol-2-one;

1-isopentyl-4-butyl-1,3-dihydro-3-[[5-[2-(1H-tetrazol-5-yl)phenyl]-2-pyridinyl]methyl]-2H-imidazol-2-one;

1-cyclohexylmethyl-4-butyl-1,3-dihydro-3-[[5-[2-(1H-tetrazol-5-yl)phenyl]-2-pyridinyl]methyl]-2H-imidazol-2-one;

1-phenylmethyl-4-butyl-1,3-dihydro-3-[[5-[2-(1H-tetrazol-5-yl)phenyl]-2-pyridinyl]methyl]-2H-imidazol-2-one;

1-(2-cyclohexylethyl)-4-butyl-1,3-dihydro-3-[[5-[2-(1H-tetrazol-5-yl)phenyl]-2-pyridinyl]methyl]-2H-imidazol-2-one;

1-(2-phenylethyl)-4-butyl-1,3-dihydro-3-[[5-[2-(1H-tetrazol-5-yl)phenyl]-2-pyridinyl]methyl]-2H-imidazol-2-one;

1-propyl-4-butyl-5-methyl-1,3-dihydro-3-[[5-[2-(1H-tetrazol-5-yl)phenyl]-2-pyridinyl]methyl]-2H-imidazol-2-one;

1,4-dibutyl-5-methyl-1,3-dihydro-3-[[5-[2-(1H-tetrazol-5-yl)phenyl]-2-pyridinyl]methyl]-2H-imidazol-2-one;

1-pentyl-4-butyl-5-methyl-1,3-dihydro-3-[[5-[2-(1H-tetrazol-5-yl)phenyl]-2-pyridinyl]methyl]-2H-imidazol-2-one;

1-isopentyl-4-butyl-5-methyl-1,3-dihydro-3-[[5-[2-(1H-tetrazol-5-yl)phenyl]-2-pyridinyl]methyl]-2H-imidazol-2-one;

1-cyclohexylmethyl-4-butyl-5-methyl-1,3-dihydro-3-[[5-[2-(1H-tetrazol-5-yl)phenyl]-2-pyridinyl]methyl]-2H-imidazol-2-one;

1-phenylmethyl-4-butyl-5-methyl-1,3-dihydro-3-[[5-[2-(1H-tetrazol-5-yl)phenyl]-2-pyridinyl]methyl]-2H-imidazol-2-one;

1-(2-cyclohexylethyl)-4-butyl-5-methyl-1,3-dihydro-3-[[5-[2-(1H-tetrazol-5-yl)phenyl]-2-pyridinyl]methyl]-2H-imidazol-2-one;

1(2-phenylethyl)-4-butyt-5-methyl-1,3-dihydro-3-[[5-[2-(1H-tetrazol-5-yl)phenyl]-2-pyridinyl]methyl]-2H-imidazol-2-one;

1-propyl-4-butyl-5-chloro-1,3-dihydro-3-[[5-[2-(1H-tetrazol-5-yl)phenyl]-2-pyridinyl]methyl]-2H-imidazol-2-one;

1,4-dibutyl-5-chloro-1,3-dihydro-3-[[5-[2-(1H-tetrazol-5-yl)phenyl]-2-pyridinyl]methyl]-2H-imidazol-2-one;

1-pentyl-4-butyl-5-chloro-1,3-dihydro-3-[[5-[2-(1H-tetrazol-5-yl)phenyl]-2-pyridinyl]methyl]-2H-imidazol-2-one;

1-isopentyl-4-butyl-5-chloro-1,3-dihydro-3-[[5-[2-(1H-tetrazol-5-yl)phenyl]-2-pyridinyl]methyl]-2H-imidazol-2-one;

1-cyclohexylmethyl-4-butyl-5-chloro-1,3-dihydro-3-[[5-[2-(1H-tetrazol-5-yl)phenyl]-2-pyridinyl]methyl]-2H-imidazol-2-one;

1-phenylmethyl-4-butyl-5-chloro-1,3-dihydro-3-[[5-[2-(1H-tetrazol-5-yl)phenyl]-2-pyridinyl]methyl]-2H-imidazol-2-one;

1-(2-cyclohexylethyl)-4-butyl-5-chloro-1,3-dihydro-3-[[5-[2-(1H-tetrazol-5-yl)phenyl]-2-pyridinyl]methyl]-2H-imidazol-2-one; and 1-(2-phenylethyl)-4-butyl-5-chloro-1,3-dihydro-3-[[5-[2-(1H-tetrazol-5-yl)phenyl]-2-pyridinyl]methyl]-2H-imidazol-2-one.

8. The method of claim 5 wherein said angiotensin II receptor antagonist compound is selected from a family of compounds of Formula III

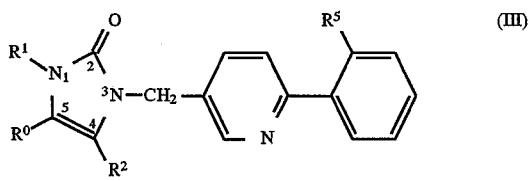

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylmethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

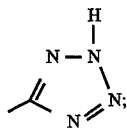

or a tautomer thereof or a pharmaceutically-acceptable salt thereof.

9. The method of claim 8 wherein said angiotensin II receptor antagonist compound is selected from compounds and their pharmaceutically-acceptable salts of the group of compounds consisting of 1-propyl-4-butyl-1,3-dihydro-3-[[6-[2-(1H-tetrazol-5-yl)phenyl]-3-pyridinyl]methyl]-2H-imidazol-2-one;

1,4-dibutyl-1,3-dihydro-3-[[6-[2-(1H-tetrazol-5-yl)phenyl]-3-pyridinyl]methyl]-2H-imidazol-2-one;

1-pentyl-4-butyl-1,3-dihydro-3-[[6-[2-(1H-tetrazol-5-yl)phenyl]-3-pyridinyl]methyl]-2H-imidazol-2-one;

1-isopentyl-4-butyl-1,3-dihydro-3-[[6-[2-(1H-tetrazol-5-yl)phenyl]-3-pyridinyl]methyl]-2H-imidazol-2-one;

1-cyclohexylmethyl-4-butyl-1,3-dihydro-3-[[6-[2-(1H-tetrazol-5-yl)phenyl]-3-pyridinyl]methyl]-2H-imidazol-2-one;

1-phenylmethyl-4-butyl-1,3-dihydro-3-[[6-[2-(1H-tetrazol-5-yl)phenyl]-3-pyridinyl]methyl]-2H-imidazol-2-one;

1-(2-cyclohexylethyl)-4-butyl-1,3-dihydro-3-[[6-[2-(1H-tetrazol-5-yl)phenyl]-3-pyridinyl]methyl]-2H-imidazol-2-one;

1-(2-phenylethyl)-4-butyl-1,3 -dihydro-3-[[6-[2-(1H-tetrazol-5-yl)phenyl]-3-pyridinyl]methyl]-2H-imidazol-2-one;

1-propyl-4-butyl-5-methyl-1,3-dihydro-3-[[6-[2-(1H-tetrazol-5-yl)phenyl]-3-pyridinyl]methyl]-2H-imidazol-2-one;

14-dibutyl-5-methyl-1,3-dihydro-3-[[6-[2-(1H-tetrazol-5-yl)phenyl]-3-pyridinyl]methyl]-2H-imidazol-2-one;

1-pentyl-4-butyl-5-methyl-1,3-dihydro-3-[[6-[2-(1H-tetrazol-5-yl)phenyl]-3-pyridinyl]methyl]-2H-imidazol-2-one;

1-isopentyl-4-butyl-5-methyl-1,3-dihydro-3-[[6-[2-(1H-tetrazol-5-yl)phenyl]-3-pyridinyl]methyl]-2H-imidazol-2-one;

1-cyclohexylmethyl-4-butyl-5-methyl-1,3-dihydro-3-[[6-[2-(1H-tetrazol-5-yl)phenyl]-3-pyridinyl]methyl]-2H-imidazol-2-one;

1-phenylmethyl-4-butyl-5-methyl-1,3-dihydro-3-[[6-[2-(1H-tetrazol-5-yl)phenyl]-3-pyridinyl]methyl]-2H-imidazol-2-one;

1-(2-cyclohexylethyl)-4-butyl-5-methyl-1,3-dihydro-3-[6-[2-(1H-tetrazol-5-yl)phenyl]-3-pyridinyl]methyl]-2H-imidazol-2-one;

1-(2-phenylethyl)-4-butyl-5-methyl-1,3-dihydro-3-[[6-[2-(1H-tetrazol-5-yl)phenyl]-3pyridinyl]methyl]-2H-imidazol-2-one;

1-propyl-4-butyl-5-chloro-1,3-dihydro-3-[[6-[2-(1H-tetrazol-5-yl)phenyl]-3-pyridinyl]methyl]-2H-imidazol-2-one;

1,4-dibutyl-5-chloro-1,3-dihydro-3-[[6-[2-(1H-tetrazol-5-yl)phenyl]-3-pyridinyl]methyl]-2H-imidazol-2-one;

1-pentyl-4-butyl-5-chloro-1,3-dihydro-3-[[6-[2-(1H-tetrazol-5-yl)phenyl]-3-pyridinyl]methyl]-2H-imidazol-2-one;

1-isopentyl-4-butyl-5-chloro-1,3-dihydro-3-[[6-[2-(1H-tetrazol-5-yl)phenyl]-3-pyridinyl]methyl]-2H-imidazol-2-one;

1-cyclohexylmethyl-4-butyl-5-chloro-1,3-dihydro-3-[[6-[2-(1H-tetrazol-5-yl)phenyl]-3-pyridinyl]methyl]-2H-imidazol-2-one;

1-phenylmethyl-4-butyl-5-chloro-1,3-dihydro-3-[[6-[2-(1H-tetrazol-5-yl)phenyl]-3-pyridinyl]methyl]-2H-imidazol-2-one;

1-(2-cyclohexylethyl)-4-butyl-5-chloro-1,3-dihydro-3-[6-[2-(1H-tetrazol-5-yl)phenyl]-3-pyridinyl]methyl]-2H-imidazol-2-one; and 1-(2-phenylethyl)-4-butyl-5-chloro-1,3-dihydro-3-[[6-[2-(1H-tetrazol-5-yl)phenyl]-3-pyridinyl]methyl]-2H-imidazol-2-one.

10. The method of claim 5 wherein said angiotensin II receptor antagonist compound is selected from a family of compounds of Formula IV

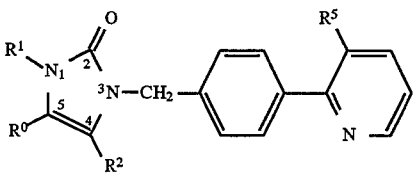

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

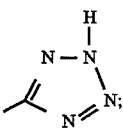

or a tautomer thereof or a pharmaceutically-acceptable salt thereof.

11. The method of claim 10 wherein said angiotensin II receptor antagonist compound is selected from compounds and their pharmaceutically-acceptable salts of the group of compounds consisting of 1-propyl-4-butyl-1,3-dihydro-3-[[4-[3-(1H-tetrazol-5-yl)-2-pyridinyl]phenyl]methyl]-2H-imidazol-2-one;

1,4-dibutyl-1,3-dihydro-3-[[4-[3-(1H-tetrazol-5-yl)-2-pyridinyl]phenyl]methyl]-2H-imidazol-2-one;

1-pentyl-4-butyl-1,3-dihydro-3-[[4-[3-(1H-tetrazol-5-yl)-2-pyridinyl]phenyl]methyl]-2H-imidazol-2-one;

1-isopentyl-4-butyl-1,3-dihydro-3-[[4-[3-(1H-tetrazol-5-yl)-2-pyridinyl]phenyl]methyl]-2H-imidazol-2-one;

1-cyclohexylmethyl-4-butyl-1,3-dihydro-3-[[4-[3-(1H-tetrazol-5-yl)-2-pyridinyl]phenyl]methyl]-2H-imidazol-2-one;

1-phenylmethyl-4-butyl-1,3-dihydro-3-[[4-[3-(1H-tetrazol-5-yl)-2-pyridinyl]phenyl]methyl]-2H-imidazol-2-one;

1-(2-cyclohexylethyl)-4-butyl-1,3-dihydro-3-[[4-[3-(1H-tetrazol-5-yl)-2-pyridinyl]phenyl]methyl]-2H-imidazol-2-one;

1-(2-phenylethyl)-4-butyl-1,3-dihydro-3-[[4-[3-(1H-tetrazol-5-yl)-2-pyridinyl]phenyl]methyl]-2H-imidazol-2-one;

1-propyl-4-butyl-5-methyl-1,3-dihydro-3-[[4-[3-(1H-tetrazol-5-yl)-2-pyridinyl]phenyl]methyl]-2H-imidazol-2-one;

1,4-dibutyl-5-methyl-1,3-dihydro-3-[[4-[3-(1H-tetrazol-5-yl)-2-pyridinyl]phenyl]methyl]-2H-imidazol-2-one;

1-pentyl-4-butyl-5-methyl-1,3-dihydro-3-[[4-[3-(1H-tetrazol-5-yl)-2-pyridinyl]phenyl]methyl]-2H-imidazol-2-one;

1-isopentyl-4-butyl-5-methyl-1,3-dihydro-3-[[4-[3-(1H-tetrazol-5-yl)-2-pyridinyl]phenyl]methyl]-2H-imidazol-2-one;

1-cyclohexylmethyl-4-butyl-5-methyl-1,3-dihydro-3-[[4-[3-(1H-tetrazol-5-yl)-2-pyridinyl]phenyl]methyl]-2H-imidazol-2-one;

1-phenylmethyl-4-butyl-5-methyl-1,3-dihydro-3-[[4-[3-(1H-tetrazol-5-yl)-2-pyridinyl]phenyl]methyl]-2H-imidazol-2-one;

1-(2-cyclohexylethyl)-4-butyl-5-methyl-1,3-dihydro-3-[[4-[3-(1H-tetrazol-5-yl)-2-pyridinyl]phenyl]methyl]-2H-imidazol-2-one;

1-(2-phenylethyl)-4-butyl-5-methyl-1,3-dihydro-3-[[4-[3-(1H-tetrazol-5-yl)-2-pyridinyl]phenyl]methyl]-2H-imidazol-2-one;

1propyl-4-butyl-5-chloro-1,3-dihydro-3-[[4-[3-(1H-tetrazol-5-yl)-2-pyridinyl]phenyl]methyl]-2H-imidazol-2-one;

1,4-dibutyl-5-chloro-1,3-dihydro-3-[[4-[3-(1H-tetrazol-5-yl)-2-pyridinyl]phenyl]methyl]-2H-imidazol-2-one;

1-pentyl-4-butyl-5-chloro-1,3-dihydro-3-[[4-[3-(1H-tetrazol-5-yl)-2-pyridinyl]phenyl]methyl]-2H-imidazol-2-one;

1-isopentyl-4-butyl-5-chloro-1,3-dihydro-3-[[4-[3-(1H-tetrazol-5-yl)-2-pyridinyl]phenyl]methyl]-2H-imidazol-2-one;

1-cyclohexylmethyl-4-butyl-5-chloro-1,3-dihydro-3-[[4-[3-(1H-tetrazol-5-yl)-2-pyridinyl]phenyl]methyl]-2H-imidazol-2-one;

1-phenylmethyl-4-butyl-5-chloro-1,3-dihydro-3-[[4-[3-(1H-tetrazol-5-yl)-2-pyridinyl]phenyl]methyl]-2H-imidazol-2-one;

1-(2-cyclohexylethyl)-4-butyl-5-chloro-1,3-dihydro-3-[[4-[3-(1H-tetrazol-5-yl)-2-pyridinyl]phenyl]methyl]-2H-imidazol-2-one; and 1(2-phenylethyl)-4-butyl-5-chloro-1,3-dihydro-3-[[4-[3-(1H-tetrazol-5yl)-2-pyridinyl]phenyl]methyl]-2H-imidazol-2-one.

12. The method of claim 5 wherein said angiotensin II receptor antagonist compound is selected from a family of compounds of Formula V

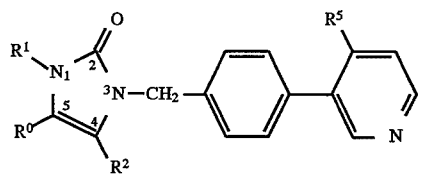

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylethyl, benzoyl, 1-oxo-2-phenethyl, 1-oxopropyl, 1-oxobutyl, 1-oxopentyl and 2-hydroxybutyl; wherein $R^o$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

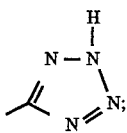

or a tautomer thereof or a pharmaceutically-acceptable salt thereof.

13. The method of claim 12 wherein said angiotensin II receptor antagonist compound is selected from compounds and their pharmaceutically-acceptable salts of the group of compounds consisting of 1-propyl-4-butyl-1,3-dihydro-3-[[4-[4-(1H-tetrazol-5-yl)-3-pyridinyl]phenyl]methyl]-2H-imidazol-2-one;

1,4-dibutyl-1,3-dihydro-3-[[4-[4-(1H-tetrazol-5-yl)-3-pyridinyl]phenyl]methyl]-2H-imidazol-2-one;

1-pentyl-4-butyl-1,3-dihydro-3-[[4-[4-(1H-tetrazol-5-yl)-3-pyridinyl]phenyl]methyl]-2H-imidazol-2-one;

1-isopentyl-4-butyl-1,3-dihydro-3-[[4-[4-(1H-tetrazol-5-yl)-3-pyridinyl]phenyl]methyl]-2H-imidazol-2-one;

1-cyclohexylmethyl-4-butyl-1,3-dihydro-3-[[4-[4-(1H-tetrazol-5-yl)-3-pyridinyl]phenyl]methyl]-2H-imidazol-2-one;

1-phenylmethyl-4-butyl-1,3-dihydro-3-[[4-[4-(1H-tetrazol-5-yl)-3-pyridinyl]phenyl]methyl]-2H-imidazol-2-one;

1-(2-cyclohexylethyl)-4-butyl-1,3-dihydro-3-[[4-[4-(1H-tetrazol-5-yl)-3-pyridinyl]phenyl]methyl]-2H-imidazol-2-one;

1-(2-phenylethyl)-4-butyl-1,3-dihydro-3-[[4-[4-(1H-tetrazol-5-yl)-3-pyridinyl]phenyl]methyl]-2H-imidazol-2-one;

1-propyl-4-butyl-5-methyl-1,3-dihydro-3-[[4-[4-(1H-tetrazol-5-yl)-3-pyridinyl]phenyl]methyl]-2H-imidazol-2-one;

1,4-dibutyl-5-methyl-1,3-dihydro-3-[[4-[4-(1H-tetrazol-5-yl)-3-pyridinyl]phenyl]methyl]-2H-imidazol-2-one;

1-pentyl-4-butyl-5-methyl-1,3-dihydro-3-[[4-[4-(1H-tetrazol-5-yl)-3-pyridinyl]phenyl]methyl]-2H-imidazol-2-one;

1-isopentyl-4-butyl-5-methyl-1,3-dihydro-3-[[4-[4-(1H-tetrazol-5-yl)-3-pyridinyl]phenyl]methyl]-2H-imidazol-2-one;

1-cyclohexylmethyl-4-butyl-5-methyl-1,3-dihydro-3-[[4-[4-(1H-tetrazol-5-yl)-3-pyridinyl]phenyl]methyl]-2H-imidazol-2-one;

1-phenylmethyl-4-butyl-5-methyl-1,3-dihydro-3-[[4-[4-(1H-tetrazol-5-yl)-3-pyridinyl]phenyl]methyl]-2H-imidazol-2-one;

1-(2-cyclohexylethyl)-4-butyl-5-methyl-1,3-dihydro-3-[[4-[4-(1H-tetrazol-5-yl)-3-pyridinyl]phenyl]methyl]-2H-imidazol-2-one;

1-(2-phenylethyl)-4-butyl-5-methyl-1,3-dihydro-3-[[4-[4-(1H-tetrazol-5-yl)-3-pyridinyl]phenyl]methyl]-2H-imidazol-2-one;

1-propyl-4-butyl-5-chloro-1,3-dihydro-3-[[4-[4-(1H-tetrazol-5-yl)-3-pyridinyl]phenyl]methyl]-2H-imidazol-2-one;

1,4-dibutyl-5-chloro-1,3-dihydro-3-[[4-[4-(1H-tetrazol-5-yl)-3-pyridinyl]phenyl]methyl]-2H-imidazol-2-one;

1-pentyl-4-butyl-5-chloro-1,3-dihydro-3-[[4-[4-(1H-tetrazol-5-yl)-3-pyridinyl]phenyl]methyl]-2H-imidazol-2-one;

1-isopentyl-4-butyl-5-chloro-1,3-dihydro-3-[[4-[4-(1H-tetrazol-5-yl)-3-pyridinyl]phenyl]methyl]-2H-imidazol-2-one;

1-cyclohexylmethyl-4-butyl-5-chloro-1,3-dihydro-3-[[4-[4-(1H-tetrazol-5-yl)-3-pyridinyl]phenyl]methyl]-2H-imidazol-2-one;

1-phenylmethyl-4-butyl-5-chloro-1,3-dihydro-3-[[4-[4-(1H-tetrazol-5-yl)-3-pyridinyl]phenyl]methyl]-2H-imidazol-2-one;

1-(2-cyclohexylethyl)-4-butyl-5-chloro-1,3-dihydro-3-[[4-[4-(1H-tetrazol-5-yl)-3-pyridinyl]phenyl]methyl]-2H-imidazol-2-one;

1-(2-phenylethyl)-4-butyl-5-chloro-1,3-dihydro-3-[[4-[4-(1H-tetrazol-5-yl)-3-pyridinyl]phenyl]methyl]-2H-imidazol-2-one;

1-propyl-4-butyl-5-chloro-1,3-dihydro-3-[[4-[4-(1H-tetrazol-5-yl)-3-pyridinyl]phenyl]methyl]-2H-imidazol-2-one;

1,4-dibutyl-5-chloro-1,3-dihydro-3-[[4-[4-(1H-tetrazol-5-yl)-3-pyridinyl]phenyl]methyl]-2H-imidazol-2-one;

1-pentyl-4-butyl-5-chloro-1,3-dihydro-3-[[4-[4-(1H-tetrazol-5-yl)-3-pyridinyl]phenyl]methyl]-2H-imidazol-2-one;

1-isopentyl-4-butyl-5-chloro-1,3-dihydro-3-[[4-[4-(1H-tetrazol-5-yl)-3-pyridinyl]phenyl]methyl]-2H-imidazol-2-one;

1-cyclohexylmethyl-4-butyl-5-chloro-1,3-dihydro-3-[[4-[4-(1H-tetrazol-5-yl)-3-pyridinyl]phenyl]methyl]-2H-imidazol-2-one;

1-phenylmethyl-4-butyl-5-chloro-1,3-dihydro-3-[[4-[4-(1H-tetrazol-5-yl)-3-pyridinyl]phenyl]methyl]-2H-imidazol-2-one;

1-(2-cyclohexylethyl)-4-butyl-5-chloro-1,3-dihydro-3-[[4-[4-(1H-tetrazol-5-yl)-3-pyridinyl]phenyl]methyl]-2H-imidazol-2-one; and 1-(2-phenylethyl)-4-butyl-5-chloro-1,3-dihydro-3-[[4-[4-(1H-tetrazol-5-yl)-3-pyridinyl]phenyl]methyl]-2H-imidazol-2-one.

14. The method of claim 5 wherein said angiotensin II receptor antagonist compound is selected from a family of compounds of Formula VI

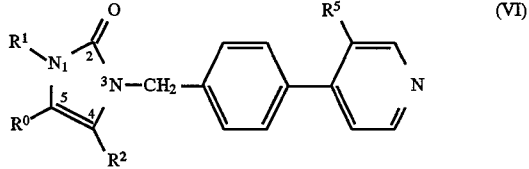

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylmethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

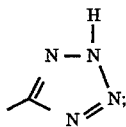

or a tautomer thereof or a pharmaceutically-acceptable salt thereof.

15. The method of claim 14 wherein said angiotensin II receptor antagonist compound is selected from compounds and their pharmaceutically-acceptable salts of the group of compounds consisting of 1-propyl-4-butyl-1,3-dihydro-3-[[4-[3-(1H-tetrazol-5-yl)-4-pyridinyl]phenyl]methyl]-2H-imidazol-2-one;

1,4-dibutyl-1,3-dihydro-3-[[4-[3-(1H-tetrazol-5-yl)-4-pyridinyl]phenyl]methyl]-2H-imidazol-2-one;

1-pentyl-4-butyl-1,3-dihydro-3-[[4-[3-(1H-tetrazol-5-yl)-4-pyridinyl]phenyl]methyl]-2H-imidazol-2-one;

1-isopentyl-4-butyl-1,3-dihydro-3-[[4-[3-(1H-tetrazol-5-yl)-4-pyridinyl]phenyl]methyl]-2H-imidazol-2-one;

1-cyclohexylmethyl-4-butyl-1,3-dihydro-3-[[4-[3-(1H-tetrazol-5-yl)-4-pyridinyl]phenyl]methyl]-2H-imidazol-2-one;

1-phenylmethyl-4-butyl-1,3-dihydro-3-[[4-[3-(1H-tetrazol-5-yl)-4-pyridinyl]phenyl]methyl]-2H-imidazol-2-one;

1-(2-cyclohexylethyl)-4-butyl-1,3-dihydro-3-[[4-[3-(1H-tetrazol-5-yl)-4-pyridinyl]phenyl]methyl]-2H-imidazol-2-one;

1-(2-phenylethyl)-4-butyl-1,3-dihydro-3-[[4-[3-(1H-tetrazol-5-yl)-4-pyridinyl]phenyl]methyl]-2H-imidazol-2-one;

1-propyl-4-butyl-5-methyl-1,3-dihydro-3-[[4-[3-(1H-tetrazol-5-yl)-4-pyridinyl]phenyl]methyl]-2H-imidazol-2-one;

1,4-dibutyl-5-methyl-1,3-dihydro-3-[[4-[3-(1H-tetrazol-5-yl)-4-pyridinyl]phenyl]methyl]-2H-imidazol-2-one;

1-pentyl-4-butyl-5-methyl-1,3-dihydro-3-[[4-[3-(1H-tetrazol-5-yl)-4-pyridinyl]phenyl]methyl]-2H-imidazol-2-one;

1-isopentyl-4-butyl-5-methyl-1,3-dihydro-3-[[4-[3-(1H-tetrazol-5-yl)-4-pyridinyl]phenyl]methyl]-2H-imidazol-2-one;

1-cyclohexylmethyl-4-butyl-5-methyl-1,3-dihydro-3-[[4-[3-(1H-tetrazol-5-yl)-4-pyridinyl]phenyl]methyl]-2H-imidazol-2-one;

1-phenylmethyl-4-butyl-5-methyl-1,3-dihydro-3-[[4-[3-(1H-tetrazol-5-yl)-4-pyridinyl]phenyl]methyl]-2H-imidazol-2-one;

1-(2-cyclohexylethyl)-4-butyl-5-methyl-1,3-dihydro-3-[[4-[3-(1H-tetrazol-5-yl)-4-pyridinyl]phenyl]methyl]-2H-imidazol-2-one;

1-(2-phenylethyl)-4-butyl-5-methyl-1,3-dihydro-3-[[4-[3-(1H-tetrazol-5-yl)-4-pyridinyl]phenyl]methyl]-2H-imidazol-2-one;

1-propyl-4-butyl-5-chloro-1,3-dihydro-3-[[4-[3-(1H-tetrazol-5-yl)-4-pyridinyl]phenyl]methyl]-2H-imidazol-2-one;

1,4-dibutyl-5-chloro-1,3-dihydro-3-[[4-[3-(1H-tetrazol-5-yl)-4-pyridinyl]phenyl]methyl]-2H-imidazol-2-one;

1-pentyl-4-butyl-5-chloro-1,3-dihydro-3-[[4-[3-(1H-tetrazol-5-yl)-4-pyridinyl]phenyl]methyl]-2H-imidazol-2-one;

1-isopentyl-4-butyl-5-chloro-1,3-dihydro-3-[[4-[3-(1H-tetrazol-5-yl)-4-pyridinyl]phenyl]methyl]-2H-imidazol-2-one;

1-cyclohexylmethyl-4-butyl-5-chloro-1,3-dihydro-3-[[4-[3-(1H-tetrazol-5-yl)-4-pyridinyl]phenyl]methyl]-2H-imidazol-2-one;

1-phenylmethyl-4-butyl-5-chloro-1,3-dihydro-3-[[4-[3-(1H-tetrazol-5-yl)-4-pyridinyl]phenyl]methyl]-2H-imidazol-2-one;

1-(2-cyclohexylethyl)-4-butyl-5-chloro-1,3-dihydro-3-[[4-[3-(1H-tetrazol-5-yl)-4-pyridinyl]phenyl]methyl]-2H-imidazol-2-one; and 1-(2-phenylethyl)-4-butyl-5-chloro-1,3-dihydro-3-[[4-[3-(1H-tetrazol-5-yl)-4-pyridinyl]phenyl]methyl]-2H-imidazol-2-one.

16. The method of claim 5 wherein said angiotensin II receptor antagonist compound is selected from a family of compounds of Formula VII

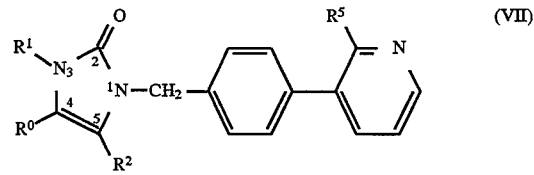

wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, cyclohexylethyl, cyclohexanoyl, 1-oxo-2-cyclohexylmethyl, benzoyl, 1-oxo-2-phenethyl, 1-oxopropyl, 1-oxobutyl, 1-oxopentyl and 2-hydroxybutyl; wherein $R^0$ is selected from hydrido, methyl, fluoro, chloro, monofluoromethyl, difluoromethyl, trifluoromethyl, formyl, carboxyl and dimethoxymethyl; wherein $R^2$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl and cyclohexylethyl; wherein $R^5$ is an acidic group selected from $CO_2H$ and

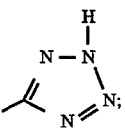

or a tautomer thereof or a pharmaceutically-acceptable salt thereof.

17. The method of claim 16 wherein said angiotensin II receptor antagonist compound is selected from compounds and their pharmaceutically-acceptable salts of the group of compounds consisting of 1-propyl-4-butyl-1,3-dihydro-3-[[4-[2-(1H-tetrazol-5-yl)-3-pyridinyl]phenyl]methyl]-2H-imidazol-2-one;

1,4-dibutyl-1,3-dihydro-3-[[4-[2-(1H-tetrazol-5-yl)-3-pyridinyl]phenyl]methyl]-2H-imidazol-2-one;

1-pentyl-4-butyl-1,3-dihydro-3-[[4-[2-(1H-tetrazol-5-yl)-3-pyridinyl]phenyl]methyl]-2H-imidazol-2-one;

1-isopentyl-4-butyl-1,3-dihydro-3-[[4-[2-(1H-tetrazol-5-yl)-3-pyridinyl]phenyl]methyl]-2H-imidazol-2-one;

1-cyclohexylmethyl-4-butyl-1,3-dihydro-3-[[4-[2-(1H-tetrazol-5-yl)-3-pyridinyl]phenyl]methyl]-2H-imidazol-2-one;

1-phenylmethyl-4-butyl-1,3-dihydro-3-[[4-[2-(1H-tetrazol-5-yl)-3-pyridinyl]phenyl]methyl]-2H-imidazol-2-one;

1-(2-cyclohexylethyl)-4-butyl-1,3-dihydro-3-[[4-[2-(1H-tetrazol-5-yl)-3-pyridinyl]phenyl]methyl]-2H-imidazol-2-one;

1-(2-phenylethyl)-4-butyl-1,3-dihydro-3-[[4-[2-(1H-tetrazol-5-yl)-3-pyridinyl]phenyl]methyl]-2H-imidazol-2-one;

1-propyl -4-butyl-5-methyl-1,3-dihydro-3-[[4-[2-(1H-tetrazol-5-yl)-3-pyridinyl]phenyl]methyl]-2H-imidazol-2-one;

1,4-dibutyl-5-methyl-1,3-dihydro-3-[[4-[2-(1H-tetrazol-5-yl)-3-pyridinyl]phenyl]methyl]-2H-imidazol-2-one;

1-pentyl-4-butyl-5-methyl-1,3-dihydro-3-[[4-[2-(1H-tetrazol-5-yl)-3-pyridinyl]phenyl]methyl]-2H-imidazol-2-one;

1-isopentyl-4-butyl-5-methyl-1,3-dihydro-3-[[4-[2-(1H-tetrazol-5-yl)-3-pyridinyl]phenyl]methyl]-2H-imidazol-2-one;

1-cyclohexylmethyl-4-butyl-5-methyl-1,3-dihydro-3-[[4-[2-(1H-tetrazol-5-yl)-3-pyridinyl]phenyl]methyl]-2H-imidazol-2-one;

1-phenylmethyl-4-butyl-5-methyl-1,3-dihydro-3-[[4-[2-(1H-tetrazol-5-yl)-3-pyridinyl]phenyl]methyl]-2H-imidazol-2-one;

1(2-cyclohexylethyl)-4-butyl-5-methyl-1,3-dihydro-3-[[4-[2-(1H-tetrazol-5-yl)-3-pyridinyl]phenyl]methyl]-2-H-imidazol-2-one;

1(2-phenylethyl)-4-butyl-5-methyl-1,3-dihydro-3-[[4-[2-(1H-tetrazol-5-yl)-3-pyridinyl]phenyl]methyl]-2H-imidazol-2-one;

1-propyl-4-butyl-5-chloro-1,3-dihydro-3-[[4-[2-(1H-tetrazol-5-yl)-3-pyridinyl]phenyl]methyl]-2H-imidazol-2-one;

1,4 -dibutyl-5-chloro-1,3-dihydro-3 -[[4-[2-(1H-tetrazol-5-yl)-3-pyridinyl]phenyl]methyl]-2H-imidazol-2-one;

1-pentyl-4-butyl-5-chloro-1,3-dihydro-3-[[4-[2-(1H-tetrazol-5-yl)-3-pyridinyl]phenyl]methyl]-2H-imidazol-2-one;

1-isopentyl-4-butyl-5-chloro-1,3-dihydro-3-[[4-[2-(1H-tetrazol-5-yl)-3-pyridinyl]phenyl]methyl]-2H-imidazol-2-one;

1-cyclohexylmethyl-4-butyl-5-chloro-1,3-dihydro-3-[[4-[2-(1H-tetrazol-5-yl)-3-pyridinyl]phenyl]methyl]-2H-imidazol-2-one;

1-phenylmethyl-4-butyl-5-chloro-1,3-dihydro-3-[[4-[2-(1H-tetrazol-5-yl)-3-pyridinyl]phenyl]methyl]-2H-imidazol-2-one;

1-(2-cyclohexylethyl)-4-butyl-5-chloro-1,3-dihydro-3-[[4-[2-(1H-tetrazol-5-yl)-3-pyridinyl]phenyl]methyl]-2H-imidazol-2-one; and 1-(2-phenylethyl)-4-butyl-5-chloro-1,3-dihydro-3-[[4-[2-(1H-tetrazol-5-yl)-3-pyridinyl]phenyl]methyl]-2H-imidazol-2-one.

18. The method of claim 9 wherein said angiotensin II receptor antagonist compound is 1,4-dibutyl-1,3-dihydro-3-[[6-[2-(1H-tetrazol-5-yl)phenyl]-3-pyridinyl]methyl]-2H-imidazol-2-one or a pharmaceutically-acceptable salt thereof.

* * * * *